US007511044B2

(12) United States Patent
Wang et al.

(10) Patent No.: US 7,511,044 B2
(45) Date of Patent: *Mar. 31, 2009

(54) VANILLOID RECEPTOR LIGANDS AND THEIR USE IN TREATMENTS

(75) Inventors: Hui-Ling Wang, Thousand Oaks, CA (US); Chenera Balan, Thousand Oaks, CA (US); Elizabeth M. Doherty, Newbury Park, CA (US); James R. Falsey, Moorpark, CA (US); Vijay Keshav Gore, Thousand Oaks, CA (US); Jodie Katon, Ventura, CA (US); Mark H. Norman, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 510 days.

This patent is subject to a terminal disclaimer.

(21) Appl. No.: 11/056,568

(22) Filed: Feb. 11, 2005

(65) Prior Publication Data
US 2005/0176726 A1    Aug. 11, 2005

Related U.S. Application Data

(60) Provisional application No. 60/543,896, filed on Feb. 11, 2004.

(51) Int. Cl.
*C07D 403/04* (2006.01)
*A61K 31/496* (2006.01)

(52) U.S. Cl. .................. 514/252.14; 514/252.18; 514/252.19; 514/252.2; 544/295

(58) Field of Classification Search .......... 544/295; 514/252.14, 252.18, 252.19, 252.2
See application file for complete search history.

(56) References Cited

U.S. PATENT DOCUMENTS

| 5,272,167 | A | 12/1993 | Girijavallabhan et al. |
| 5,459,144 | A | 10/1995 | Girijavallabhan et al. |
| 5,750,532 | A | 5/1998 | Girijavallabhan et al. |
| 5,916,887 | A | 6/1999 | Singh et al. |
| 5,932,590 | A | 8/1999 | Ciccarone et al. |
| 5,936,084 | A | 8/1999 | Jirousek et al. |
| 5,959,123 | A | 9/1999 | Singh et al. |
| 5,965,569 | A | 10/1999 | Camps Garcia et al. |
| 5,969,140 | A | 10/1999 | Ukita et al. |
| 6,093,737 | A | 7/2000 | Anthony et al. |
| 6,153,619 | A | 11/2000 | Wood et al. |
| 6,255,489 | B1 | 7/2001 | Klintz et al. |
| 6,306,866 | B1 | 10/2001 | Wood et al. |
| 6,407,111 | B1 | 6/2002 | Bös et al. |
| 6,562,847 | B1 | 5/2003 | Lee |
| 6,569,847 | B1 | 5/2003 | Singh et al. |
| 6,593,330 | B2 | 7/2003 | Nilsson |
| 6,596,773 | B2 | 7/2003 | Bös et al. |
| 6,610,677 | B2 | 8/2003 | Davies et al. |
| 6,613,776 | B2 | 9/2003 | Knegtel et al. |
| 2002/0151712 | A1 | 10/2002 | Lin et al. |
| 2003/0195201 | A1 | 10/2003 | Bo et al. |
| 2004/0038969 | A1 | 2/2004 | Doherty et al. |
| 2004/0082780 | A1 | 4/2004 | Doherty et al. |
| 2004/0204386 | A1 | 10/2004 | Bhatt et al. |

FOREIGN PATENT DOCUMENTS

| EP | 0 168 262 | 1/1986 |
| EP | 0 937 459 | 1/1999 |
| WO | WO 92/04333 | 3/1992 |
| WO | WO 97/00612 | 1/1997 |
| WO | WO 97/13754 | 4/1997 |
| WO | WO 97/41127 | 11/1997 |
| WO | WO 98/12176 | 3/1998 |
| WO | WO 98/12210 | 3/1998 |
| WO | WO 98/23155 | 6/1998 |
| WO | WO 98/23156 | 6/1998 |
| WO | WO 98/28980 | 7/1998 |
| WO | WO 99/12911 | 3/1999 |
| WO | WO 99/28314 | 6/1999 |
| WO | WO 99/41248 | 8/1999 |
| WO | WO 99/51241 | 10/1999 |
| WO | WO 00/59881 | 10/2000 |
| WO | WO 01/05768 | 1/2001 |
| WO | WO 01/07032 | 2/2001 |
| WO | WO 01/07401 | 2/2001 |
| WO | WO 01/14331 | 3/2001 |

(Continued)

OTHER PUBLICATIONS

Ulrich, Chapter 4: Crystallization, Kirk-Othmer Encyclopedia of Chemical Technology, Aug. 2002.*
Vippagunta et al., Cyrstalline Solids, Advanced Drug Delivery Reviews, 48, pp. 3-26, 2001.*
West, Solid Solutions, Solid State Chemistry and its applications, pp. 358 & 365, 1988.*
Valenzano et al., PubMed Abstract (Curr Med Chem. 11(24):3185-202) Dec. 2004.*
Szallasi et al., Vanilloid Receptor TRPV1 Antagonists as the Next Generation of Painkillers—Miniperspective, Journal of Medicinal Chemistry, vol. 47, No. 11, pp. 2717-2723, May 2004.*

*Primary Examiner*—Deepak Rao
(74) *Attorney, Agent, or Firm*—Richard V. Parson

(57) ABSTRACT

Pyrimidine ethers and compositions containing them, for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

5 Claims, No Drawings

FOREIGN PATENT DOCUMENTS

| | | |
|---|---|---|
| WO | WO 01/19817 | 3/2001 |
| WO | WO 01/53263 | 7/2001 |
| WO | WO 01/54503 | 8/2001 |
| WO | WO 01/74331 | 10/2001 |
| WO | WO 01/76582 | 10/2001 |
| WO | WO 02/00651 | 1/2002 |
| WO | WO 02/16324 | 2/2002 |
| WO | WO 02/18339 | 3/2002 |
| WO | WO 02/26712 | 4/2002 |
| WO | WO 02/32872 | 4/2002 |
| WO | WO 02/50052 | 6/2002 |
| WO | WO 02/079197 | 10/2002 |
| WO | WO 02/080853 | 10/2002 |
| WO | WO 02/088111 | 11/2002 |
| WO | WO 03/006471 | 1/2003 |
| WO | WO 03/028729 | 4/2003 |
| WO | WO 03/029210 | 4/2003 |
| WO | WO 03/041649 | 5/2003 |
| WO | WO 03/049702 | 6/2003 |
| WO | WO 03/093242 | 11/2003 |
| WO | WO 2004/005283 | 1/2004 |
| WO | WO 2004/014871 | 2/2004 |
| WO | WO 2004/046133 | 6/2004 |
| WO | WO 2004/065378 | 8/2004 |
| WO | WO 2004/089286 | 10/2004 |

\* cited by examiner

VANILLOID RECEPTOR LIGANDS AND THEIR USE IN TREATMENTS

This application claims the benefit of U.S. Provisional Application No. 60/543,896, filed Feb. 11, 2004, which is hereby incorporated by reference.

BACKGROUND

The vanilloid receptor 1 (VR1) is the molecular target of capsaicin, the active ingredient in hot peppers. Julius et al. reported the molecular cloning of VR1 (Caterina et al., 1997). VR1 is a non-selective cation channel which is activated or sensitized by a series of different stimuli including capsaicin and resiniferatoxin (exogenous activators), heat & acid stimulation and products of lipid bilayer metabolism, anandamide (Premkumar et al., 2000, Szabo et al., 2000, Gauldie et al., 2001, Olah et al., 2001) and lipoxygenase metabolites (Hwang et al., 2000). VR1 is highly expressed in primary sensory neurons (Caterina et al., 1997) in rats, mice and humans (Onozawa et al., 2000, Mezey et al., 2000, Helliwell et al., 1998, Cortright et al., 2001). These sensory neurons innervate many visceral organs including the dermis, bones, bladder, gastrointestinal tract and lungs; VR1 is also expressed in other neuronal and non-neuronal tissues including but not limited to, CNS nuclei, kidney, stomach and T-cells (Nozawa et al., 2001, Yiangou et al., 2001, Birder et al., 2001). Presumably expression in these various cells and organs may contribute to their basic properties such as cellular signaling and cell division.

Prior to the molecular cloning of VR1, experimentation with capsaicin indicated the presence of a capsaicin sensitive receptor, which could increase the activity of sensory neurons in humans, rats and mice (Holzer, 1991; Dray, 1992, Szallasi and Blumberg 1996, 1999). The results of acute activation by capsaicin in humans was pain at injection site and in other species increased behavioral sensitivity to sensory stimuli (Szallasi and Blumberg, 1999). Capsaicin application to the skin in humans causes a painful reaction characterized not only by the perception of heat and pain at the site of administration but also by a wider area of hyperalgesia and allodynia, two characteristic symptoms of the human condition of neuropathic pain (Holzer, 1991). Taken together, it seems likely that increased activity of VR1 plays a significant role in the establishment and maintenance of pain conditions. Topical or intradermal injection of capsaicin has also been shown to produce localized vasodilation and edema production (Szallasi and Blumberg 1999, Singh et al., 2001). This evidence indicates that capsaicin through it's activation of VR1 can regulate afferent and efferent function of sensory nerves. Sensory nerve involvement in diseases could therefore be modified by molecules which effect the function of the vanilloid receptor to increase or decrease the activity of sensory nerves.

VR1 gene knockout mice have been shown to have reduced sensory sensitivity to thermal and acid stimuli (Caterina et al., 2000)). This supports the concept that VR1 contributes not only to generation of pain responses (i.e. via thermal, acid or capsaicin stimuli) but also to the maintenance of basal activity of sensory nerves. This evidence agrees with studies demonstrating capsaicin sensitive nerve involvement in disease. Primary sensory nerves in humans and other species can be made inactive by continued capsaicin stimulation. This paradigm causes receptor activation induced desensitization of the primary sensory nerve—such reduction in sensory nerve activity in vivo makes subjects less sensitive to subsequent painful stimuli. In this regard both capsaicin and resiniferatoxin (exogenous activators of VR1), produce desensitization and they have been used for many proof of concept studies in in vivo models of disease (Holzer, 1991, Dray 1992, Szallasi and Blumberg 1999).

BIBLIOGRAPHY

Birder-L A. Kanai-A J. de-Groat-W C. Kiss-S. Nealen-M L. Burke-N E. Dineley-K E. Watkins-S. Reynolds-I J. Caterina-M J. (2001) Vanilloid receptor expression suggests a sensory role for urinary bladder epithelial cells. PNAS 98: 23: 13396-13401.

Caterina, M. J, Schumacher, M. A., Tominaga, M., Rosen, T. A., Levine, J. D., and Julius, D, (1997). The capsaicin receptor: a heat-activated ion channel in the pain pathway. Nature 389: 816-824.

Caterina-M J. Leffler-A. Malmberg-A B. Martin-W J. Trafton-J. Petersen-Zeitz K R. Koltzenburg-M. Basbaum-A I. Julius-D (2000) Impaired nociception and pain sensation in mice lacking the capsaicin receptor. Science-(WASH-DC). 288: 5464: 306-313.

Cortright-D N. Crandall-M. Sanchez-J F. Zou-T. Krause-J E. White-G (2001) The tissue distribution and functional characterization of human VR1. Biochemical and Biophysical Research Communications 281: 5: 1183-1189

Dray, A., (1992). Therapeutic potential of capsaicin-like molecules. Life Sciences 51: 1759-1765.

Gauldie-S D. McQueen-D S. Pertwee-R. Chessell-I P. (2001) Anandamide activates peripheral nociceptors in normal and arthritic rat knee joints. British Journal of Pharmacology 132: 3: 617-621.

Helliwell-R J A. McLatchie-L M. Clarke-M. Winter-J. Bevan-S. McIntyre-P (1998) Capsaicin sensitivity is associated with expression of the vanilloid (capsaicin) receptor (VR1) mRNA in adult rat sensory ganglia. Neuroscience Lett. 250: 3: 177-180.

Holzer, P. (1991) Capsaicin: Cellular targets, Mechanisms of Action and selectivity for thin sensory neurons. Pharmacological reviews 43: 2: 143-201

Hwang-S W. Cho-H. Kwak-J. Lee-S Y. Kang-C J. Jung-J. Cho-S. Min-K H. Suh-Y G. Kim-D. Oh-U. (2000) Direct activation of capsaicin receptors by products of lipoxygenases: Endogenous capsaicin-like substances. PNAS 97: 11: 6155-6160.

Mezey-E. Toth-Z E. Cortright-D N. Arzubi-M K. Krause-J E. Elde-R. Guo-A. Blumberg-P M. Szallasi-A (2000) Distribution of mRNA for vanilloid receptor subtype 1 (VR1), and VR1-like immunoreactivity, in the central nervous system of the rat and human.

PNAS 97: 7: 3655-3660.

Nozawa-Y. Nishihara-K. Yamamoto-A. Nakano-M. Ajioka-H. Matsuura-N.(2001) Distribution and characterization of vanilloid receptors in the rat stomach. Neuroscience Letters 309: 1: 33-36.

Olah-Z. Karai-L. Iadarola-M J. (2001) Anandamide activates vanilloid receptor 1 (VR1) at acidic pH in dorsal root ganglia neurons and cells ectopically expressing VR1. Journal of Biological Chemistry 276: 33, 31163-31170.

Onozawa-K. Nakamura-A. Tsutsumi-S. Yao-J. Ishikawa-R. Kohama-K. (2000) Tissue distribution of capsaicin receptor in the various organs of rats. Proc. Jpn. Acad. Ser. B, Phys.-Biol. Sci. 76: 5: 68-72.

Premkumar-L S. Ahern-G P. (2000) Induction of vanilloid receptor channel activity by protein kinase C. Nature (London) 408: 6815: 985-990.

Singh-L K. Pang-X. Alexacos-N. Letourneau-R. Theoharides-T C. (1999) Acute immobilization stress triggers skin mast cell degranulation via corticotropin releasing hormone, neurotensin, and substance P: A link to neurogenic skin disorders. Brain Behav. Immun. 13: 3: 225-239.

Szallasi, A. Blumberg-P M (1996) Vanilloid receptors: New insights enhance potential as a therapeutic target. Pain 68: 195-208

Szallasi-A. Blumberg-P M. (1999) Vanilloid (capsaicin) receptors and mechanisms. Pharmacol. Rev. 51: 2: 159-211.

Szabo-T. Wang-J. Gonzalez-A. Kedei-N. Lile-J. Treanor-J. Blumberg-P M. (2000) Pharmacological characterization of the human vanilloid receptor type-1 (hVR1). Society for Neuroscience Abstracts. 26: 1-2: 634.18.

Tominaga, M., Caterina, M. J., Malmberg, A. B., Rosen, T. A., Gilbert, H., Skinner, K., Raumann, B. E., Basbaum, A. I., and Julius, D., (1998). The cloned capsaicin receptor integrates multiple pain-producing stimuli. Neuron 21: 531-543.

Yiangou-Y. Facer-P. Dyer-N H.C. Chan-C L H. Knowles-C. Williams-N S. Anand-P. (2001) Vanilloid receptor 1 immunoreactivity in inflamed human bowel. Lancet (North American Edition) 357: 9265: 1338-1339.

Yiangou-Y. Facer-P. Ford-A. Brady-C. Wiseman-O. Fowler-C J. Anand-P. (2001) Capsaicin receptor VR1 and ATP-gated ion channel P2X3 in human urinary bladder. BJU International 87: 9: 774-779.

Wang-H. Bian-D. Zhu-D. Zajic-G. Loeloff-R. Lile-J. Wild-K. Treanor-J. Curran-E. (2000) Inflammation-induced upregulation of VR1 in rat spinal cord and DRG correlates with enhanced nociceptive processing. Society for Neuroscience Abstracts 26:1-2: 632.15.

SUMMARY

The present invention comprises a new class of compounds useful in the treatment of diseases, such as vanilloid-receptor-mediated diseases and other maladies, such as inflammatory or neuropathic pain and diseases involving sensory nerve function such as asthma, rheumatoid arthritis, osteoarthritis, inflammatory bowel disorders, urinary incontinence, migraine and psoriasis. In particular, the compounds of the invention are useful for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, anxiety, depression, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. Accordingly, the invention also comprises pharmaceutical compositions comprising the compounds, methods for the treatment of vanilloid-receptor-mediated diseases, such as inflammatory or neuropathic pain, asthma, rheumatoid arthritis, osteoarthritis, inflammatory bowel disorders, urinary incontinence, migraine and psoriasis diseases, using the compounds and compositions of the invention, and intermediates and processes useful for the preparation of the compounds of the invention.

The compounds of the invention are represented by the following general structure:

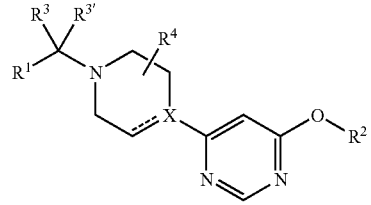

or a pharmaceutically acceptable salt thereof, wherein $R^1$, $R^2$, $R^3$, $R^{3'}$, $R^4$ and X are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION

One aspect of the current invention relates to compounds having the general structure:

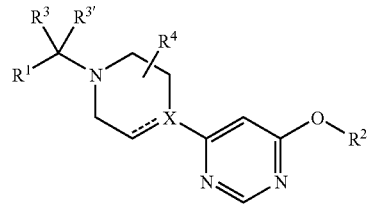

or any pharmaceutically-acceptable salt or hydrate thereof, wherein:

X is N or C; wherein, when X is N,

represents single bond, and when X is C, then

represents a single or double bond;

$R^1$ is a saturated, partially saturated or unsaturated 5-, 6- or 7-membered ring containing 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=NR$^a$)NR$^aR^a$, —OR$^a$, —OC(=O)$R^b$, —OC(=O)NR$^aR^a$, —OC(=O)N(R$^a$)S(=O)$_2R^b$, —OC$_{2-6}$alkylNR$^aR^a$, —OC$_{2-6}$alkylOR$^a$, —SR$^a$, —S(=O)$R^b$, —S(=O)$_2R^b$, —S(=O)$_2$NR$^aR^a$, —S(=O)$_2$N(R$^a$)C(=O)$R^b$, —S(=O)$_2$N(R$^a$)C(=O)OR$^b$, —S(=O)$_2$N(R$^a$)C(=O) NR$^aR^a$, —NR$^aR^a$, —N(R$^a$)C(=O)$R^b$, —N(R$^a$)C(=O)OR$^b$, —N(R$^a$)C(=O)NR$^aR^a$, —N(R$^a$)C(=NR$^a$)NR$^aR^a$, —N(R$^a$)S(=O)$_2R^b$, —N(R$^a$)S(=O)$_2$NR$^aR^a$, —NR$^aC_{2-6}$alkylNR$^aR^a$ and —NR$^aC_{2-6}$alkylOR$^a$; or $R^1$ is phenyl substituted by 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$;

$R^2$ is independently a partially saturated or unsaturated 8-, 9-, 10- or 11-membered bicyclic ring containing 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$; or $R^2$ is independently a partially saturated or unsaturated 9-, 10- or 11-membered bicyclic carbocyclic ring substituted by 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$;

$R^3$ and $R^{3'}$ are independently, at each instance, H, methyl or ethyl; or $R^3$ and $R^{3'}$ together may be combined with the carbon atom to which they are attached to form cyclopropyl;

$R^4$ is H or methyl;

$R^a$ is independently, at each instance, H or $R^b$; and $R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —O$C_{1-4}$alkyl, —NH$_2$, —NH$C_{1-4}$alkyl, —N($C_{1-4}$alkyl)$C_{1-4}$alkyl.

One aspect of the current invention relates to compounds having the general structure:

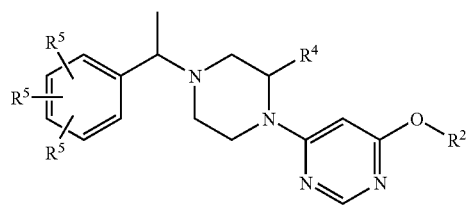

or any pharmaceutically-acceptable salt thereof, wherein:

$R^2$ is independently a partially saturated or unsaturated 8-, 9-, 10- or 11-membered bicyclic ring containing 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$; or $R^2$ is independently a partially saturated or unsaturated 9-, 10- or 11-membered bicyclic carbocyclic ring substituted by 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$;

$R^4$ is H or methyl;

$R^5$ is independently in each instance selected from H, $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$;

$R^a$ is independently, at each instance, H or $R^b$; and $R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —O$C_{1-4}$alkyl, —NH$_2$, —NH$C_{1-4}$alkyl, —N($C_{1-4}$alkyl)$C_{1-4}$alkyl.

Another aspect of the current invention relates to compounds having the general structure:

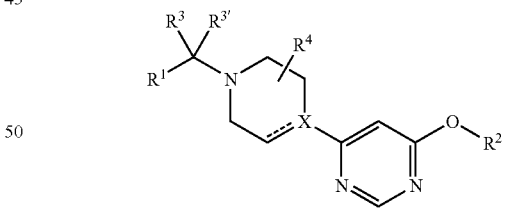

or any pharmaceutically-acceptable salt thereof, wherein:

X is N or C; wherein, when X is N,

represents single bond, and when X is C, then

represents a single or double bond;

$R^1$ is a saturated, partially saturated or unsaturated 5-, 6- or 7-membered ring containing 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$; or $R^1$ is phenyl substituted by 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$;

$R^2$ is independently a partially saturated or unsaturated 8-, 9-, 10- or 11-membered bicyclic ring containing 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$;

$R^3$ and $R^{3'}$ are independently, at each instance, H, methyl or ethyl; or $R^3$ and $R^{3'}$ together may be combined with the carbon atom to which they are attached to form cyclopropyl;

$R^4$ is H or methyl;

$R^a$ is independently, at each instance, H or $R^b$; and $R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —O$C_{1-4}$alkyl, —NH$_2$, —NH$C_{1-4}$alkyl, —N($C_{1-4}$alkyl)$C_{1-4}$alkyl.

In another embodiment, in conjunction with any one of the above and below embodiments, the current invention has the general structure:

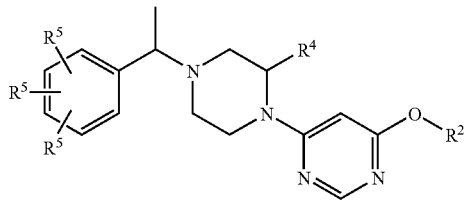

or any pharmaceutically-acceptable salt thereof, wherein:

$R^2$ is independently a partially saturated or unsaturated 8-, 9-, 10- or 11-membered bicyclic ring containing 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$;

$R^4$ is H or methyl;

$R^5$ is independently in each instance selected from H, $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$;

$R^a$ is independently, at each instance, H or $R^b$; and $R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —O$C_{1-4}$alkyl, —NH$_2$, —NH$C_{1-4}$alkyl, —N($C_{1-4}$alkyl)$C_{1-4}$alkyl.

In another embodiment, in conjunction with any one of the above and below embodiments, the current invention has the general structure:

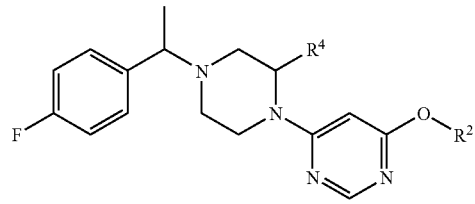

or any pharmaceutically-acceptable salt thereof, wherein:

$R^2$ is independently a partially saturated or unsaturated 8-, 9-, 10- or 11-membered bicyclic ring containing 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, $R^4$ is H or methyl;

$R^a$ is independently, at each instance, H or $R^b$; and $R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —O$C_{1-4}$alkyl, —NH$_2$, —NH$C_{1-4}$alkyl, —N($C_{1-4}$alkyl)$C_{1-4}$alkyl.

In another embodiment, in conjunction with any one of the above and below embodiments, X is N and

represents a single bond.

In another embodiment, in conjunction with any one of the above and below embodiments, X is C and

represents a double bond.

In another embodiment, in conjunction with any one of the above and below embodiments, X is C and

represents a single bond.

In another embodiment, in conjunction with any one of the above and below embodiments, $R^1$ is a saturated, partially saturated or unsaturated 5-, 6- or 7-membered ring containing 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$.

In another embodiment, in conjunction with any one of the above and below embodiments, $R^1$ is pyridinyl, furanyl, thiophenyl or pyrimidinyl, any of which is substituted by 0, 1, 2 or 3 substituents selected from $C_{1-8}$alkyl, $C_{1-4}$haloalkyl and halo.

In another embodiment, in conjunction with any one of the above and below embodiments, $R^1$ is pyridinyl, furanyl, thiophenyl or pyrimidinyl, any of which is substituted by 1, 2 or 3 substituents selected from $C_{1-8}$alkyl, $C_{1-4}$haloalkyl and halo.

In another embodiment, in conjunction with any one of the above and below embodiments, $R^1$ is pyridinyl, furanyl, thiophenyl or pyrimidinyl.

In another embodiment, in conjunction with any one of the above and below embodiments, $R^1$ is phenyl substituted by 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$.

In another embodiment, in conjunction with any one of the above and below embodiments, $R^1$ is phenyl substituted by 1, 2 or 3 substituents selected from $C_{1-8}$alkyl, $C_{1-4}$haloalkyl, halo and —O$R^a$;

In another embodiment, in conjunction with any one of the above and below embodiments, $R^2$ is independently a partially saturated or unsaturated 8-, 9-, 10- or 11-membered bicyclic ring containing 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$.

In another embodiment, in conjunction with any one of the above and below embodiments, $R^2$ is independently a partially saturated or unsaturated 9-, 10- or 11-membered bicyclic carbocyclic ring substituted by 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$;

In another embodiment, in conjunction with any one of the above and below embodiments, $R^2$ is quinolin-8-yl, benzoxazol-4-yl, benzothiazol-4-yl or quinoxalinon-5-yl, either of which is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —C(=O)N$R^aR^a$, —OC(=O)N($R^a$) S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$.

In another embodiment, in conjunction with any one of the above and below embodiments, $R^3$ is H.

In another embodiment, in conjunction with any one of the above and below embodiments, $R^{3'}$ is methyl.

In another embodiment, in conjunction with any one of the above and below embodiments, $R^3$ and $R^{3'}$ combine with the carbon atom to which they are attached to form cyclopropyl.

In another embodiment, in conjunction with any one of the above and below embodiments, $R^4$ is H. In another embodiment, in conjunction with any one of the above and below embodiments, $R^4$ is methyl.

Another aspect of the invention relates to a method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, anxiety, depression, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to any of the above embodiments.

Another aspect of the invention relates to a pharmaceutical composition comprising a compound according to any of the above embodiments and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, anxiety, depression, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

The compounds of this invention may have in general several asymmetric centers and are typically depicted in the form of racemic mixtures. This invention is intended to encompass racemic mixtures, partially racemic mixtures and separate enantiomers and diasteromers.

Unless otherwise specified, the following definitions apply to terms found in the specification and claims:

"$C_{\alpha-\beta}$alkyl" means an alkyl group comprising a minimum of α and a maximum of β carbon atoms in a branched, cyclical or linear relationship or any combination of the three, wherein α and β represent integers. The alkyl groups described in this section may also contain one or two double or triple bonds. Examples of $C_{1-6}$alkyl include, but are not limited to the following:

-continued

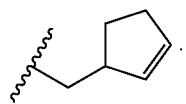

"Benzo group", alone or in combination, means the divalent radical $C_4H_4=$, one representation of which is —CH=CH—CH=CH—, that when vicinally attached to another ring forms a benzene-like ring—for example tetrahydronaphthylene, indole and the like. The terms "oxo" and "thioxo" represent the groups =O (as in carbonyl) and =S (as in thiocarbonyl), respectively.

"Halo" or "halogen" means a halogen atoms selected from F, Cl, Br and I.

"$C_{V-W}$haloalkyl" means an alkyl group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Examples of heterocycles that may be found in the claims include, but are not limited to, the following:

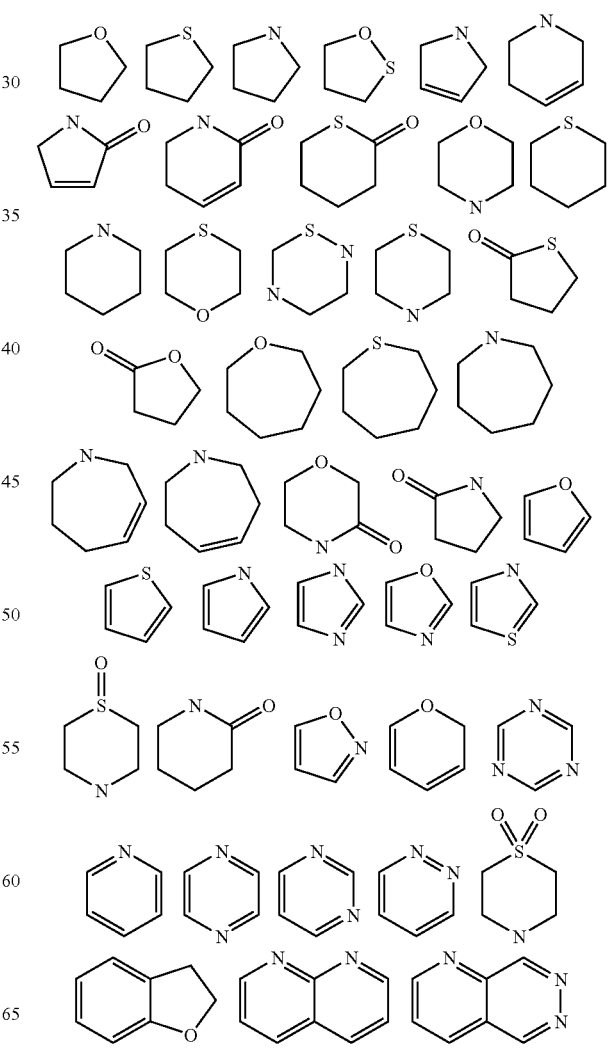

-continued

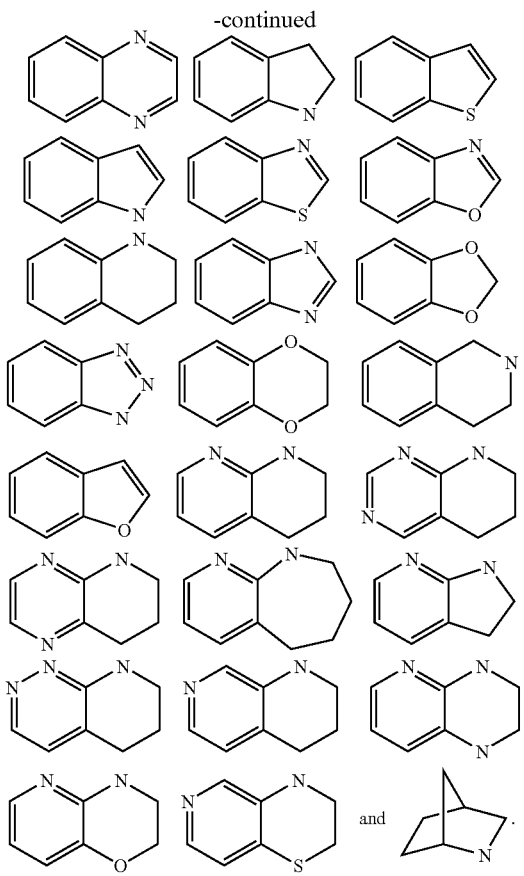

"Available nitrogen atoms" are those nitrogen atoms that are part of a heterocycle and are joined by two single bonds (e.g. piperidine), leaving an external bond available for substitution by, for example, H or $CH_3$.

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzot- riazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

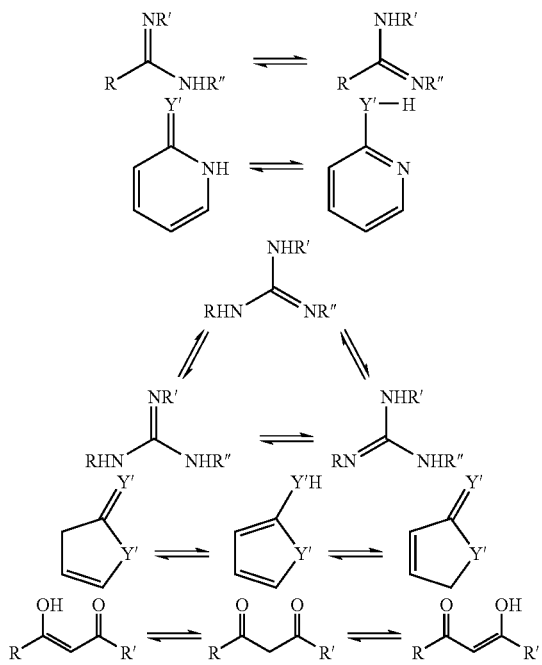

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

EXPERIMENTAL

Unless otherwise noted, all materials were obtained from commercial suppliers and used without further purification. All parts are by weight and temperatures are in degrees centigrade unless otherwise indicated. All microwave assisted reactions were conducted with a Smith Synthesizer from Personal Chemistry, Uppsala, Sweden. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography (HPLC). Chiral HPLC separations were conducted with a Chirobiotic TAG column from Advanced Separation Technologies Inc. Unless otherwise stated, reactions were run at room temperature.

The following abbreviations are used:

| | |
|---|---|
| DMSO | dimethyl sulfoxide |
| DMF | N,N-dimethylformamide |
| THF | tetrahydrofuran |
| Et$_2$O | diethyl ether |
| EtOAc | ethyl acetate |
| MeOH | methyl alcohol |
| EtOH | ethyl alcohol |
| MeCN | acetonitrile |
| MeI | iodomethane |
| NMP | 1-methyl-2-pyrrolidinone |
| DCM | dichloromethane |
| TFA | trifluoroacetic acid |
| MP-carbonate | macroporous polystyrene anion-exchange resin that is a resin bound equivalent of tetraalkylammonium carbonate. |
| sat. | saturated |
| h | hour |
| min | minutes |

EXAMPLE 1

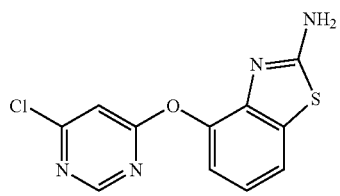

(a) 4-(6-Chloro-pyrimidin-4-yloxy)-benzothiazol-2-ylamine. To a 100-mL, round-bottomed flask containing 4,6-dichloro-pyrimidine (9.0 g, 60 mmol, Aldrich) and 2-amino-benzothiazol-4-ol (5.0 g, 30 mmol, CarboGen) was added potassium carbonate (4.1 g, 30 mmol, Aldrich) and dimethylsulfoxide (10 mL). The reaction mixture was heated at 95° C. with stirring for 4.5 h, and at room temperature for 16 h. The resulting solid was collected by filtration, washed with water (500 mL) and dichloromethane (500 mL), and dried in vacuo to obtain the title compound as a yellow solid.

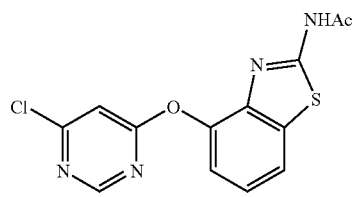

(b) N-[4-(6-Chloro-pyrimidin-4-yloxy)-benzothiazol-2-yl]-acetamide. A mixture of 4-(6-chloro-pyrimidin-4-yloxy)-benzothiazol-2-ylamine, Example 1(a), (4.0 g, 14 mmol), toluene (10 mL) and acetic anhydride (4.1 mL, 43 mmol, Aldrich) was heated at 85° C. with stirring for 2 h and then stirred at room temperature for 16 h. The solvent was evaporated under reduced pressure, and the resulting orange solid was suspended in dichloromethane, collected by filtration and dried under vacuo to obtain the title compound as an off-white solid. M.p: 268-275° C. MS (ESI, pos. ion.) m/z: 321 (M+1).

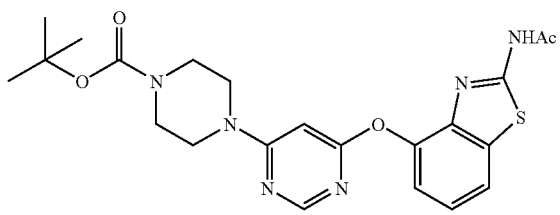

(c) 4-[6-(2-Acetylamino-benzothiazol-4-yloxy)-pyrimidin-4-yl]-piperazine-1-carboxylic acid tert-butyl ester. To a mixture of N-[4-(6-chloro-pyrimidin-4-yloxy)-benzothiazol-2-yl]-acetamide, Example 1(b), (1.5 g, 4.7 mmol) and piperazine-1-carboxylic acid tert-butyl ester (1.7 g, 9.4 mmol, Fluka) was added DMF (6 mL) and potassium carbonate (2.6 g, 18.8 mmol). The reaction mixture was heated at 80° C. with stirring for 1 h, left to reach room temperature, and diluted with water (100 mL). The green precipitate was filtered, washed with methanol, and dried in vacuo to give the title compound. MS (ESI, pos. ion.) m/z: 471 (M+1).

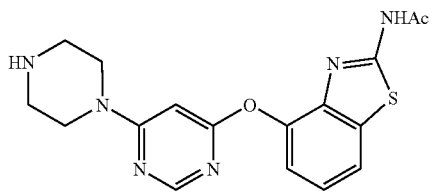

(d) N-[4-(6-piperazin-1-yl-pyrimidin-4-yloxy)-benzothiazol-2-yl]-acetamide. To a suspension of 4-[6-(2-acetylamino-benzothiazol-4-yloxy)-pyrimidin-4-yl]-piperazine-1-carboxylic acid tert-butyl ester, Example 1 (c), (0.45 g, 0.96 mmol) in dichloromethane (60 mL) was added TFA (15 mL, 195 mmol, Aldrich) with stirring at 0° C. The reaction mixture was stirred at room temperature for 18 h, quenched with sat. solution of NaHCO$_3$, and extracted with CH$_2$Cl$_2$ (2×100 mL). The combined organic extracts were dried over Na$_2$SO$_4$, filtered, and concentrated in vacuo. The solid white residue was suspended in MeOH, filtered and dried in vacuo to give the title compound. M.p: 250.3-255.8° C. MS (ESI, pos. ion.) m/z: 471 (M+1).

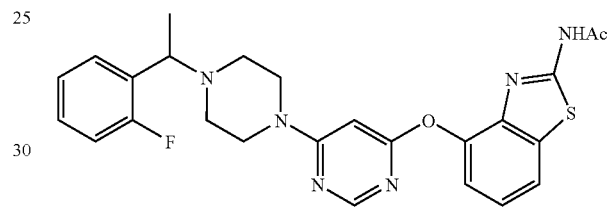

(e) N-[4-(6-{4-[(1S,1R)-1-(2-Fluoro-phenyl)-ethyl]-piperazin-1-yl}-pyrimidin-4-yloxy)-benzothiazol-2-yl]-acetamide. A solution of titanium(IV) isopropoxide (0.14 mL, 4.48 mmol, Aldrich), N-[4-(6-piperazin-1-yl-pyrimidin-4-yloxy)-benzothiazol-2-yl]-acetamide, Example 1(d), (0.06 g, 0.16 mmol), and 2'-fluoro-acetophenone (0.03 mL, 0.24 mmol, Aldrich) in THF (0.6 mL) was heated at 75° C. with stirring for 16 h. The reaction mixture was cooled to −48° C. and diluted with THF (3 mL). Sodium borohydride (0.02 g, 0.48 mmol) was added, and the stirred reaction mixture was allowed to warm to room temperature with stirring over 5 h. To the mixture was added MeOH (2 mL) dropwise, and aqueous NaOH (1N, 50 mL). The product was extracted with ethyl acetate (2×50 mL). The combined extracts were dried over Na$_2$SO$_4$, filtered, and concentrated in vacuo. The residue was purified by silica gel column chromatography (gradient: 0-5% MeOH/CH$_2$Cl$_2$) to give the title compound as a pale-yellow solid. M.p: 202.6-204.3° C. MS (ESI, pos. ion.) m/z: 493.2 (M+1).

EXAMPLE 2

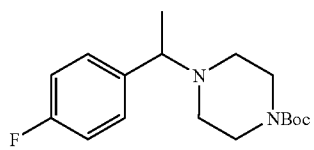

(a) 4-[(1S,1R)-1-(4-Fluoro-phenyl)-ethyl]-piperazine-1-carboxylic acid tert-butyl ester. To a solution of piperazine-1-carboxylic acid tert-butyl ester (0.39 g, 2.2 mmol, Fluka) and 4-fluoro-acetophenone (0.39 mL, 3.3 mmol, Aldrich)

in THF (2 mL) was added titanium(IV) isopropoxide (1.9 mL, 6.6 mmol, Aldrich) and the reaction mixture was stirred at 75° C. for 18 h under nitrogen atmosphere. The mixture was cooled to −48° C., treated with NaBH(OAc)$_3$ (1.23 g, 6.44 mmol, Aldrich) and methanol (1 mL) and allowed to warm to room temperature over 3.5 h. The reaction mixture was diluted with EtOAc (100 mL) and washed with aqueous NaOH (1N, 3×100 mL). The organic layer was separated, dried over Na$_2$SO$_4$, filtered, and concentrated in vacuo. The residue was purified by silica gel column chromatography (gradient: 0-4% MeOH/CH$_2$Cl$_2$) to give the title compound as a yellow oil. MS (ESI, pos. ion.) m/z: 309.2 (M+1).

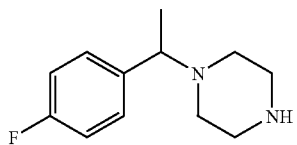

(b) 1-[(1S,1R)-1-(4-Fluoro-phenyl)-ethyl]-piperazine. To a solution of 4-[(1S,1R)-1-(4-fluoro-phenyl)-ethyl]-piperazine-1-carboxylic acid tert-butyl ester, Example 2(a), (0.42 g, 1.36 mmol) in CH$_2$Cl$_2$ (5 mL) was added TFA (0.5 mL, 6.5 mmol, Aldrich) dropwise with stirring at 0° C. The reaction mixture was stirred at room temperature for 18 h and evaporated under reduced pressure. The residue was dried in vacuo to give the crude title compound, which was used in the next step without purification.

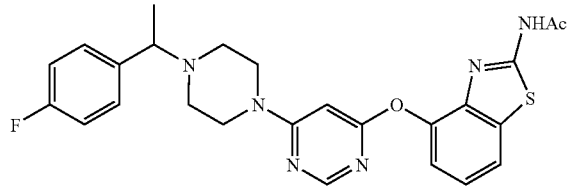

(c) N-[4-(6-{4-[(1S,1R)-1-(4-Fluoro-phenyl)-ethyl]-piperazine1-yl}-pyrimidin-4-yloxy)-benzothiazol-2-yl]-acetamide. To a solution of 1-[(1S,1R)-1-(4-fluoro-phenyl)-ethyl]-piperazine (the cude product from step (b) above) in DMF (4 mL) was added N-[4-(6-chloro-pyrimidin-4-yloxy)-benzothiazol-2-yl]-acetamide, Example 1(b), (0.25 g, 0.76 mmol) and NaHCO$_3$ (0.42 g, 3.04 mmol). The reaction mixture was stirred at 85° C. for 5 h, cooled to room temperature and diluted with water (20 mL). The mixture was extracted with CH$_2$Cl$_2$ (2×25 mL) and the combined organic extracts were dried over Na$_2$SO$_4$, filtered, and concentrated under reduced pressure. The residue was purified by silica gel column chromatography (gradient: 0-5% MeOH/CH$_2$Cl$_2$) to give the title compound as a white amorphous solid. M.p.: 247.3° C. MS (ESI, pos. ion.) m/z: 493 (M+1).

ADDITIONAL EXAMPLES

The following examples were prepared from N-[4-(6-chloro-pyrimidin-4-yloxy)-benzothiazol-2-yl]-acetamide (Example 1(b)) according to the general procedure described for the preparation of Example 2, or with slight modifications thereof:

| Ex. | Structure | M.S. (ESI) m/z | Melt. Point (° C.) |
|---|---|---|---|
| 3 | 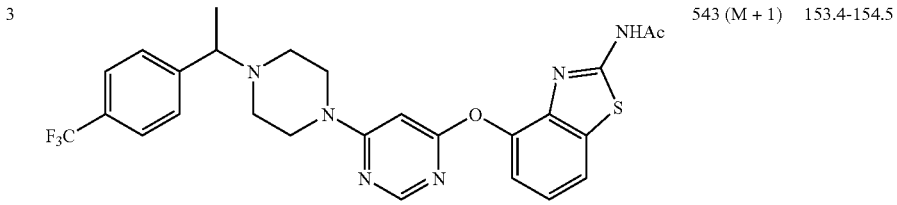 | 543 (M + 1) | 153.4-154.5 |
| 4 | 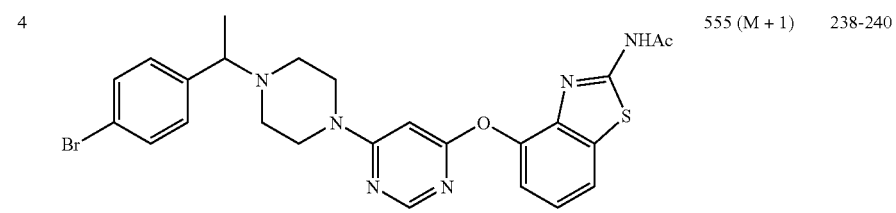 | 555 (M + 1) | 238-240 |

-continued

| Ex. | Structure | M.S. (ESI) m/z | Melt. Point (° C.) |
|---|---|---|---|
| 5 | 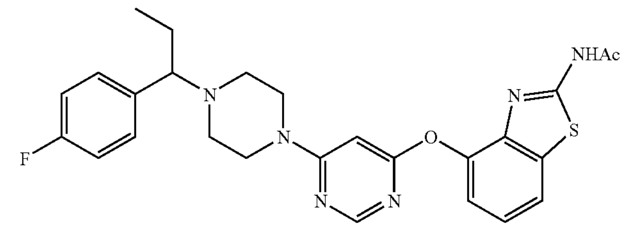 | 507 (M + 1) | 231.1-232.5 |
| 6 | 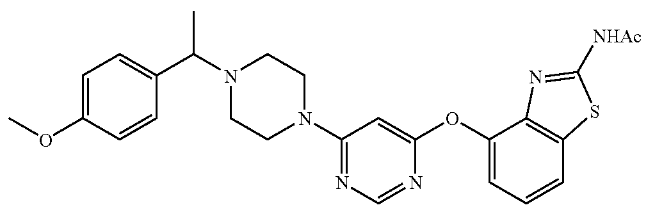 | 505 (M + 1) | 151 |
| 7 | 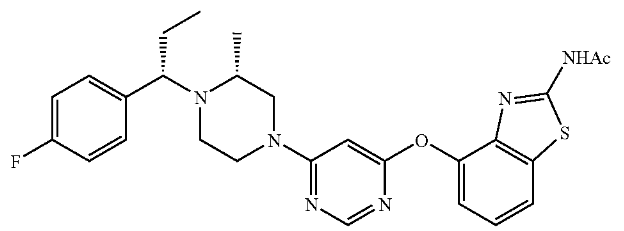 | 521 (M + 1) | 218.9-219.7 |
| 8 | 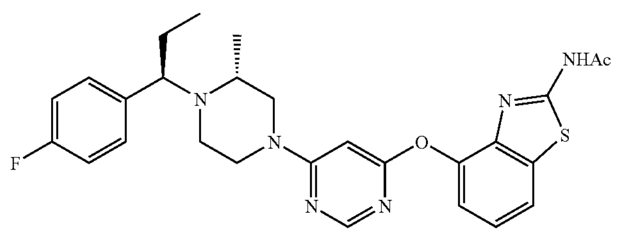 | 521 (M + 1) | 196.6-196.7 |
| 9 | 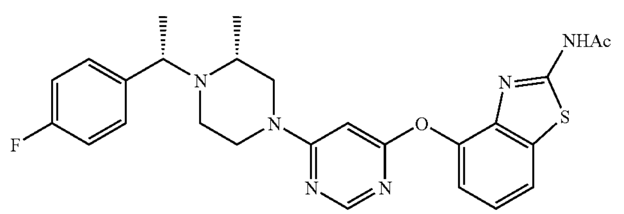 | 507 (M + 1) | 211.6-215.8 |
| 10 | 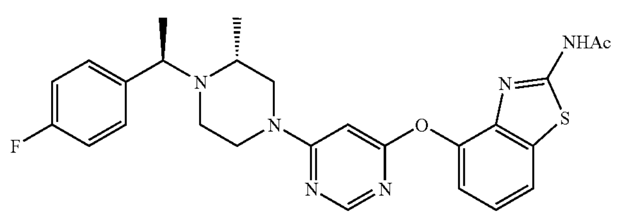 | 507 (M + 1) | 212.2-212.5 |
| 11 | 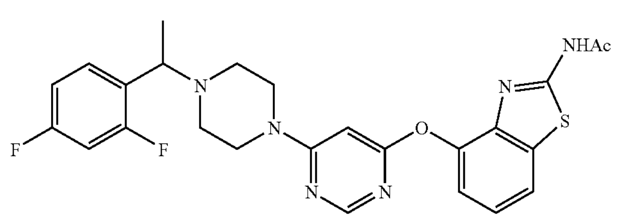 | 511 (M + 1) | 256-268 |

-continued

| Ex. | Structure | M.S. (ESI) m/z | Melt. Point (° C.) |
|---|---|---|---|
| 12 | 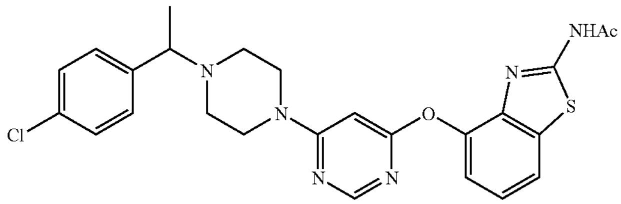 | 509 (M + 1) | 242-250 |
| 13 | 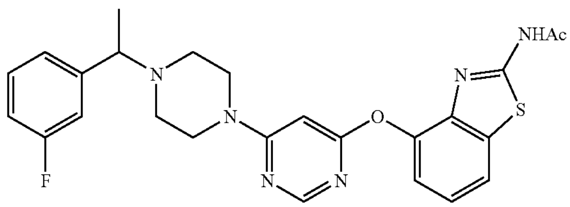 | 493 (M + 1) | 204 |
| 14 | 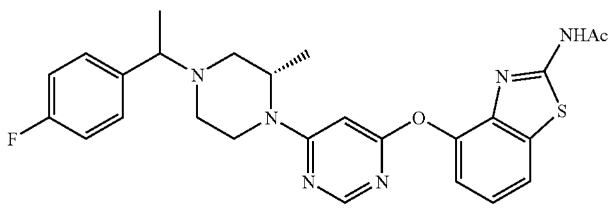 | 507 (M + 1) | 232-234 |
| 15 | 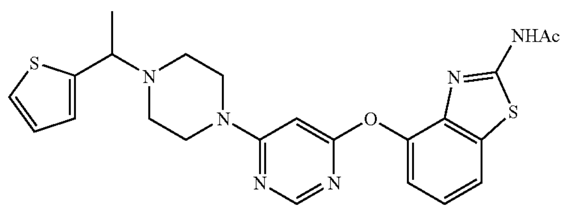 | 481 (M + 1) | 135-140 |
| 16 | 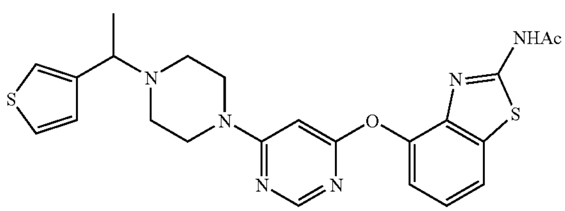 | 481 (M + 1) | 137.5-142.4 |
| 17 | 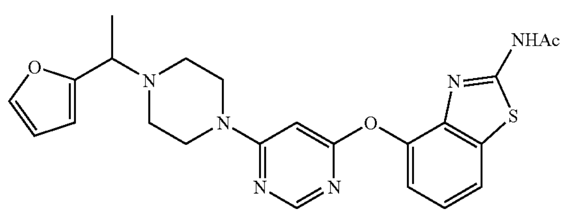 | 465 (M + 1) | 138.6-139.7 |
| 18 | 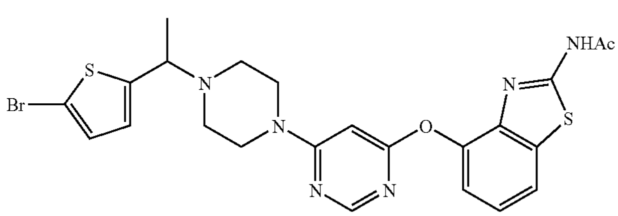 | 561 (M + 1) | 135-141 |

| Ex. | Structure | M.S. (ESI) m/z | Melt. Point (° C.) |
|---|---|---|---|
| 19 | 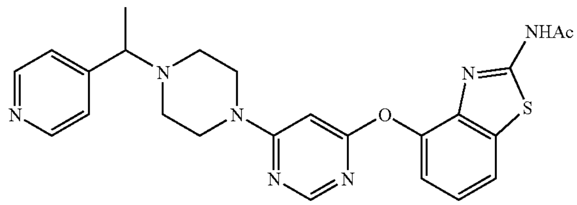 | 474 (M + 1) | 278.1-278.5 |
| 20 | 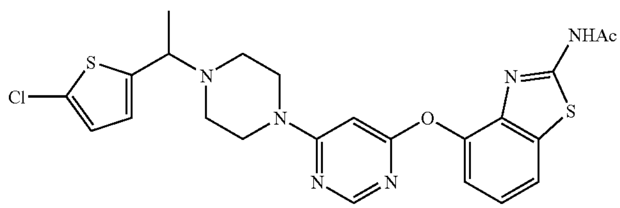 | 515 (M + 1) | 217.4-218.5 |

EXAMPLE 21

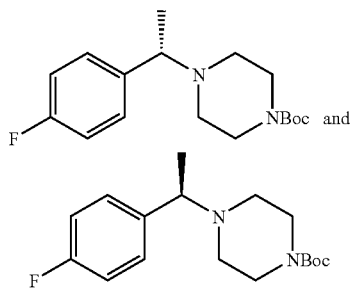

(a) 4-[(1S)-1-(4-Fluoro-phenyl)-ethyl]-piperazine-1-carboxylic acid tert-butyl ester and 4-[(1R)-1-(4-fluoro-phenyl)-ethyl]-piperazine-1-carboxylic acid tert-butyl ester. The two enantiomers of 4-[(1S,1R)-1-(4-fluoro-phenyl)-ethyl]-piperazine-1-carboxylic acid tert-butyl ester, Example 2(a), (1.29 g, 4.2 mmol) were separated by chiral HPLC (100% MeOH/0.08% AcOH/0.02% triethyl amine). The first fraction was collected and concentrated in vacuo to yield 4-[(1S)-1-(4-fluoro-phenyl)-ethyl]-piperazine-1-carboxylic acid tert-butyl ester as a pale-yellow oil. The second fraction was collected and concentrated in vacuo to yield 4-[(1R)-1-(4-fluoro-phenyl)-ethyl]-piperazine-1-carboxylic acid tert-butyl ester as a pale-yellow oil.

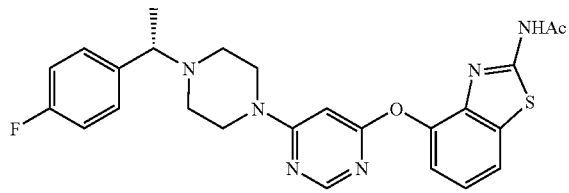

(b) N-[4-(6-{4-[(1S)-1-(4-Fluoro-phenyl)-ethyl]-piperazine 1-yl}-pyrimidin-4-yloxy)-benzothiazol-2-yl]-acetamide.

To a suspension of 4-[1(S)-(4-fluoro-phenyl)-ethyl]-piperazine-1-carboxylic acid tert-butyl ester, Example 21(a), (0.42 g, 1.35 mmol) in CH$_2$Cl$_2$ (2 mL) was added TFA (0.5 mL, 6.5 mmol, Aldrich) with stirring at 0° C. The reaction mixture was stirred at room temperature for 18 h and evaporated under reduced pressure. The residue was dissolved in DMF (3 mL), and to the solution was added N-[4-(6-chloro-pyrimidin-4-yloxy)-benzothiazol-2-yl]-acetamide, Example 1(b), (0.43 g, 1.35 mmol) and cesium carbonate (1.3 g, 4.05 mmol). The reaction mixture was heated at 85° C. with stirring, and the progress of the reaction was monitored by TLC (5% MeOH/CH$_2$Cl$_2$). After completion of the reaction, the mixture was cooled to room temperature and diluted with water (40 mL). The resulting pale-yellow solid was filtered and dried in vacuo. The solid was purified by silica gel column chromatography (gradient: 0-5% MeOH/CH$_2$Cl$_2$) to yield the title compound as an amorphous white solid. M.p.: 243.6-245.7° C. MS (ESI, pos. ion.) m/z: 493 (M+1).

EXAMPLE 22

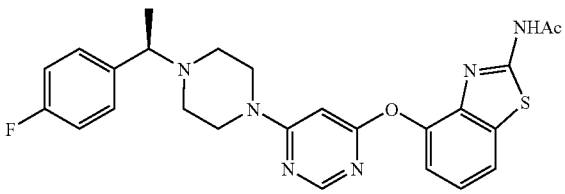

N-[4-(6-{4-[(1R)-1-(4-Fluoro-phenyl)-ethyl]-piperazine1-yl}-pyrimidin-4-yloxy)-benzothiazol-2-yl]-acetamide.
According to the procedures described in Example 21(b), 4-[(1R)-1-(4-fluoro-phenyl)-ethyl]-piperazine-1-carboxylic acid tert-butyl ester, Example 21(a), (0.48 g, 1.6 mmol) and N-[4-(6-chloro-pyrimidin-4-yloxy)-benzothiazol-2-yl]-acetamide, Example 1(b), (0.512 g, 1.6 mmol) provided the title compound as a white solid. M.p.: 243.8-245.9° C. MS (ESI, pos. ion.) m/z: 493 (M+1).

EXAMPLE 23

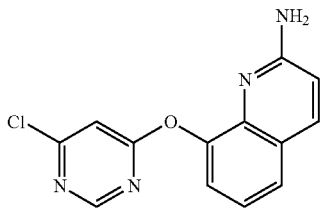

(a) 8-(6-Chloro-pyrimidin-4-yloxy)-quinolin-2-ylamine. To a 50-mL, round-bottomed flask containing 4,6-dichloropyrimidine (0.5 g, 3.4 mmol, Aldrich), 2-amino-8-hydroxyquinoline (0.54 g, 3.4 mmol, Sigma) and DMF (4 mL) was added potassium carbonate (1.9 g, 13.6 mmol). The suspension was stirred for 5 h under nitrogen atmosphere at 75° C. The reaction mixture was cooled to room temperature, diluted with water (50 mL), and extracted with $CH_2Cl_2$ (2×75 mL). The combined extracts were dried over $Na_2SO_4$, filtered, and concentrated in vacuo. The residue was purified by silica gel column chromatography (gradient: 0-50% EtOAc/hexane) to give the title compound as a white solid. M.p.: 185-186° C. MS (ESI, pos. ion.) m/z: 273 (M+1).

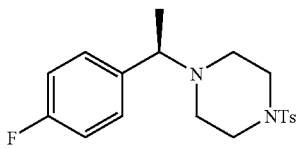

(b) 1-[(1R)-1-(4-Fluoro-phenyl)-ethyl]-4-(toluene-4-sulfonyl)-piperazine. A mixture of N,N-bis(2-chloroethyl)-p-toluenesulfonamide (tech. 90%, 46.8 g, 158 mmol, Lancaster) and (1R)-1-(4-fluorophenyl)ethylamine (20 g, 144 mmol, SynQuest) in N,N-diisopropylethylamine (50 mL) was heated at 125° C. with stirring under a nitrogen atmosphere for 18 h. The reaction mixture was cooled to below 100° C. and a 7/3 mixture of $EtOH/H_2O$ (120 mL) was added slowly with stirring. The mixture was left to reach room temperature and the stirring was continued for 2.5 h. The solid precipitate was filtered, and washed with $H_2O$ (3×50 mL) and hexanes (2×50 mL). The solids were dried in vacuo at 50° C. for 18 h, and stirred in 1:1 mixture of $EtOH/H_2O$ (140 mL) for 75 min. The solid precipitate was filtered, washed with a 1:1 mixture of $EtOH/H_2O$ (40 mL) and a 7:3 mixture of $EtOH/H_2O$ (20 mL), and dried in vacuo at 50° C. for 6 h to give the title compound as an off-white solid. MS (ESI, pos. ion.) m/z: 363 (M+1).

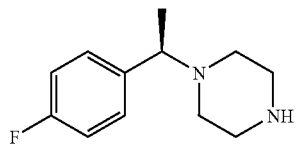

(c) 1-[(1R)-1-(4-Fluoro-phenyl)-ethyl]-piperazine. A mixture of 1-[(1R)-1-(4-fluoro-phenyl)-ethyl]-4-(toluene-4-sulfonyl)-piperazine, Example 23(b), (20 g, 55 mmol), 4-hydroxybenzoic acid (22.9 g, 166 mmol, Aldrich) and HBr solution in AcOH (33 wt %, 200 mL, Aldrich) was stirred at room temperature under nitrogen atmosphere for 48 h. Water (200 mL) was added slowly and the mixture was stirred for 2 h at room temperature. The solid precipitate was filtered and the filter cake was washed with $H_2O$ (2×50 mL). The filtrate and the $H_2O$ washes were combined and extracted with toluene (4×50 mL). The aqueous phase was cooled in an ice bath and treated portionwise with solid KOH (235 g) until pH>10. The aqueous solution was extracted with toluene (3×50 mL) and ethyl acetate (50 mL). The combined organic extracts were washed with brine (100 mL), dried over $MgSO_4$, filtered, and concentrated under reduced pressure. The residue was dried in vacuo to yield the title compound as a pale-brown solid. MS (ESI, pos. ion.) m/z: 209 (M+1).

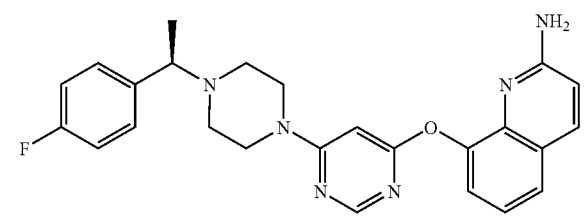

(d) 8-(6-{4-[(1R)-(4-Fluoro-phenyl)-ethyl]-piperazine-1-yl}-pyrimidin-4-yloxy)-quinolin-2-ylamine. To a solution of 1-[(1R)-(4-fluoro-phenyl)-ethyl]-piperazine, Example 23(c), (0.15 g, 0.72 mmol) and 8-(6-chloro-pyrimidin-4-yloxy)-quinolin-2-ylamine, Example 23(a), (0.19 g, 0.72 mmol) in DMF (4 mL) was added potassium carbonate (0.7 g, 2.2 mmol), and the reaction mixture was heated at 85° C. with stirring under nitrogen atmosphere for 8 h. The reaction mixture was allowed to reach room temperature and was diluted with water (20 mL). The resulting off-white solid precipitate was filtered, and dissolved in $CH_2Cl_2$ (20 mL). The solution was washed with water (2×50 mL), dried over $Na_2SO_4$, filtered, and evaporated under reduced pressure. The residue was purified by silica gel column chromatography (gradient: 0-5% $MeOH/CH_2Cl_2$) and then recrystalized in EtOAc/hexane to give the title compound as a white solid. MS (ESI, pos. ion.) m/z: 445 (M+1).

EXAMPLE 24

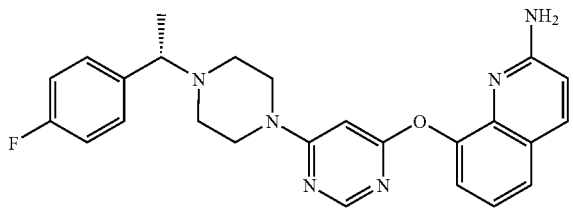

8-(6-{4-[(1S)-(4-Fluoro-phenyl)-ethyl]-piperazine-1-yl}-pyrimidin-4-yloxy)-quinolin-2-ylamine. 1-[(1S)-(4-Fluoro-phenyl)-ethyl]-piperazine (0.15 g, 0.72 mmol, prepared from (1S)-1-(4-fluorophenyl)ethylamine (SynQuest) according steps (b) and (c) of Example 23) was reacted with 8-(6-chloro-pyrimidin-4-yloxy)-quinolin-2-ylamine (0.19 g, 0.72 mmol) under the conditions of Example 23(d) to give the title compound as a white solid. M.p.: 167° C. MS (ESI, pos. ion.) m/z: 445 (M+1).

EXAMPLE 25

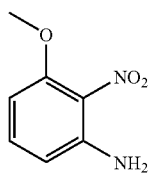

(a) 3-Methoxy-2-nitro-phenylamine. A mixture of 2-amino-3-nitrophenol (25.0 g, 162 mmol, Aldrich) and $K_2CO_3$ (27 g, 195 mmol) in DMF (65 ml) was stirred at room temperature for 1 h. Methyl iodide (12.2 mL, 195 mmol, Aldrich) was added and the reaction was stirred at room temperature for 30 h. The reaction was diluted with $H_2O$ and extracted with EtOAc (3×). The combined organic layers were dried over $Na_2SO_4$, filtered and concentrated in vacuo. The dark-red solid was recrystallized from hexanes to yield the title compound as orange needles. MS (ESI, pos. ion) m/z: 169 (M+1).

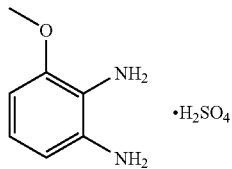

(b) 3-Methoxy-benzene-1,2-diamine sulfate. A mixture of 3-methoxy-2-nitro-phenylamine, Example 25 (a), (4.6 g, 27 mmol), iron powder (10.7 g, 191 mmol, Aldrich), EtOH (130 mL) and $H_2O$ (10 mL) was heated at 50° C. A solution of HCl (12.1 M, 1.7 mL) was added dropwise with stirring. The mixture was heated at reflux for 3 h and allowed to cool to room temperature. After neutralization with NaOH and filtration through Celite®, the solvent was removed in vacuo and the residue was partitioned between $CH_2Cl_2$ and sat. aq. $NaHCO_3$. After extraction with $CH_2Cl_2$ (3×), the combined organic layers were concentrated. The residue was re-dissolved in EtOH (30 mL) and treated with concentrated $H_2SO_4$ until no more precipitate was formed. The resulting solid was removed by filtration, washed with EtOH and dried in vacuo for 20 h at room temperature to give the title compound as an off-white powder. MS (ESI, pos. ion) m/z: 139 (M-$HSO_4^-$).

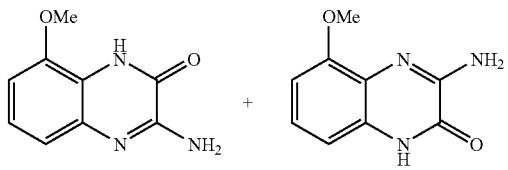

(c) 3-Amino-8-methoxy-1H-quinoxalin-2-one and 3-amino-5-methoxy-1H-quinoxalin-2-one. To a suspension of 3-methoxy-benzene-1,2-diamine sulfate, Example 25(b), (2.36 g, 10 mmol) in EtOH (15 mL) and $H_2O$ (1 mL) was added $NaHCO_3$ (1.68 g, 20 mmol, J T Baker). When gas evolution was complete, ethoxy-imino-acetic acid ethyl ester (1.6 g, 11 mmol, prepared according to *J. Chem. Soc. Perkin. Trans.* 1, 1999, 1789) was added and the mixture was stirred at room temperature for 16 h. The reaction was diluted with sat. aq. $NaHCO_3$ and extracted with 25% i-PrOH($CHCl_3$ (5×). The combined organic layers were dried over $Na_2SO_4$, filtered, and concentrated in vacuo. Purification by silica gel column chromatography (gradient: 0-5% MeOH/$CH_2Cl_2$) afforded 3-amino-8-methoxy-1H-quinoxalin-2-one as a light-brown powder [MS (ESI, pos. ion) m/z: 192 (M+1)] and 3-amino-5-methoxy-1H-quinoxalin-2-one as a light-brown powder [MS (ESI, pos. ion) m/z: 192 (M+1)].

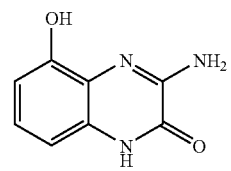

(d) 3-Amino-5-hydroxy-1H-quinoxalin-2-one. To a suspension of 3-amino-5-methoxy-1H-quinoxalin-2-one, Example 25(c), (0.47 g, 2.5 mmol) in benzene (25 mL) was added $AlCl_3$ (0.97 g, 7.4 mmol, Aldrich) and the mixture was heated to reflux with stirring for 2 h. The reaction mixture was cooled to room temperature and quenched by the careful addition of satd aq. $NaHCO_3$. The resulting mixture was extracted with 25% i-PrOH/$CHCl_3$ (5×). The combined organic extracts were dried over $Na_2SO_4$, filtered, and concentrated in vacuo to afford a brown powder. MS (ESI, pos. ion) m/z: 178 (M+1).

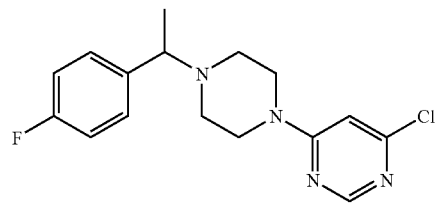

(e) 4-Chloro-6-{4-[(1S,1R)-1-(4-fluoro-phenyl)-ethyl]-piperazin-1-yl}-pyrimidine. 1-[(1S,1R)-1-(4-Fluoro-phenyl)-ethyl]-piperazine, Example 2(b), (0.87 g, 4.2 mmol) was reacted with 4,6-dichloropyrimidine (0.7 g, 4.6 mmol, Aldrich) under the conditions described in Example 1(c) to give the title compound as a white solid. MS (ESI, pos. ion.) m/z: 321 (M+1).

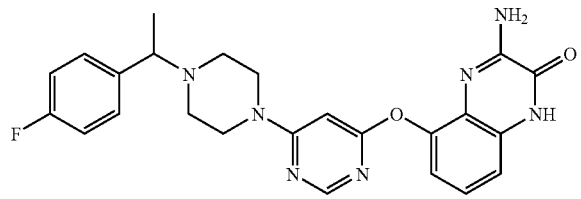

(f) 3-Amino-5-(6-{4-[(1S,1R)-1-(4-fluoro-phenyl)-ethyl]-piperazin-1-yl}-pyrimidin-4-yloxy)-1H-quinoxalin-2-one. A mixture of 4-chloro-6-{4-[(1S,1R)-1-(4-fluoro-phenyl)-ethyl]-piperazin-1-yl}-pyrimidine, Example 25(e), (0.18 g, 0.56 mmol), 3-amino-5-hydroxy-1H-quinoxalin-2-one, Example 25(d), (0.10 g, 0.56 mmol) and $K_2CO_3$ (0.12 g, 0.85 mmol, Aldrich) in DMF (5 mL) was heated at 80° C. with stirring for 24 h. After cooling to room temperature, $Cs_2CO_3$ (0.36 g, 1.1 mmol, Aldrich) was added, and the mixture was stirred at 90° C. for 96 h. The mixture was cooled to room temperature, diluted with $H_2O$ and extracted with 25% i-PrOH/$CHCl_3$ (5×). The combined organic extracts were dried over $Na_2SO_4$, filtered, and concentrated in vacuo. The residue was purified by silica gel column chromatography (gradient: 0-5% (2M NH$_3$ in MeOH)/CH$_2$Cl$_2$) to give the title compounds as a white amorphous powder. MS (ESI, pos. ion) m/z: 462.2 (M+1).

EXAMPLE 26

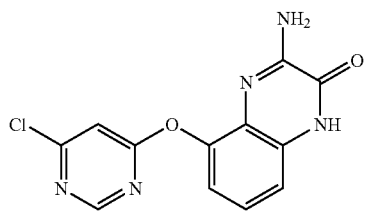

(a) 3-Amino-5-(6-chloro-pyrimidin-4-ylmethyl)-1H-quinoxalin-2-one. To a solution of 4,6-dichloropyrimidine (0.30 g, 2.0 mmol, Aldrich) and 3-amino-5-hydroxy-1H-quinoxalin-2-one, Example 25(d), (0.35 g, 2.0 mmol) in DMF (10 mL) was added K$_2$CO$_3$ (0.33 g, 2.4 mmol, Aldrich) and the mixture was stirred at room temperature for 24 h. The reaction mixture was diluted with H$_2$O and the light-brown solid precipitate was filtered. The filter cake was washed with H$_2$O and air-dried to give the title compound. MS (ESI, pos. ion) m/z: 290.1 (M+1).

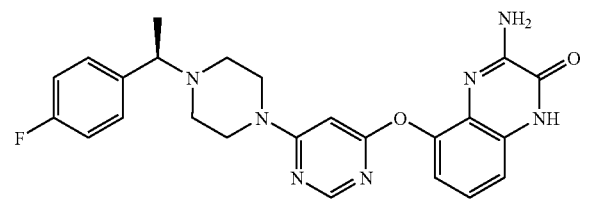

(b) 3-Amino-5-(6-{4-[(1R)-1-(4-fluoro-phenyl)-ethyl]-piperazin-1-yl}-pyrimidin-4-yloxy)-1H-quinoxalin-2-one. A mixture of 3-amino-5-(6-chloro-pyrimidin-4-ylmethyl)-1H-quinoxalin-2-one, Example 26(a), (0.17 g, 0.59 mmol) and 1-[(1R)-1-(4-fluoro-phenyl)-ethyl]-piperazine, Example 23(c), (0.12 g, 0.59 mmol) was dissolved in DMF (5 mL). To the solution was added Cs$_2$CO$_3$ (0.38 g, 1.2 mmol) and the mixture was heated at 85° C. with stirring for 8 h. The reaction mixture was cooled to room temperature, diluted with H$_2$O, and the solid precipitate was filtered. The filter cake was washed with H$_2$O and purified by silica gel column chromatography (gradient: 0-5% (2M NH$_3$ in MeOH)/CH$_2$Cl$_2$) to give the title compound as an off-white solid. Mp: 292.2-293.9° C., MS (ESI, pos. ion) m/z: 462.2 (M+1).

EXAMPLE 27

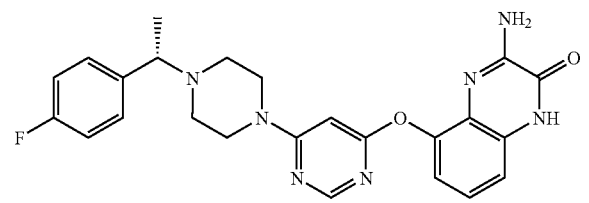

3-Amino-5-(6-{4-[(1S)-1-(4-fluoro-phenyl)-ethyl]-piperazin-1-yl}-pyrimidin-4-yloxy)-1H-quinoxalin-2-one. This material was prepared according to the procedure used in Example 26(b) by reacting 3-amino-5-(6-chloro-pyrimidin-4-ylmethyl)-1H-quinoxalin-2-one, Example 26(a), (0.20 g, 0.69 mmol) with 1-[(1S)-1-(4-fluoro-phenyl)-ethyl]-piperazine (0.14 g, 0.69 mmol, prepared from (1S)-1-(4-fluorophenyl)ethanamine (SynQuest) according to steps (b) and (c) of Example 23). The title compound was isolated as an off-white solid. Mp: 294.5-295.3° C., MS (ESI, pos. ion) m/z: 462.2 (M+1).

EXAMPLE 28

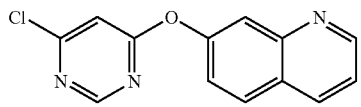

(a) 7-(6-Chloropyrimidin-4-yloxy)quinoline. A mixture of 7-hydroxyquinoline (0.387 g, 2.67 mmol, Acros), 4,6-dichloropyrimidine (0.398 g, 2.67 mmol, Aldrich) and potassium carbonate (0.369 g, 2.67 mmol, Aldrich) in DMF (3 mL) was stirred at room temperature for 16 h and then heated in a microwave synthesizer at 100° C. for 5 min. The reaction mixture was allowed to cool to room temperature and was filtered. The filter cake was washed with methanol (5 mL) and the filtrate was concentrated under reduced pressure. The reddish-brown residue was purified by silica gel column chromatography (gradient: 0-50% EtOAc/hexane) to afford the title compound as pale-yellow amorphous solid. MS (ESI, pos. ion.) m/z: 258 (M+1).

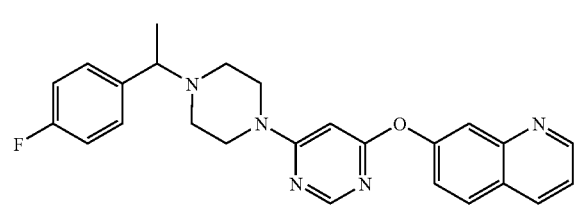

(b) 7-(6-(4-(1-(4-Fluorophenyl)ethyl)piperazin-1-yl)pyrimidin-4-yloxy)quinoline. A solution of 7-(6-chloropyrimidin-4-yloxy)quinoline from step (a) above (0.045 g, 0.18 mmol) and 1-(1-(4-fluorophenyl)ethyl)piperazine, Example 2(b), (0.036 g, 0.17 mmol,) in DMSO (0.5 mL) was heated in a microwave synthesizer at 170° C. for 5 min. The reaction mixture was allowed to cool to room temperature and evaporated under reduced pressure. The residue was purified by preparative HPLC [gradient: 10-90% MeCN/(0.1% TFA in MeCN/H$_2$O)] to give the desired product as a TFA salt. The salt was dissolved in DCM (25 mL) and neutralized with sat. NaHCO$_3$ (5 mL). The DCM layer was separated, dried over anhydrous sodium sulfate, and filtered. The filtrate was evaporated and the residue was dried under vacuo to give the title compound as light-yellow oil. MS (ESI, pos. ion.) m/z: 430 (M+1).

EXAMPLE 29

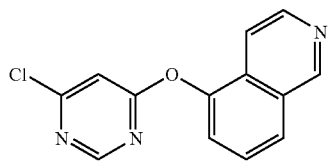

(a) 5-(6-Chloropyrimidin-4-yloxy)isoquinoline. 5-Hydroxy-isoquinoline (0.431 g, 2.97 mmol, Aldrich) was reacted with 4,6-dichloropyrimidine (0.442 g, 2.97 mmol, Aldrich) under the conditions of Example 28(a) to give the title compound as pale-yellow amorphous solid. MS (ESI, pos. ion.) m/z: 258 (M+1).

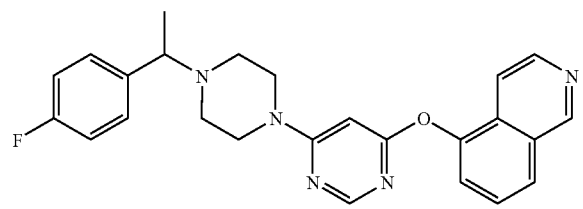

(b) 5-(6-(4-(1-(4-Fluorophenyl)ethyl)piperazin-1-yl)pyrimidin-4-yloxy)isoquinoline. 5-(6-Chloropyrimidin-4-yloxy)isoquinoline from step (a) above (0.213 g, 0.83 mmol) was reacted with 1-(1-(4-fluorophenyl)ethyl)piperazine, Example 2(b), (0.175 g, 0.84 mmol) under the conditions of Example 28(b) to give the title compound as white amorphous solid. MS (ESI, pos. ion.) m/z: 430 (M+1).

EXAMPLE 30

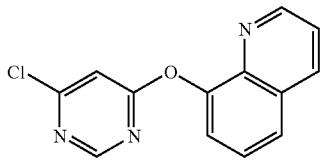

(a) 8-(6-Chloropyrimidin-4-yloxy)quinoline. 8-Hydroxyquinoline (0.435 g, 3.00 mmol, Sigma) was reacted with 4,6-dichloropyrimidine (0.449 g, 3.01 mmol, Aldrich) under the conditions of Example 28(a) to give the title compound as pale-yellow amorphous solid. MS (ESI, pos. ion.) m/z: 258 (M+1).

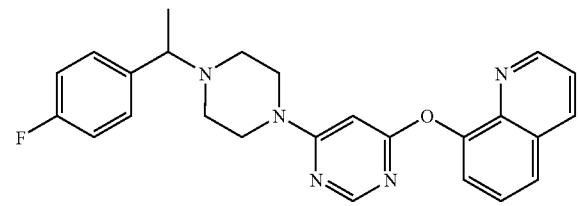

(b) 8-(6-(4-(1-(4-Fluorophenyl)ethyl)piperazin-1-yl)pyrimidin-4-yloxy)quinoline. 8-(6-Chloropyrimidin-4-yloxy)quinoline from step (a) above (0.130 g, 0.51 mmol) was reacted with 1-(1-(4-fluorophenyl)ethyl)piperazine, Example 2(b), (0.105 g, 0.50 mmol) under the conditions of Example 28(b) to give the title compound as off-white oil. MS (ESI, pos. ion.) m/z: 430 (M+1).

EXAMPLE 31

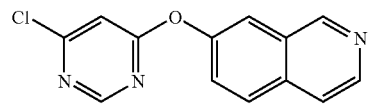

(a) 7-(6-Chloropyrimidin-4-yloxy)isoquinoline. 7-Hydroxy-isoquinoline (0.286 g, 1.97 mmol, Lancaster) was reacted with 4,6-dichloropyrimidine (0.295 g, 1.98 mmol, Aldrich) under the conditions of Example 28(a) to give the title compound as pale-yellow amorphous solid. MS (ESI, pos. ion.) m/z: 258 (M+1).

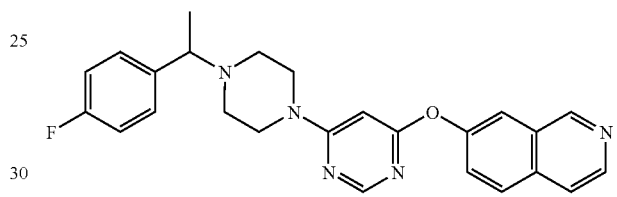

(b) 7-(6-(4-(1-(4-Fluorophenyl)ethyl)piperazin-1-yl)pyrimidin-4-yloxy)isoquinoline. A mixture of 7-(6-chloropyrimidin-4-yloxy)isoquinoline from step (a) above (0.038 g, 0.15 mmol), 1-(1-(4-fluorophenyl)ethyl)piperazine, Example 2(b), (0.031 g, 0.15 mmol) and diisopropylethylamine (0.050 mL, 0.29 mmol) in EtOH (0.75 mL) was heated in a microwave synthesizer at 165° C. for 6 min. The reaction mixture was cooled to room temperature and evaporated under reduced pressure. The residue was purified by preparative HPLC [gradient: 10-90% MeCN/(0.1% TFA in MeCN/H$_2$O)] to give the desired product as a TFA salt. The salt was dissolved in DCM (25 mL) and neutralized with sat. NaHCO$_3$ (5 mL). The DCM layer was separated, dried over anhydrous sodium sulfate, and filtered. The filtrate was evaporated and the residue was dried under vacuo to give the title compound as off-white oil. MS (ESI, pos. ion.) m/z: 430 (M+1).

EXAMPLE 32

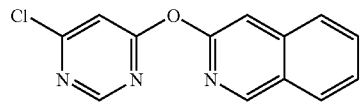

(a) 3-(6-Chloropyrimidin-4-yloxy)isoquinoline. 3-Hydroxy-isoquinoline (0.338 g, 2.33 mmol, Aldrich) was reacted with 4,6-dichloropyrimidine (0.348 g, 2.34 mmol, Aldrich) under the conditions of Example 28(a) to give the title compound as pale-yellow amorphous solid. MS (ESI, pos. ion.) m/z: 258 (M+1).

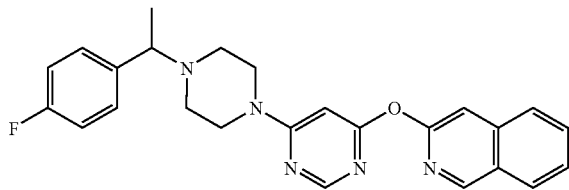

(b) 3-(6-(4-(1-(4-Fluorophenyl)ethyl)piperazin-1-yl)pyrimidin-4-yloxy)isoquinoline. 3-(6-Chloropyrimidin-4-yloxy)isoquinoline from step (a) above (0.070 g, 0.27 mmol) was reacted with 1-(1-(4-fluorophenyl)ethyl)piperazine, Example 2(b), (0.057 g, 0.27 mmol) under the conditions of Example 31(b) to give the title compound as white amorphous solid. MS (ESI, pos. ion.) m/z: 430 (M+1).

EXAMPLE 33

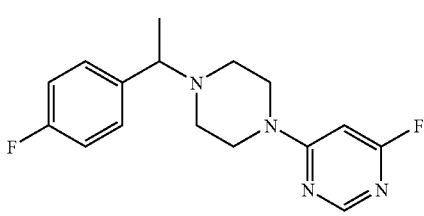

a) 4-Fluoro-6-(4-(1-(4-fluorophenyl)ethyl)piperazin-1-yl)pyrimidine. To a mixture of 1-[(1S,1R)-1-(4-fluoro-phenyl)-ethyl]-piperazine, Example 2(b), (0.50 g, 2.4 mmol) and 4,6-difluoropyrimidine (0.28 mL, 2.4 mmol, ABCR) in DMF (8 mL) was added cesium carbonate (2.3 g, 7.2 mmol) with stirring at 0° C. The reaction mixture was stirred at 0° C. for 20 min, diluted with H$_2$O (20 mL) and extracted with DCM (2×40 mL). The combined organic extracts were washed with H$_2$O (2×40 mL), dried over Na$_2$SO$_4$ and filtered. The filtrate was evaporated and the residue was dried in vacuo to yield the title compound. MS (ESI, pos. ion.) m/z: 305 (M+1)

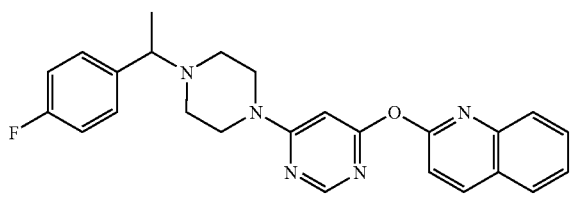

b) 2-(6-(4-(1-(4-Fluorophenyl)ethyl)piperazin-1-yl)pyrimidin-4-yloxy)quinoline. To a solution of 4-fluoro-6-(4-(1-(4-fluorophenyl)ethyl)piperazin-1-yl)pyrimidine from step (a) above (0.178 g, 0.59 mmol) and quinolin-2-ol (0.085 g, 0.59 mmol, Aldrich) in DMSO (2.0 mL) was added 95% sodium hydride (0.027 g, 1.13 mmol, Aldrich). The mixture was stirred at room temperature for 15 min and then heated in a microwave synthesizer at 170° C. for 5 min. The reaction mixture was allowed to cool to room temperature and evaporated under reduced pressure. The residue was purified by preparative HPLC [gradient: 10-90% MeCN/(0.1% TFA in MeCN/H$_2$O)] to give the desired product as a TFA salt. The salt was dissolved in DCM (25 mL) and neutralized with sat. NaHCO$_3$ (5 mL). The DCM layer was separated, dried over anhydrous sodium sulfate, and filtered. The filtrate was evaporated and the residue was dried in vacuo to give the title compound as off-white oil. MS (ESI, pos. ion.) m/z: 430 (M+1).

EXAMPLE 34

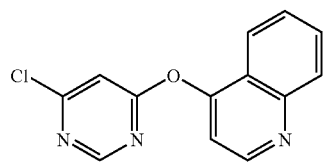

(a) 4-(6-Chloropyrimidin-4-yloxy)quinoline. A mixture of 4-hydroxyquinoline (0.435 g, 2.99 mmol, Aldrich), 4,6-dichloropyrimidine (0.453 g, 3.04 mmol, Aldrich) and MP-carbonate resin (0.369 g, 2.67 mmol, 2.73 mmol/g, Argonaut) in NMP (2.5 mL) was stirred at room temperature for 2 h and then heated in a microwave synthesizer at 100° C. for 5 min. The reaction mixture was cooled to room temperature and the resin was removed by filtration. The filter cake was washed with methanol (10 mL) and the combined filtrate was concentrated under reduced pressure. The reddish-brown residue was purified by silica gel column chromatography (gradient: 0-5% MeOH/DCM) to afford the title compound as pale-yellow amorphous solid. MS (ESI, pos. ion.) m/z: 258 (M+1).

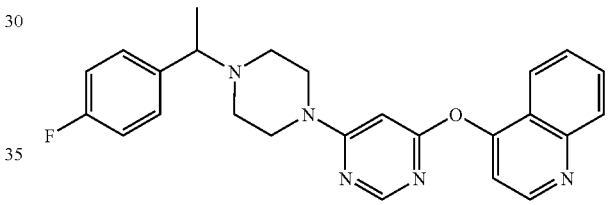

(b) 4-(6-(4-(1-(4-Fluorophenyl)ethyl)piperazin-1-yl)pyrimidin-4-yloxy)quinoline. 4-(6-Chloropyrimidin-4-yloxy)quinoline from step (a) above (0.060 g, 0.23 mmol) was reacted with 1-(1-(4-fluorophenyl)ethyl)piperazine, Example 2(b), (0.049 g, 0.24 mmol) under the conditions of Example 31(b) to give the title compound as off-white oil. MS (ESI, pos. ion.) m/z: 430 (M+1).

EXAMPLE 35

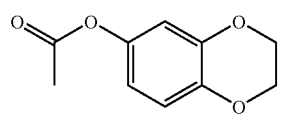

(a) 2,3-Dihydrobenzo[b][1,4]dioxin-6-yl acetate. A solution of 1-(2,3-dihydrobenzo-[b][1,4]dioxin-6-yl)ethanone (1.548 g, 8.69 mmol, Aldrich) and 3-chloroperoxybenzoic acid (4.35 g, 19.41 mmol, 77% by weight, Aldrich) in DCM (55 mL) was heated to 65° C. for 17.5 h in an oil-bath. The reaction mixture was allowed to cool to room temperature and diluted with DCM (150 mL) and water (50 mL). The DCM layer was separated, washed with saturated NaHCO$_3$ (100 mL) and brine (25 mL), dried over anhydrous sodium sulfate, and filtered. The filtrate was evaporated and the residue was dried in vacuo to give the title compound as an amorphous solid. MS (ESI, pos. ion.) m/z: 195 (M+1).

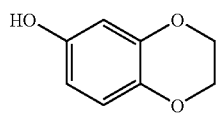

(b) 2,3-Dihydrobenzo[b][1,4]dioxin-6-ol. A solution of 2,3-dihydrobenzo[b][1,4]dioxin-6-yl acetate from step (a) above (1.65 g, 10.84 mmol, Aldrich) in MeOH (80 mL) was stirred with 2.5 N NaOH (120 mL) at room temperature for 21 h. The MeOH was evaporated under reduced pressure and the residue was diluted with EtOAc (200 mL). The EtOAc layer was separated, dried over anhydrous sodium sulfate, and filtered. The filtrate was evaporated and the residue was dried under vacuo to give a reddish-brown solid. The solid was suspended in MeOH (10 mL) and filtered. The filter cake was dried in vacuo to give the title compound as an amorphous solid. MS (ESI, pos. ion.) m/z: 153 (M+1).

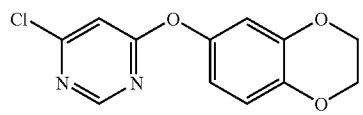

(c) 4-Chloro-6-(2,3-dihydrobenzo[b][1,4]dioxin-6-yloxy) pyrimidine. A mixture of 2,3-dihydrobenzo[b][1,4]dioxin-6-ol from step (b) above (0.500 g, 3.29 mmol), 4,6-dichloropyrimidine (0.417 g, 2.80 mmol, Aldrich) and MP-carbonate resin (1.41 g, 4.09 mmol, 2.9 mmol/g, Argonaut) in NMP (3.0 mL) was stirred at room temperature for 2 h and then heated in a microwave synthesizer at 110° C. for 6 min. The reaction mixture was cooled to room temperature and the resin was removed by filtration. The filter cake was washed with methanol (10 mL) and the filtrate was evaporated under reduced pressure. The reddish-brown residue was purified by silica gel column chromatography (gradient: 0-5% MeOH/DCM) to afford the title compound as pale-yellow amorphous solid. MS (ESI, pos. ion.) m/z: 265 (M+1).

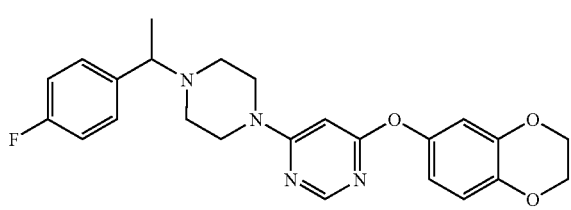

(d) 4-(2,3-Dihydrobenzo[b][1,4]dioxin-6-yloxy)-6-(4-(1-(4-fluorophenyl)ethyl)piperazin-1-yl)pyrimidine. 4-Chloro-6-(2,3-dihydrobenzo[b][1,4]dioxin-6-yloxy)pyrimidine from step (c) above (0.156 g, 0.59 mmol) was reacted with 1-(1-(4-fluorophenyl)ethyl)piperazine, Example 2(b), (0.123 g, 0.59 mmol) under the conditions of Example 31(b) to give the title compound as off-white oil. MS (ESI, pos. ion.) m/z: 437 (M+1).

EXAMPLE 36

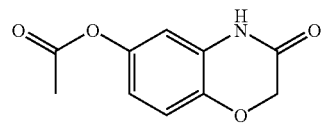

(a) 3-Oxo-3,4-dihydro-2H-benzo[b][1,4]oxazin-6-yl acetate. 6-Acetyl-2H-benzo-[b][1,4]oxazin-3(4H)-one (1.133 g, 5.93 mmol, Aldrich) was treated with 3-chloro-peroxybenzoic acid (3.15 g, 14.06 mmol, 77% by weight, Aldrich) under the conditions of Example 35(a) to give the title compound as an amorphous solid. MS (ESI, pos. ion.) m/z: 208 (M+1).

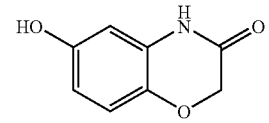

(b) 6-Hydroxy-2H-benzo[b][1,4]oxazin-3(4H)-one. 3-Oxo-3,4-dihydro-2H-benzo-[b][1,4]oxazin-6-yl acetate from step (a) above (1.21 g, 5.84 mmol, Aldrich) in MeOH (80 mL) was reacted with 2.5 N NaOH (120 mL) under the conditions of Example 35(b) to give the title compound as an amorphous solid. MS (ESI, pos. ion.) m/z: 166 (M+1).

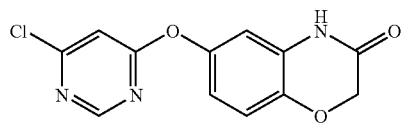

(c) 6-(6-Chloropyrimidin-4-yloxy)-2H-benzo[b][1,4]oxazin-3(4H)-one. 6-Hydroxy-2H-benzo[b][1,4]oxazin-3 (4H)-one from step (b) above (0.325 g, 1.97 mmol) was reacted with 4,6-dichloropyrimidine (0.264 g, 1.77 mmol, Aldrich) under the conditions of Example 35(c) to give the title compound as pale-yellow amorphous solid. MS (ESI, pos. ion.) m/z: 278 (M+1).

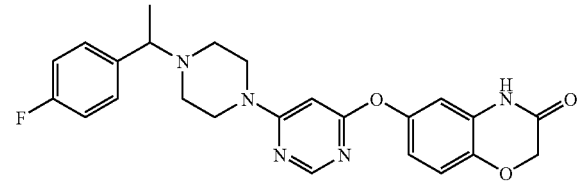

(d) 6-(6-(4-(1-(4-Fluorophenyl)ethyl)piperazin-1-yl)pyrimidin-4-yloxy)-2H-benzo[b][1,4]oxazin-3(4H)-one. 6-(6-Chloropyrimidin-4-yloxy)-2H-benzo-[b][1,4]oxazin-3 (4H)-one from step (c) above (0.085 g, 0.31 mmol) was reacted with 1-(1-(4-fluorophenyl)ethyl)piperazine, Example 2(b), (0.067 g, 0.32 mmol) under the conditions of Example 31(b) to give the title compound as off-white oil. MS (ESI, pos. ion.) m/z: 450 (M+1).

EXAMPLE 37

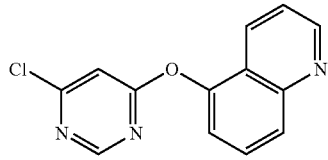

(a) 5-(6-Chloropyrimidin-4-yloxy)quinoline. 5-Hydroxyquinoline (0.292 g, 2.01 mmol, Aldrich) was reacted with 4,6-dichloropyrimidine (0.3 g, 2.01 mmol, Aldrich) under the conditions of Example 34(a) to give the title compound as pale-yellow amorphous solid. MS (ESI, pos. ion.) m/z: 258 (M+1).

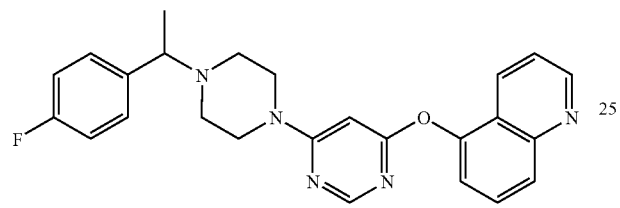

(b) 5-(6-(4-(1-(4-Fluorophenyl)ethyl)piperazin-1-yl)pyrimidin-4-yloxy)quinoline. A mixture of 5-(6-chloropyrimidin-4-yloxy)quinoline from step (a) above (0.130 g, 0.51 mmol), 1-(1-(4-fluorophenyl)ethyl)piperazine, Example 2(b), (0.107 g, 0.51 mmol) and PS-DIEA resin (0.40 g, 1.49 mmol, 3.72 mmol/g, Argonaut) in EtOH (4.0 mL) was stirred at room temperature for 2 h and then heated in a microwave synthesizer at 160° C. for 6 min. The reaction mixture was allowed to cool to room temperature and the resin was removed by filtration. The resin was washed with methanol (10 mL) and the combined filtrate was evaporated under reduced pressure. The gummy residue was dissolved in MeOH (2.5 mL) and purified by preparative HPLC [gradient: 10-90% MeCN/(0.1% TFA in MeCN/H$_2$O)] to give the desired product as a TFA salt. The salt was dissolved in DCM (25 mL) and neutralized with sat. NaHCO$_3$ (5 mL). The DCM layer was separated, dried over anhydrous sodium sulfate, and filtered. The filtrate was evaporated and the residue was dried in vacuo to give the title compound as off-white oil. MS (ESI, pos. ion.) m/z: 430 (M+1).

EXAMPLE 38

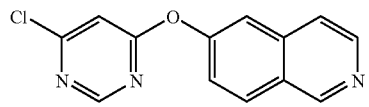

(a) 6-(6-Chloropyrimidin-4-yloxy)isoquinoline. 6-Hydroxyisoquinoline (0.294 g, 2.03 mmol, J & W Pharma Lab) was reacted with 4,6-dichloropyrimidine (0.302 g, 2.03 mmol, Aldrich) under the conditions of Example 34(a) to give the title compound as pale-yellow amorphous solid. MS (ESI, pos. ion.) m/z: 258 (M+1).

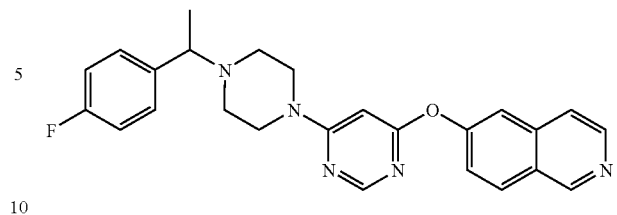

(b) 6-(6-(4-(1-(4-Fluorophenyl)ethyl)piperazin-1-yl)pyrimidin-4-yloxy)isoquinoline. 6-(6-Chloropyrimidin-4-yloxy)isoquinoline from step (a) above (0.136 g, 0.53 mmol) was reacted with 1-(1-(4-fluorophenyl)ethyl)piperazine Example 2(b), (0.112 g, 0.54 mmol) under the conditions of Example 37(b). The crude product was purified by preparative HPLC [gradient 10-90% MeCN (0.1% TFA)/H$_2$O (0.1% TFA)] to give the title compound as off-white oil. MS (ESI, pos. ion.) m/z: 430 (M+1).

EXAMPLE 39

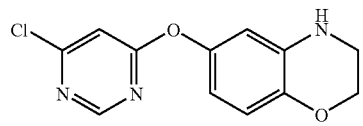

(a) 6-(6-Chloropyrimidin-4-yloxy)-3,4-dihydro-2H-benzo[b][1,4]oxazine. 3,4-Dihydro-2H-benzo[b][1,4]oxazin-6-ol (0.152 g, 1.01 mmol, Matrix) was reacted with 4,6-dichloropyrimidine (0.15 g, 1.01 mmol, Aldrich) under the conditions of Example 34(a) to give the title compound as pale-yellow amorphous solid. MS (ESI, pos. ion.) m/z: 264 (M+1).

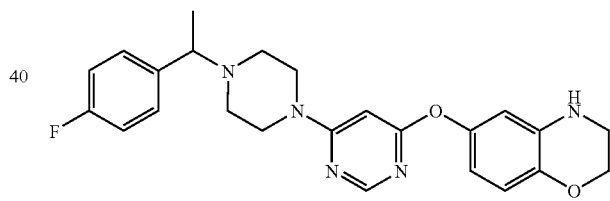

(b) 6-(6-(4-(1-(4-Fluorophenyl)ethyl)piperazin-1-yl)pyrimidin-4-yloxy)-3,4-dihydro-2H-benzo[b][1,4]oxazine. 6-(6-Chloropyrimidin-4-yloxy)-3,4-dihydro-2H-benzo[b][1,4]oxazine from step (a) above (0.043 g, 0.17 mmol) was reacted with 1-(1-(4-fluorophenyl)ethyl)piperazine, Example 2(b), (0.040 g, 0.19 mmol) under the conditions of Example 31(b) to give the title compound as amorphous white solid. MS (ESI, pos. ion.) m/z: 436 (M+1).

EXAMPLE 40

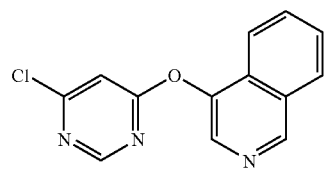

(a) 4-(6-Chloropyrimidin-4-yloxy)isoquinoline. Isoquinolin-4-ol (0.436 g, 3.00 mmol, Monomer Chem) was reacted with 4,6-dichloropyrimidine (0.449 g, 3.01 mmol, Aldrich) under the conditions of Example 34(a) to give the title compound as pale-yellow amorphous solid. MS (ESI, pos. ion.) m/z: 258 (M+1).

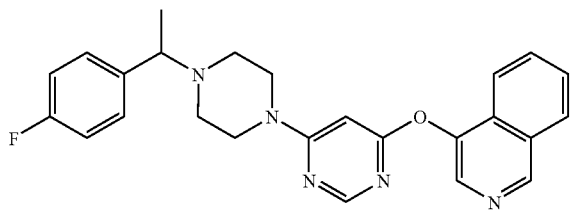

(b) 4-(6-(4-(1-(4-Fluorophenyl)ethyl)piperazin-1-yl)pyrimidin-4-yloxy)isoquinoline. 4-(6-Chloropyrimidin-4-yloxy)isoquinoline from step (a) above (0.162 g, 0.63 mmol) was reacted with 1-(1-(4-fluorophenyl)ethyl)piperazine, Example 2(b), (0.135 g, 0.65 mmol) under the conditions of Example 31(b) to give the title compound as amorphous white solid. MS (ESI, pos. ion.) m/z: 430 (M+1).

EXAMPLE 41

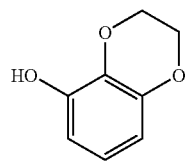

(a) 2,3-Dihydrobenzo[b][1,4]dioxin-5-ol. A mixture of benzene-1,2,3-triol (4.39 g, 34.81 mmol, Aldrich), 1,2-dibromoethane (1 mL, 11.6 mmol, Aldrich) and potassium carbonate (1.60 g, 11.58 mmol, Aldrich) in 2-butanone (300 mL, Aldrich) was heated to reflux for 18.5 h with stirring in an oil-bath. The reaction mixture was cooled to room temperature and diluted with DCM (100 mL) and water (50 mL). The DCM layer was separated, washed with 10% aqueous Na$_2$S$_2$O$_3$ (50 mL) and brine (100 mL), dried over anhydrous sodium sulfate, filtered, and evaporated. The residue was purified by silica gel column chromatography (gradient: 0-5% MeOH/DCM) to give the title compound as an amorphous solid. MS (ESI, pos. ion.) m/z: 153 (M+1).

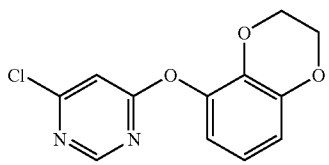

(b) 4-Chloro-6-(2,3-dihydrobenzo[b][1,4]dioxin-5-yloxy) pyrimidine. 2,3-Dihydro-benzo[b][1,4]dioxin-5-ol from step (a) above (0.247 g, 1.62 mmol) was reacted with 4,6-dichloropyrimidine (0.232 g, 1.56 mmol, Aldrich) under the conditions of Example 34(a) to give the title compound as pale-yellow amorphous solid. MS (ESI, pos. ion.) m/z: 265 (M+1).

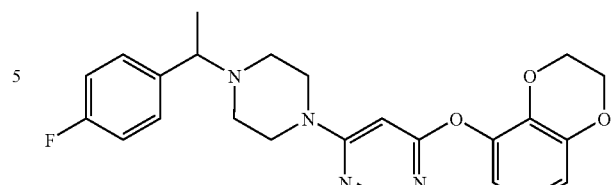

(c) 4-(2,3-Dihydrobenzo[b][1,4]dioxin-5-yloxy)-6-(4-(1-(4-fluorophenyl)ethyl)piperazin-1-yl)pyrimidine. 4-Chloro-6-(2,3-dihydrobenzo[b][1,4]dioxin-5-yloxy)pyrimidine from step (b) above (0.234 g, 0.88 mmol) was reacted with 1-(1-(4-fluorophenyl)ethyl)piperazine, Example 2(b), (0.185 g, 0.89 mmol) under the conditions of Example 31(b) to give the title compound as amorphous white solid. MS (ESI, pos. ion.) m/z: 437 (M+1).

EXAMPLE 42

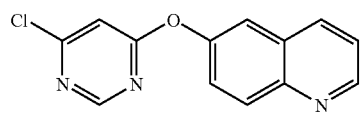

(a) 6-(6-Chloropyrimidin-4-yloxy)quinoline 6-Hydroxyquinoline (0.432 g, 2.98 mmol, Aldrich) was reacted with 4,6-dichloropyrimidine (0.445 g, 2.99 mmol, Aldrich) under the conditions of Example 28(a) to give the title compound as pale-yellow amorphous solid. MS (ESI, pos. ion.) m/z: 258 (M+1).

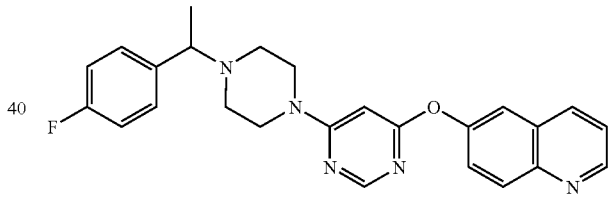

(b) 6-(6-(4-(1-(4-Fluorophenyl)ethyl)piperazin-1-yl)pyrimidin-4-yloxy)quinoline. 6-(6-Chloropyrimidin-4-yloxy)quinoline from step (a) above (0.135 g, 0.52 mmol) was reacted with 1-(1-(4-fluorophenyl)ethyl)piperazine, Example 2(b), (0.109 g, 0.52 mmol) under the conditions of Example 28(b) to give the title compound as white amorphous solid. MS (ESI, pos. ion.) m/z: 430 (M+1).

EXAMPLE 43

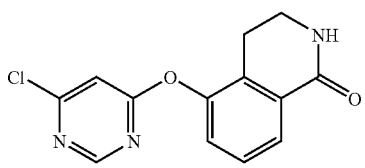

(a) 5-(6-Chloropyrimidin-4-yloxy)-3,4-dihydroisoquinolin-1 (2H)-one. 5-Hydroxy-3,4-dihydroisoquinolin-1 (2H)-one (0.274 g, 1.68 mmol, Chempacific) was reacted with 4,6-dichloropyrimidine (0.251 g, 1.69 mmol, Aldrich)

under the conditions of Example 34(a) to give the title compound as pale-yellow amorphous solid. MS (ESI, pos. ion.) m/z: 276 (M+1).

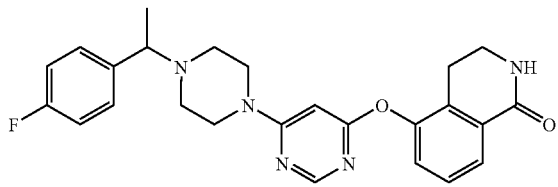

(b) 5-(6-(4-(1-(4-Fluorophenyl)ethyl)piperazin-1-yl)pyrimidin-4-yloxy)-3,4-dihydroisoquinolin-1(2H)-one. 5-(6-Chloropyrimidin-4-yloxy)-3,4-dihydroisoquinolin-1 (2H)-one from step (a) above (0.214 g, 0.78 mmol) was reacted with 1-(1-(4-fluorophenyl)ethyl)piperazine, Example 2(b), (0.162 g, 0.78 mmol) under the conditions of Example 37(b) to give the title compound as off-white oil. MS (ESI, pos. ion.) m/z: 448 (M+1).

EXAMPLE 44

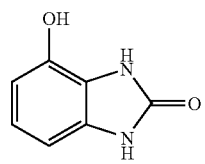

(a) 4-Hydroxy-1H-benzo[d]imidazol-2(3H)-one. To a suspension of 2,3-diaminophenol (1.24 g, 10 mmol, Aldrich) in THF (25 mL) was added carbonyldiimidazole (1.62 g, 10 mmol, Aldrich). The reaction mixture was stirred at room temperature for 16 h and evaporated in vacuo. The oily residue was suspended in MeOH and the solid precipitate was filtered. The filter cake was dried in vacuo to give the title compound. MS (ESI, pos. ion.) m/z: 151 (M+1).

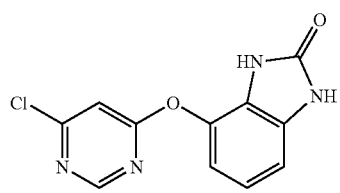

(b) 4-(6-Chloropyrimidin-4-yloxy)-1H-benzo[d]imidazol-2 (3H)-one. 4-Hydroxy-1H-benzo[d]imidazol-2(3H)-one from step (a) above (150 mg, 1 mmol) was reacted with 4,6-dichloropyrimidine (149 mg, 1 mmol, Aldrich) under the conditions of Example 34(a) to give the title compound. MS (ESI, pos. ion.) m/z: 263 (M+1).

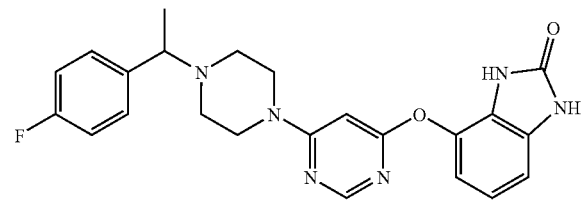

(c) 4-(6-(4-(1-(4-Fluorophenyl)ethyl)piperazin-1-yl)pyrimidin-4-yloxy)-1H-benzo-[d]imidazol-2(3H)-one. 4-(6-Chloropyrimidin-4-yloxy)-1H-benzo[d]imidazol-2(3H)-one from step (b) above (45 mg, 0.17 mmol) was reacted with 1-(1-(4-fluorophenyl)ethyl)piperazine, Example 2(b), (42 mg, 0.2 mmol) under the conditions of Example 28(b) to give the title compound as a white amorphous solid. MS (ESI, pos. ion.) m/z: 435.2 (M+1).

EXAMPLE 45

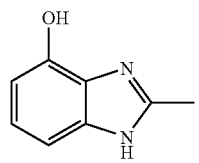

(a) 2-Methyl-1H-benzo[d]imidazol-4-ol. A mixture of 2,3-diaminophenol (620 mg, 5 mmol, Aldrich) and glacial acetic acid (5 mL) was heated in a microwave synthesizer at 200° C. for 5 min. The reaction mixture was cooled to room temperature and evaporated in vacuo to give the title compound as a black oil. MS (ESI, pos. ion.) m/z: 149.2 (M+1).

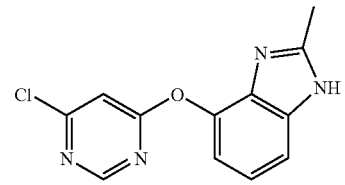

(b) 4-(6-Chloropyrimidin-4-yloxy)-2-methyl-1H-benzo[d] imidazole. 2-Methyl-1H-benzo[d]imidazol-4-ol from step (a) above (148 mg, 1 mmol) was reacted with 4,6-dichloropyrimidine (148 mg, 1 mmol, Aldrich) under the conditions of Example 34(a) to give the title compound as a yellow amorphous solid. MS (ESI, pos. ion.) m/z: 261 (M+1).

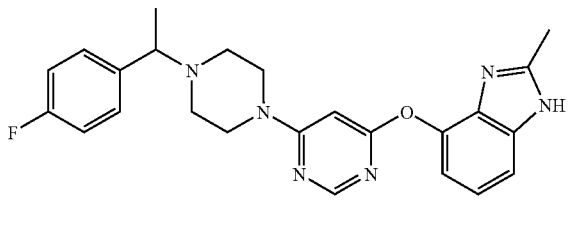

(c) 4-(6-(4-(1-(4-Fluorophenyl)ethyl)piperazin-1-yl)pyrimidin-4-yloxy)-2-methyl-1H-benzo[d]imidazole. 4-(6-Chloropyrimidin-4-yloxy)-2-methyl-1H-benzo[d]imidazole from step (b) above (30 mg, 0.12 mmol) was reacted with 1-(1-(4-fluorophenyl)ethyl)piperazine, Example

EXAMPLE 46

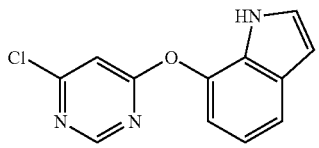

(a) 7-(6-Chloropyrimidin-4-yloxy)-1H-indole. 7-Hydroxyindole (400 mg, 3 mmol, Synchem) was reacted with 4,6-dichloropyrimidine (450 mg, 3 mmol, Aldrich) under the conditions of Example 34(a) to give the title compound as a white solid. MS (ESI, pos. ion.) m/z: 246.1 (M+1).

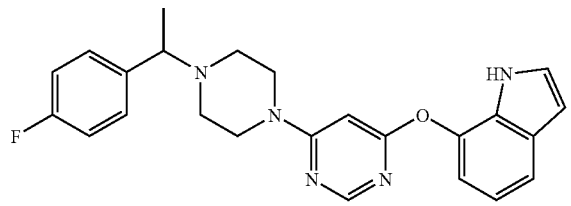

(b) 7-(6-(4-(1-(4-Fluorophenyl)ethyl)piperazin-1-yl)pyrimidin-4-yloxy)-1H-indole. 7-(6-Chloropyrimidin-4-yloxy)-1H-indole from step (a) above (95 mg, 0.39 mmol) was reacted with 1-(1-(4-fluorophenyl)ethyl)piperazine, Example 2(b), (85 mg, 0.4 mmol) under the conditions of Example 37(b) to give the title compound as a colorless solid. MS (ESI, pos. ion.) m/z: 418.2 (M+1).

EXAMPLE 47

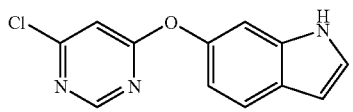

(a) 6-(6-Chloropyrimidin-4-yloxy)-1H-indole. 6-Hydroxyindole (266 mg, 2 mmol, Peakdale) was reacted with 4,6-dichloropyrimidine (298 mg, 2 mmol, Aldrich) under the conditions of Example 28(a) to give the title compound as a colorless oil. MS (ESI, pos. ion.) m/z: 246.2 (M+1).

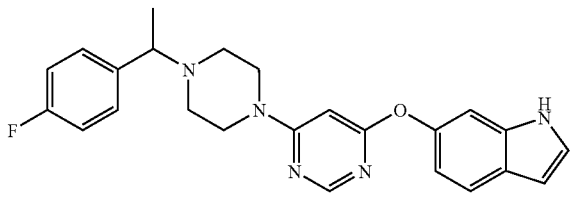

(b) 5-(6-(4-(1-(4-Fluorophenyl)ethyl)piperazin-1-yl)pyrimidin-4-yloxy)-1H-indole. 6-(6-Chloropyrimidin-4-yloxy)-1H-indole from step (a) above (123 mg, 0.5 mmol) was reacted with 1-(1-(4-fluorophenyl)ethyl)piperazine, Example 2(b), (104 mg, 0.5 mmol) under the conditions of Example 28(b) to give the title compound as an off white solid. MS (ESI, pos. ion.) m/z: 418 (M+1).

EXAMPLE 48

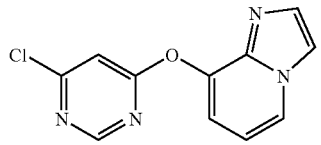

(a) 8-(6-Chloropyrimidin-4-yloxy)H-imidazo[1,2-a]pyridine. Imidazo[1,2-a]pyridin-8-ol (67 mg, 0.5 mmol, prepared as described in WO 2004/014871) was reacted with 4,6-dichloropyrimidine (75 mg, 0.5 mmol, Aldrich) under the conditions of Example 34(a) to give the title compound as a colorless film. MS (ESI, pos. ion.) m/z: 247 (M+1).

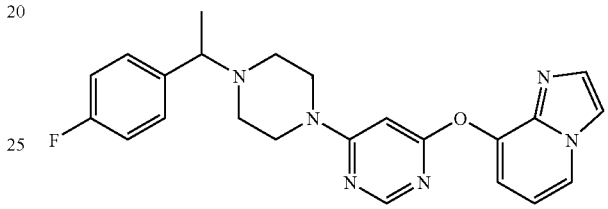

(b) 8-(6-(4-(1-(4-Fluorophenyl)ethyl)piperazin-1-yl)pyrimidin-4-yloxy)H-imidazo[1,2-a]pyridine. 8-(6-Chloropyrimidin-4-yloxy)H-imidazo[1,2-a]pyridine from step (a) above (25 mg, 0.1 mmol) was reacted with 1-(1-(4-fluorophenyl)ethyl)piperazine, Example 2(b), (25 mg, 0.12 mmol) under the conditions of Example 37(b) to give the title compound as a yellow film. MS (ESI, pos. ion.) m/z: 419.3 (M+1).

EXAMPLE 49

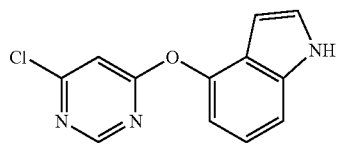

(a) 4-(6-Chloropyrimidin-4-yloxy)-1H-indole. 4-Hydroxyindole (133 mg, 1 mmol, Aldrich) was reacted with 4,6-dichloropyrimidine (185 mg, 1.25 mmol, Aldrich) under the conditions of Example 34(a) to give the title compound as a yellow solid. MS (ESI, pos. ion.) m/z: 246 (M+1).

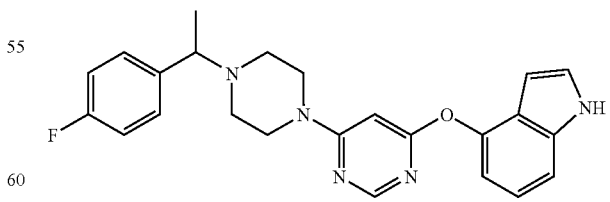

(b) 4-(6-(4-(1-(4-Fluorophenyl)ethyl)piperazin-1-yl)pyrimidin-4-yloxy)-1H-indole. 4-(6-Chloropyrimidin-4-yloxy)-1H-indole from step (a) above (200 mg, 0.8 mmol) was reacted with 1-(1-(4-fluorophenyl)ethyl)piperazine, Example 2(b), (167 mg, 0.8 mmol) under the conditions of Example 28(b) to give 105 mg (32%) of the title compound as a white amorphous solid. MS (ESI, pos. ion.) m/z: 418.2 (M+1).

EXAMPLE 50

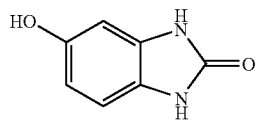

(a) 5-Hydroxy-1H-benzo[d]imidazol-2(3H)-one. To 5-methoxy-1H-benzo[d]imidazol-2(3H)-one (164 mg, 1 mmol, Lancaster) in DCM (2 mL) was added 1 M solution of aluminium trichloride in nitrobenzene (1 mL, 1 mmol, Aldrich). The reaction mixture was stirred at room temperature for 4 days and evaporated in vacuo. The residue was filtered through Celite®, and the filter cake was washed with DCM. The DCM washings were discarded and the filter cake was washed with MeOH. The dark brown MeOH washings were collected and evaporated under reduced pressure. The residue was purified by silica gel column chromatography (gradient: 5-20% MeOH/CH$_2$Cl$_2$) to give the title compound as a pale-yellow solid. MS (ESI, pos. ion.) m/z: 151 (M+1).

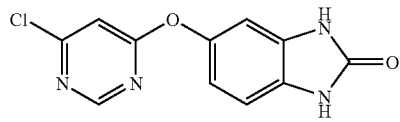

(b) 5-(6-Chloropyrimidin-4-yloxy)-1H-benzo[d]imidazol-2(3H)-one. 5-Hydroxy-1H-benzo[d]imidazol-2(3H)-one from step (a) above (100 mg, 0.66 mmol) was reacted with 4,6-dichloropyrimidine (105 mg, 0.7 mmol, Aldrich) under the conditions of Example 34(a) to give the title compound as a film. MS (ESI, pos. ion.) m/z: 263 (M+1).

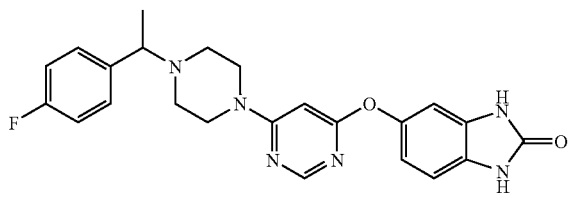

(c) 5-(6-(4-(1-(4-Fluorophenyl)ethyl)piperazin-1-yl)pyrimidin-4-yloxy)-1H-benzo[d]imidazol-2(3H)-one. 5-(6-Chloropyrimidin-4-yloxy)-1H-benzo[d]imidazol-2(3H)-one from step (b) above (95 mg, 0.37 mmol) was reacted with 1-(1-(4-fluorophenyl)ethyl)piperazine, Example 2(b), (80 mg, 0.38 mmol) under the conditions of Example 28(b) to give the title compound as a pale-yellow amorphous solid. MS (ESI, pos. ion.) m/z: 435.2 (M+1).

EXAMPLE 51

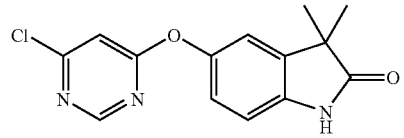

(a) 5-(6-Chloropyrimidin-4-yloxy)-3,3-dimethylindolin-2-one. 5-Hydroxy-3,3-dimethylindolin-2-one (177 mg, 1 mmol, RinTech) was reacted with 4,6-dichloro-pyrimidine (149 mg, 1 mmol, Aldrich) under the conditions of Example 34(a) to give the title compound as an oil. MS (ESI, pos. ion.) m/z: 290 (M+1).

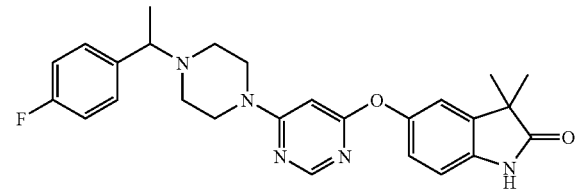

(b) 5-(6-(4-(1-(4-Fluorophenyl)ethyl)piperazin-1-yl)pyrimidin-4-yloxy)-3,3-di-methylindolin-2-one. 5-(6-Chloropyrimidin-4-yloxy)-3,3-dimethylindolin-2-one from step (a) above (56 mg, 0.2 mmol) was reacted with 1-(1-(4-fluorophenyl)-ethyl)piperazine, Example 2(b), (40 mg, 0.19 mmol) under the conditions of Example 28(b) to give the title compound as a colorless solid. MS (ESI, pos. ion.) m/z: 462.2 (M+1).

EXAMPLE 52

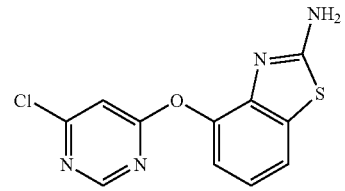

(a) 4-(6-Chloropyrimidin-4-yloxy)benzo[d]thiazol-2-amine. 2-Aminobenzo[d]thiazol-4-ol (166 mg, 1 mmol, Carbogen) was reacted with 4,6-dichloropyrimidine, (150 mg, 1 mmol, Aldrich) under the conditions of Example 34(a) to give the title compound as a white solid. MS (ESI, pos. ion.) m/z: 279 (M+1).

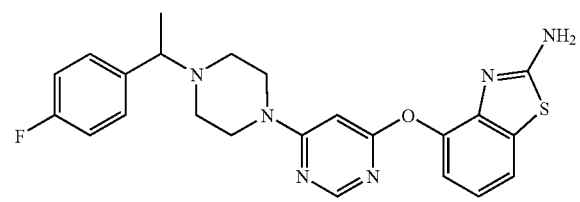

(b) 4-(6-(4-(1-(4-Fluorophenyl)ethyl)piperazin-1-yl)pyrimidin-4-yloxy)benzo[d]thiazol-2-amine. 4-(6-Chloropyrimidin-4-yloxy)benzo[d]thiazol-2-amine from step (a) above (150 mg, 0.54 mmol) was reacted with 1-(1-(4- fluorophenyl)ethyl)piperazine, Example 2(b), (115 mg, 0.55 mmol) under the conditions of Example 28(b) to give the title compound as an amorphous solid. MS (ESI, pos. ion.) m/z: 451.2 (M+1).

EXAMPLE 53

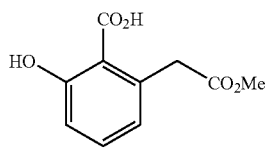

(a) 2-Hydroxy-6-(2-methoxy-2-oxoethyl)benzoic acid. To a solution of 3-hydroxy-homophthalic acid (4.5 g, 23 mmol, Apin) in MeOH (100 mL) was added dropwise acetyl chloride (10 mL, 9.1 g, 115 mmol, Aldrich) with stirring at 0° C. The reaction mixture was stirred at room temperature for 18 h and the solvent was evaporated under reduced pressure to afford the title compound as a white solid. $^1$H NMR (400 MHz, DMSO-d$_6$) δ ppm: 3.57 (s, 3H), 3.84 (s, 2H), 6.78 (d, J=7.43 Hz, 1H), 6.86 (d, J=8.22 Hz, 1H), 7.32 (t, J=7.82 Hz, 1H).

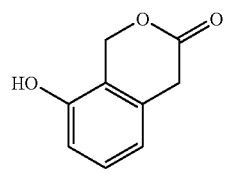

(b) 8-Hydroxy-1H-isochromen-3(4H)-one. To a solution of 2-hydroxy-6-(2-methoxy-2-oxoethyl)benzoic acid from step (a) above (4.2 g, 20 mmol) in anhydrous THF (10 mL) was added dropwise a solution of borane-methyl sulfide complex in THF (25 mL, 50 mmol, 2.0 M, Aldrich) with stirring at room temperature under N$_2$ atmosphere. The reaction mixture was stirred at reflux for 3.5 h, allowed to cool to 25° C., and quenched by the slow addition of 5 N HCl (20 mL). Upon complete addition, the mixture was stirred at reflux for 10 min and allowed to cool to 25° C. The mixture was concentrated in vacuo to a volume of ~50 mL, diluted with water (200 mL), and extracted with EtOAc (2×200 mL). The combined organic extract was washed with sat. NaCl (100 mL), dried over Na$_2$SO$_4$, filtered, and concentrated in vacuo to afford a white solid. The solid was purified by silica gel chromatography (gradient: 15-50% EtOAc in hexane) to provide the title product as a white solid. $^1$H NMR (400 MHz, DMSO-d$_6$) δ ppm: 3.52 (s, 2H), 5.11 (s, 2H), 6.54 (d, J=7.43 Hz, 1H), 6.57 (d, J=8.22 Hz, 1H), 6.94 (t, J=7.63 Hz, 1H), 9.72 (s, 1H).

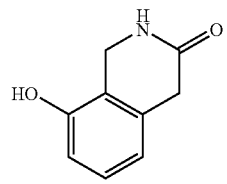

(c) 8-Hydroxy-1,2-dihydroisoquinolin-3(4H)-one. [analogous to the method of White, E. H.; Roswell, D. F.; Politzer, I. R.; Branchini, B. R. Active Site-Directed Inhibition with Substrates Producing Carbonium Ions: Chymotrypsin. *Methods Enzym*, 1977 (46), 216-220]. A mixture of 8-hydroxy-1H-isochromen-3(4H)-one from step (b) above (1.0 g, 6.1 mmol) and urea (2.2 g, 37 mmol, Aldrich) was heated at 200° C. in an oil bath with stirring for 30 min. The reaction mixture was allowed to cool to 25° C., treated with 1 N HCl (50 mL) and DCM (50 mL), and stirred for 5 h to provide a suspension. The suspension was filtered and the filter cake was washed with 1 N HCl (50 mL), water (50 mL), and DCM (50 mL). The combined DCM wash and filtrate was washed with sat. NaCl (30 mL) and evaporated under reduced pressure. The residue was dried in vacuo to afford the title product as a brown solid. $^1$H NMR (400 MHz, DMSO-d$_6$) δ ppm: 3.36 (s, 2H), 4.23 (s, 2H), 6.61 (d, J=7.43 Hz, 1H), 6.68 (d, J=7.82 Hz, 1H), 7.03 (t, J=7.83 Hz, 1H), 7.92 (s, 1H), 9.66 (s, 1H).

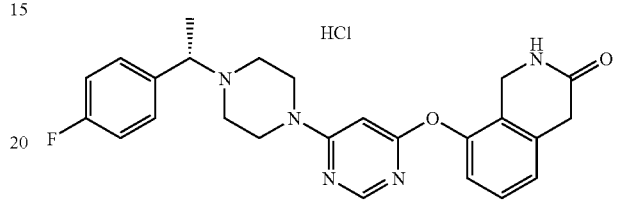

(d) (S)-8-(6-(4-(1-(4-Fluorophenyl)ethyl)piperazin-1-yl)pyrimidin-4-yloxy)-1,2-dihydroisoquinolin-3(4H)-one hydrochloride. A solution of 8-hydroxy-1,2-dihydroisoquinolin-3(4H)-one from step (c) above (200 mg, 1.2 mmol) in anhydrous DMF (5 mL) was purged with N$_2$ and treated with granular K$_2$CO$_3$ (1 g, 7.2 mmol, Aldrich) and 4,6-difluoropyrimidine (140 mg, 1.2 mmol, ABCR). The reaction mixture was magnetically stirred at 25° C. for 1 h. 1-[(1-S)-1-(4-Fluoro-phenyl)-ethyl]-piperazine, (200 mg, 0.96 mmol, prepared as described in Example 27) was added and the mixture was heated at 50° C. with stirring for 30 min. The reaction mixture was left to reach room temperature and was diluted with EtOAc (100 mL). The EtOAc solution was decanted from the solid K$_2$CO$_3$, washed with sat. NaHCO$_3$ (50 mL), water (50 mL), sat. NaCl (50 mL), dried over Na$_2$SO$_4$ and filtered. The filtrate was evaporated in vacuo and the residue was purified by silica gel column chromatography (gradient: 1-10% MeOH/EtOAc) to provide the pure product as a solid. The solid was dissolved in EtOAc (50 mL) and MeOH (5 mL) and treated with 1 N HCl in Et$_2$O (20 mL, Aldrich). The mixture was evaporated under reduced pressure and the residue was dried in vacuo to afford the title compound as a pale-yellow amorphous solid. MS (ESI, pos. ion.) m/z: 448 (M+1). Anal. Calcd for C$_{25}$H$_{26}$N$_5$FO$_2$.1.8 HCl.0.8H$_2$O: C, 56.92; H, 5.62; N, 13.28; Cl, 12.10; F, 3.60. Found: C, 56.60; H, 5.80; N, 12.91; Cl, 12.00; F, 3.51.

EXAMPLE 54

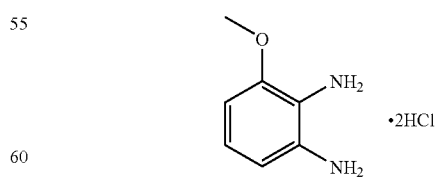

(a) 3-Methoxybenzene-1,2-diamine dihydrochloride. A mixture of 3-methoxy-2-nitro-phenylamine, Example 25(a), (18.0 g, 107 mmol), palladium on carbon (10 wt %, 1.8 g, 1.7 mmol, Aldrich) and MeOH (130 mL) was stirred under H$_2$ atmosphere for 40 h. The mixture was filtered through Celite® and the filtrate was concentrated in vacuo. The residue was dissolved in Et$_2$O and treated with 1M HCl in Et$_2$O (230 mL, 230 mmol, Aldrich). The solids were collected by filtration and washed with Et$_2$O. The filter cake was separated and dried in vacuo to give the title compound as a light-pink powder. MS (ESI, pos. ion.) t/z: 139 (M–HCl$_2$⁻).

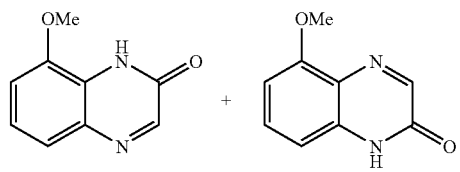

(b) 8-Methoxy-1H-quinoxalin-2-one and 5-Methoxy-1H-quinoxalin-2-one. A solution of 3-methoxybenzene-1,2-diamine dihydrochloride from step (a) above (5.28 g, 25 mmol) in EtOH (30 mL) and H$_2$O (70 mL) was neutralized by careful addition of solid NaHCO$_3$. A solution of ethyl glyoxylate (50% in toluene, 5.45 mL, 27.5 mmol, Fluka) was added and the mixture was stirred at room temperature for 24 h. The mixture was diluted with sat aq. NH$_4$Cl and extracted with 25% i-PrOH/CHCl$_3$ (4×). The combined organic extracts were dried over Na$_2$SO$_4$, filtered and evaporated in vacuo. Purification of the residue by column chromatography (gradient: 0-2.5% 2M NH$_3$ in MeOH/CH$_2$Cl$_2$) afforded 8-methoxy-1H-quinoxalin-2-one as an off-white powder [MS (ESI, pos. ion) m/z: 177 (M+1)] and 5-methoxy-1H-quinoxalin-2-one as an off-white powder [MS (ESI, pos. ion.) m/z: 177 (M+1)].

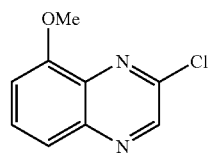

(c) 2-Chloro-8-methoxy-quinoxaline. A mixture of 8-methoxy-1H-quinoxalin-2-one from step (b) above (5.34 g, 30.3 mmol) and POCl$_3$ (100 mL, 1073 mmol, Aldrich) was heated to 105° C. for 4 h. The reaction mixture was allowed to cool to room temperature evaporated in vacuo. The residue was partitioned between sat. aq. NaHCO$_3$ and CH$_2$Cl$_2$ and stirred for 3 h. The CH$_2$Cl$_2$ layer was separated and the aqueous phase was extracted with CH$_2$Cl$_2$ (3×). The CH$_2$Cl$_2$ extracts were combined, dried over Na$_2$SO$_4$, and filtered through a pad of silica gel. The filter cake was washed with EtOAc and the filtrates were combined. Evaporation of the solvents gave a solid residue, which was dried in vacuo to afford the title compound. MS (ESI, pos. ion.) m/z: 195 (M+1).

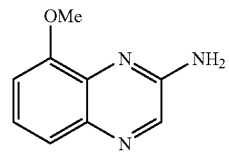

(d) 8-Methoxy-quinoxalin-2-ylamine. A mixture of 2-chloro-8-methoxy-quinoxaline from step (c) above (5.75 g, 29.5 mmol), conc NH$_4$OH (30 mL, Baker) and EtOH (3 mL) was heated to 110° C. in a pressure vessel for 28 h. The reaction mixture was cooled to room temperature and diluted with H$_2$O. The solid precipitate was filtered and washed with H$_2$O. The filter cake was purified on a short silica gel column, eluting with 1% MeOH/CH$_2$Cl$_2$ (500 mL) and 10% MeOH/CH$_2$Cl$_2$ (500 mL). The second fraction was separated and evaporated in vacuo. The solid residue was recrystallized from MeOH to give the title compound. MS (ESI, pos. ion.) m/z: 176 (M+1).

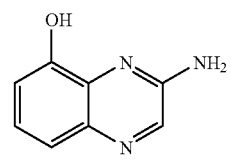

(e) 3-Amino-quinoxalin-5-ol. A mixture of 8-methoxy-quinoxalin-2-ylamine from step (d) above (2.51 g, 14.3 mmol) in CH$_2$Cl$_2$ (150 mL) was treated with BBr$_3$ (4.05 mL, 43 mmol, Aldrich) and heated to 44° C. for 6 d. The mixture was allowed to cool to room temperature, quenched with sat aq. NaHCO$_3$ and extracted with 25% i-PrOH/CHCl$_3$ (5×). The combined organic extracts were dried over Na$_2$SO$_4$, filtered and evaporated. The residue was dried in vacuo to give the title compound. MS (ESI, pos. ion.) m/z: 162 (M+1).

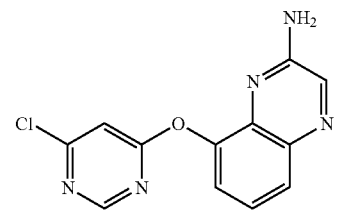

(f) 8-(6-Chloropyrimidin-4-yloxy)quinoxalin-2-amine. 3-Amino-quinoxalin-5-ol from step (e) above (500 mg, 3.1 mmol) was reacted with 4,6-dichloropyrimidine (462 mg, 3.1 mmol, Aldrich) under the conditions of Example 26(a) to give the title compound. MS (ESI, pos. ion.) m/z: 274 (M+1).

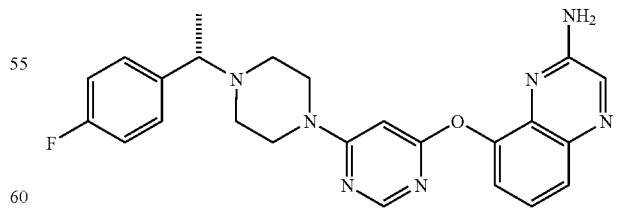

(g) (S)-8-(6-(4-(1-(4-Fluorophenyl)ethyl)piperazin-1-yl)pyrimidin-4-yloxy)quinoxalin-2-amine. 8-(6-Chloropyrimidin-4-yloxy)quinoxalin-2-amine from step (f) above (424 mg, 1.55 mmol) was reacted with (S)-1-(1-(4-fluorophenyl)ethyl)piperazine (323 mg, 1.55 mmol, prepared as described in Example 27) under the conditions of Example 26(b) to give the title compound. MS (ESI, pos. ion.) m/z: 446 (M+1). Mp: 114° C.

EXAMPLE 55

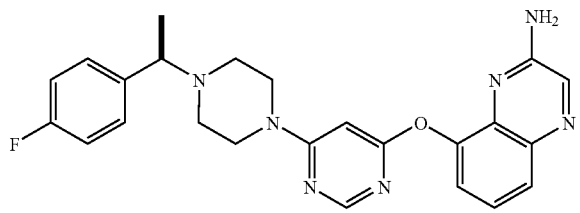

(R)-8-(6-(4-(1-(4-Fluorophenyl)ethyl)piperazin-1-yl)pyrimidin-4-yloxy)quinoxalin-2-amine. 8-(6-Chloropyrimidin-4-yloxy)quinoxalin-2-amine, Example 54(f), (424 mg, 1.55 mmol) was reacted with (R)-1-(1-(4-fluorophenyl)ethyl)piperazine, Example 23(c), (323 mg, 1.55 mmol) under the conditions of Example 26(b) to give the title compound. MS (ESI, pos. ion.) m/z: 446 (M+1). Mp: 118° C.

EXAMPLE 56

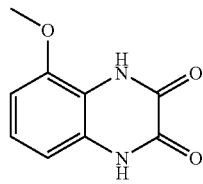

(a) 5-Methoxyquinoxaline-2,3(1H,4H)-dione. 3-Methoxybenzene-1,2-diamine dihydrochloride (Example 54(a)) was partitioned between 10% aq. $Na_2CO_3$ and $CH_2Cl_2$. The aqueous layer was extracted with $CH_2Cl_2$ (2×). The combined organic extracts were dried over $Na_2SO_4$, filtered and evaporated to yield 3-methoxybenzene-1,2-diamine. A mixture of the diamine (912 mg, 6.6 mmol) and diethyl oxalate (9.0 mL, 66 mmol, Aldrich) was heated at 185° C. for 18 h. The reaction mixture was left to reach room temperature and the solid precipitate was filtered. The filter cake was washed with EtOH and dried in vacuo to give the title compound. MS (ESI, pos. ion.) m/z: 191 (M+1).

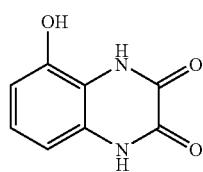

(b) 5-Hydroxyquinoxaline-2,3(1H,4H)-dione. To a solution of 5-methoxyquinoxaline-2,3(1H,4H)-dione from step (a) above (180 mg, 0.94 mg) in $CH_2Cl_2$ (10 mL) was added $BBr_3$ (1.0 M in $CH_2Cl_2$, 2.8 mL, 2.8 mmol, Aldrich) and the mixture was heated at 45° C. for 20 h. The reaction mixture was left to reach room temperature and the solid precipitate was filtered. The filter cake was washed with MeOH (3×) and dried in vacuo to give the title compound. MS (ESI, pos. ion.) m/z: 179 (M+1).

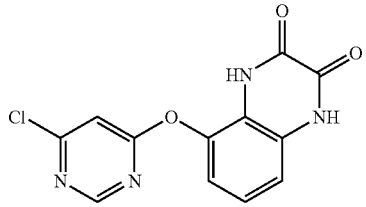

(c) 5-(6-Chloropyrimidin-4-yloxy)quinoxaline-2,3(1H,4H)-dione. 5-Hydroxy-quinoxaline-2,3(1H,4H)-dione from step (b) above (356 mg, 2.0 mmol) was reacted with 4,6-dichloropyrimidine (289 mg, 2.0 mmol, Aldrich) under the conditions of Example 26(a) to give the title compound.

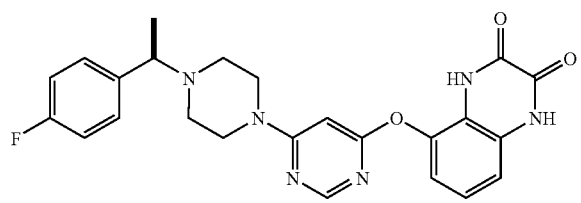

(d) (R)-5-(6-(4-(1-(4-Fluorophenyl)ethyl)piperazin-1-yl)pyrimidin-4-yloxy)quinoxaline-2,3(1H,4H)-dione. 5-(6-Chloropyrimidin-4-yloxy)quinoxaline-2,3(1H,4H)-dione from step (c) above (100 mg, 0.34 mmol) was reacted with (R)-1-(1-(4-fluorophenyl)ethyl)piperazine, Example 23(c), (72 mg, 0.34 mmol) under the conditions of Example 26(b) to give the title compound. MS (ESI, pos. ion.) t/z: 463 (M+1).

EXAMPLE 57

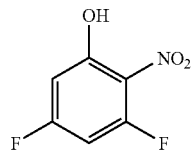

(a) 3,5-Difluoro-2-nitrophenol. To a solution of 1,3,5-trifluoro-2-nitrobenzene (10 g, 5.6 mmol, Aldrich) in DMSO (50 mL) was added 10 N NaOH (12 mL, 120 mmol, J T Baker) and the mixture was stirred at room temperature for 20 h. The reaction mixture was diluted with $H_2O$ and extracted with $Et_2O$. The aqueous layer was separated, acidified with conc. HCl to pH 5, and extracted with $Et_2O$ (2×). The combined organic extracts were washed with brine, dried over $Na_2SO_4$, filtered and concentrated in vacuo. The residue was purified by silica gel column chromatography (gradiend: 0-30% EtOAc/hexanes) to give the title compound. MS (ESI, neg. ion.) m/z: 174 (M−1).

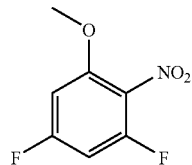

(b) 1,5-Difluoro-3-methoxy-2-nitrobenzene. To a mixture of 3,5-difluoro-2-nitrophenol from step (a) above (7.18 g, 41.1 mmol) and K$_2$CO$_3$ (8.52 g, 61.7 mmol, Aldrich) in DMF (30 mL) was added iodomethane (4.36 ml, 70 mmol, Aldrich). After stirring for 18 h at room temperature, the mixture was diluted with H$_2$O and extracted with Et$_2$O (2×). The combined organics were dried over Na$_2$SO$_4$, filtered and evaporated under reduced pressure. The residue was dried in vacuo to give the title compound.

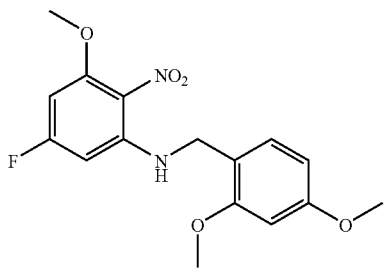

(c) N-(2,4-Dimethoxybenzyl)-5-fluoro-3-methoxy-2-nitrobenzenamine. A mixture of 1,5-difluoro-3-methoxy-2-nitrobenzene from step (b) above (4.00 g, 21.2 mmol), 2,4-dimethoxybenzylamine (3.18 mL, 21.2 mmol, Aldrich) and triethylamine (2.96 ml, 21.2 mmol) in THF (210 mL) was heated at 70° C. for 20 h. The reaction mixture was cooled to room temperature and the volatiles were removed in vacuo. The residue was dissolved in CH$_2$Cl$_2$ and passed through a pad of silica gel, eluting with CH$_2$Cl$_2$. The CH$_2$Cl$_2$ solution was evaporated under reduced pressure and the residue was dried in vacuo to give the title compound as a yellow solid. MS (ESI, pos. ion.) m/z: 359 (M+23).

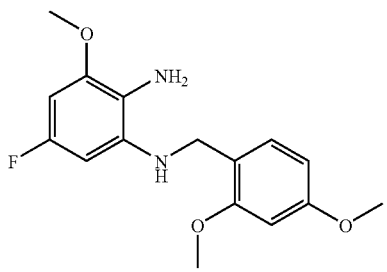

(d) N$^1$-(2,4-Dimethoxybenzyl)-5-fluoro-3-methoxybenzene-1,2-diamine. A mixture of N-(2,4-dimethoxybenzyl)-5-fluoro-3-methoxy-2-nitrobenzenamine from step (c) above (5.40 g, 16.1 mmol), iron powder (325 mesh, 4.32 g, 77.3 mmol, Aldrich), NH$_4$Cl (1.19 g, 22.5 mmol, Aldrich) and conc. HCl (4 drops) in EtOH (100 mL) and H$_2$O (20 mL) was heated to 70° C. with stirring for 3 h. The reaction mixture was left to reach room temperature and the stirring was continued for 16 h. The mixture was filtered through a Celite® pad and the filtrate was evaporated under reduced pressure. The residue was dried in vacuo to give the title compound.

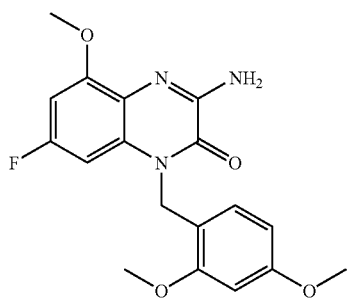

(e) 1-(2,4-Dimethoxybenzyl)-3-amino-7-fluoro-5-methoxyquinoxalin-2(1H)-one. A mixture of N$^1$-(2,4-dimethoxybenzyl)-5-fluoro-3-methoxybenzene-1,2-diamine from step (d) above (4.92 g, 16.1 mmol) and ethyl 2-ethoxy-2-iminoacetate (5.54 g, 38.14 mmol, prepared according to *J. Chem. Soc. Perkin. Trans.* 1, 1999, 1789) in EtOH (100 mL) was stirred at room temperature for 18 h. The reaction mixture was filtered and the filter cake was washed with EtOH, and dried in vacuo to give the title compound as a fine white powder. MS (ESI, pos. ion.) m/z: 360 (M+1).

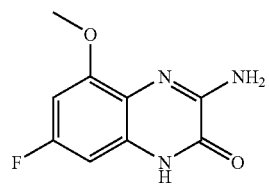

(f) 3-Amino-7-fluoro-5-methoxyquinoxalin-2(1H)-one. A mixture of 1-(2,4-dimethoxybenzyl)-3-amino-7-fluoro-5-methoxyquinoxalin-2(1H)-one from step (e) above (3.0 g, 8.34 mmol), anisole (4 mL, Aldrich) and trifluoroacetic acid (60 mL, Aldrich) was heated to 65° C. for 16 h, and to 85° C. for 5 h. The reaction mixture was allowed to cool to room temperature and evaporated under reduced pressure. The residue was partitioned between 25% i-PrOH/CHCl$_3$ and sat aq. NaHCO$_3$. The organic layer was collected and evaporated to give a solid residue. The aqueous layer was filtered and the filter cake was washed with H$_2$O, and dried under vacuo. The filter cake was combined with the solid residue and recrystallized from MeOH to give the title compound. MS (ESI, pos. ion.) m/z: 210 (M+1).

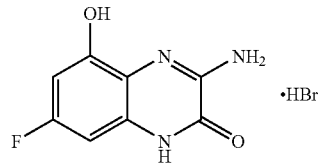

(g) 3-Amino-7-fluoro-5-hydroxyquinoxalin-2(1H)-one hydrobromide. 3-Amino-7-fluoro-5-methoxyquinoxalin-2(1H)-one from step (f) above (2.0 g, 9.56 mmol) was reacted with BBr$_3$ (1.0 M solution in CH$_2$Cl$_2$, 58 mL, 58 mmol) under the conditions of Example 56(b) to give the title compound. MS (ESI, pos. ion.) m/z: 196 (M+1).

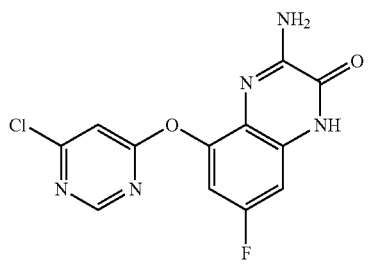

(h) 3-Amino-5-(6-chloropyrimidin-4-yloxy)-7-fluoroquinoxalin-2(1H)-one. 3-Amino-7-fluoro-5-hydroxyquinoxalin-2(1H)-one hydrobromide from step (g) above (390 mg, 2.0 mmol) was reacted with 4,6-dichloropyrimidine (298 mg, 2.0 mmol, Lancaster) under the conditions of Example 26(a) to give the title compound. MS (ESI, pos. ion.) m/z: 308 (M+1).

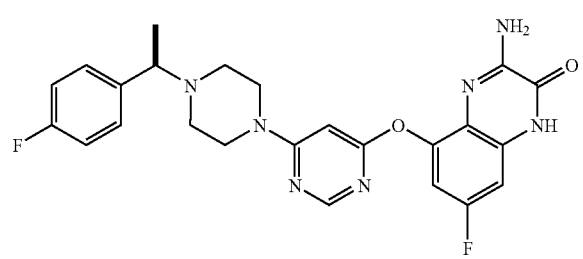

(i) (R)-3-Amino-7-fluoro-5-(6-(4-(1-(4-fluorophenyl)ethyl)piperazin-1-yl)pyrimidin-4-yloxy)quinoxalin-2(1H)-one. 3-Amino-5-(6-chloropyrimidin-4-yloxy)-7-fluoroquinoxalin-2(1H)-one from step (h) above (200 mg, 0.65 mmol) was reacted with (R)-1-(1-(4-fluorophenyl)ethyl)piperazine, Example 23(c), (135 mg, 0.65 mmol) under the conditions of Example 26(b) to give the title compound. MS (ESI, pos. ion.) m/z: 480 (M+1). Mp: 315° C.

EXAMPLE 58

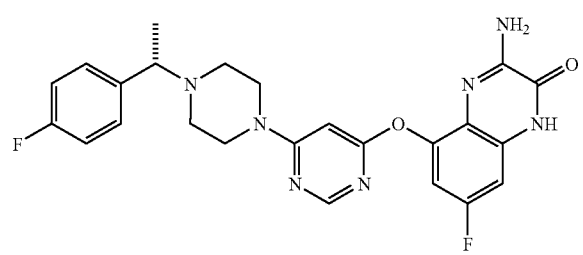

(S)-3-Amino-7-fluoro-5-(6-(4-(1-(4-fluorophenyl)ethyl)piperazin-1-yl)pyrimidin-4-yloxy)quinoxalin-2(1H)-one. 3-Amino-5-(6-chloropyrimidin-4-yloxy)-7-fluoroquinoxalin-2(1H)-one, Example 57(h), (150 mg, 0.49 mmol) was reacted with (S)-1-(1-(4-fluorophenyl)ethyl)piperazine (101 mg, 0.49 mmol, prepared as described in Example 27) under the conditions of Example 26(b) to give the title compound. MS (ESI, pos. ion.) m/z: 480 (M+1). Mp: 288° C.

EXAMPLE 59

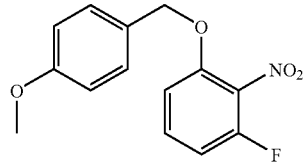

(a) 1-((3-Fluoro-2-nitrophenoxy)methyl)-4-methoxybenzene. To a suspension of NaH (60% dispersion in mineral oil, 4.0 g, 100 mmol) in THF (200 mL) was added dropwise 4-methoxybenzyl alcohol (12 mL, 96.2 mmol) with stirring at 0° C. The mixture was stirred at room temperature for 15 min and 2,6-difluoronitrobenzene (15.26 g, 100 mmol, Aldrich) was then added. The resulting red solution was heated to 65° C. with stirring and the progress of the reaction was monitored by TLC. The reaction mixture was cooled to room temperature and the solvent was removed in vacuo. The residue was dissolved in MeOH, evaporated onto $SiO_2$ and eluted through a $SiO_2$ plug with 25% EtOAc/hexane. Evaporation of the solvent under reduced pressure gave the crude product as a yellow amorphous solid, which was used in the next step without additional purification. MS (ESI, neg. ion.) m/z: 274.1 [M−1].

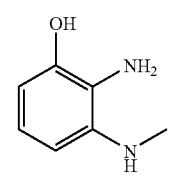

(b) 3-(4-Methoxybenzyloxy)-N-methyl-2-nitrobenzenamine. A mixture of 1-((3-fluoro-2-nitrophenoxy)methyl)$_4$-methoxybenzene from step (a) above (0.60 g, 2.16 mmol) and methylamine (2.0 M solution in MeOH, 3.3 mL, 6.6 mmol, Aldrich) was heated in a microwave synthesizer at 140° C. for 30 min. The reaction mixture was cooled to room temperature and evaporated under reduced pressure. The residue was dried in vacuo to give the title compound. MS (ESI, pos. ion.) m/z: 289 (M+1).

(c) 2-Amino-3-(methylamino)phenol. A mixture of 3-(4-methoxybenzyloxy)-N-methyl-2-nitrobenzenamine from step (b) above (3.11 g, 10.8 mmol) and 10% palladium on carbon (0.31 g, Aldrich) in MeOH (50 mL) was stirred under $H_2$ atmosphere for 16 h. The mixture was filtered through a Celite® pad and the filtrate was evaporated under reduced pressure to give the title compound.

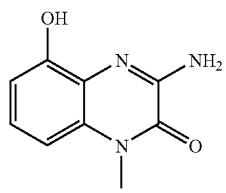

(d) 3-Amino-5-hydroxy-1-methylquinoxalin-2(1H)-one. 2-Amino-3-(methylamino)phenol from step (c) above (934 mg, 6.67 mmol) was reacted with ethyl 2-ethoxy-2-iminoacetate (1.96 g, 13.52 mmol, prepared according to *J. Chem. Soc. Perkin. Trans.* 1, 1999, 1789) under the conditions of Example 57(e) to give the title compound. MS (ESI, pos. ion.) m/z: 192 (M+1).

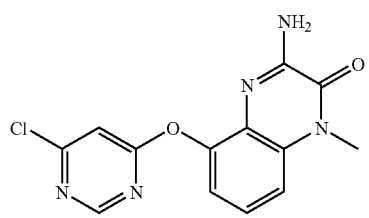

(e) 3-Amino-5-(6-chloropyrimidin-4-yloxy)-1-methylquinoxalin-2(1H)-one. 3-Amino-5-hydroxy-1-methylquinoxalin-2(1H)-one from step (d) above (191 mg, 1.0 mmol) was reacted with 4,6-dichloropyrimidine (149 mg, 1.0 mmol, Aldrich) under the conditions of Example 26(a) to give the title compound. MS (ESI, pos. ion.) m/z: 304 (M+1).

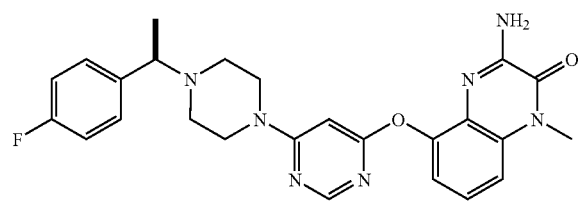

(f) (R)-3-Amino-5-(6-(4-(1-(4-fluorophenyl)ethyl)piperazin-1-yl)pyrimidin-4-yloxy)-1-methylquinoxalin-2(1H)-one. 3-Amino-5-(6-chloropyrimidin-4-yloxy)-1-methylquinoxalin-2(1H)-one from step (e) above (100 mg, 0.33 mmol) was reacted with (R)-1-(1-(4-fluorophenyl)ethyl)piperazine, Example 23(c), (68 mg, 0.33 mmol) under the conditions of Example 26(b) to give the title compound. MS (ESI, pos. ion.) m/z: 476 (M+1). Mp: 256° C.

EXAMPLE 60

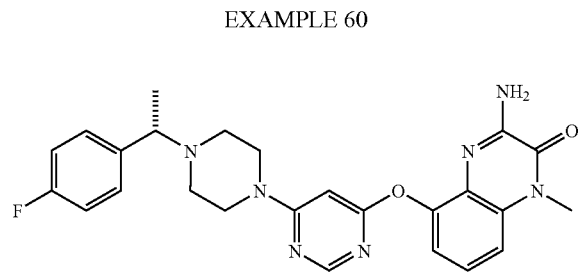

(S)-3-Amino-5-(6-(4-(1-(4-fluorophenyl)ethyl)piperazin-1-yl)pyrimidin-4-yloxy)-1-methylquinoxalin-2(1H)-one.

3-Amino-5-(6-chloropyrimidin-4-yloxy)-1-methylquinoxalin-2(1H)-one, Example 59(e), (80 mg, 0.26 mmol) was reacted with (S)-1-(1-(4-fluorophenyl)ethyl)piperazine (55 mg, 0.26 mmol, prepared as described in Example 27) under the conditions of Example 26(b) to give the title compound. MS (ESI, pos. ion.) m/z: 476 (M+1).

EXAMPLE 61

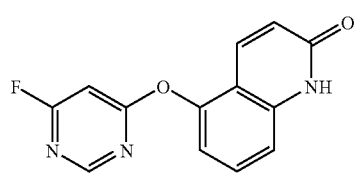

(a) 5-(6-Fluoropyrimidin-4-yloxy)quinolin-2(1H)-one. A mixture of 5-hydroxyquinolin-2-(1H)-one (0.05 g, 0.31 mmol, prepared as described in Shono, T., Matsumura, Y., Kashimura, S., *J. Org. Chem.* 1981, 46, 3719.), 4,6-difluoropyrimidine (0.036 mL, 0.31 mmol, ABCR) and cesium carbonate (0.2 g, 0.62 mmol) in DMF (5 mL) was stirred at 25° C. for 2 h. The reaction mixture was then diluted with H₂O (25 mL). The resulting off-white precipitate was collected by filtration and dried under vacuo to give the title compound. MS (ESI, pos. ion.) m/z: 258 (M+1).

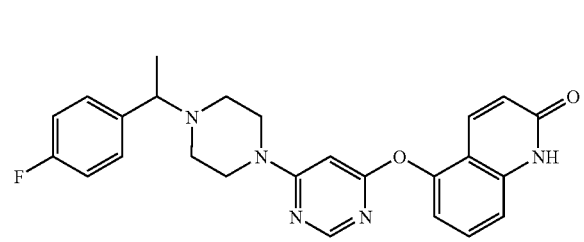

(b) 5-(6-(4-(1-(4-Fluorophenyl)ethyl)piperazin-1-yl)pyrimidin-4-yloxy)quinoline-2(1H)-one. 5-(6-Fluoropyrimidin-4-yloxy)quinolin-2(1H)-one from step (a) above (0.05 g, 0.19 mmol) was reacted with 1-[(1S,1R)-1-(4-fluoro-phenyl)-ethyl]-piperazine, Example 2(b), (0.04 g, 0.19 mmol) under the conditions of Example 26(b) to give the title compound. Mp: 242.2° C. MS (ESI, pos. ion.) m/z: 446 (M+1).

ADDITIONAL EXAMPLES

The following examples were prepared from various hydroxy-substituted bicyclic heterocycles (prepared as described in WO 2004/014871), 4,6-difluoropyrimidine (ABCR) and 1-[(1S,1R)-1-(4-fluoro-phenyl)-ethyl]-piperazine (Example 2(b)) according to the general procedure described for the preparation of Example 61, or with slight modifications thereof:

| Ex. | Structure | Melt. Point (° C.) | M.S. (ESI) m/z |
|---|---|---|---|
| 62 | 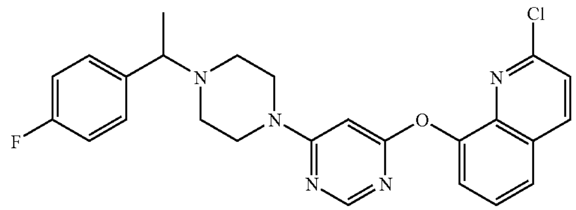 | 148 | 464 (M + 1) |
| 63 | 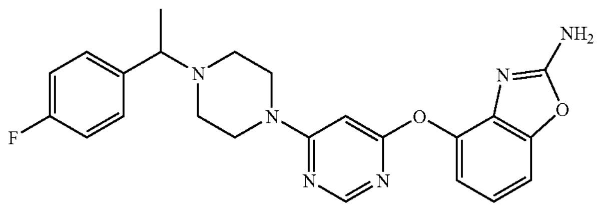 | 217 | 435 (M + 1) |
| 64 | 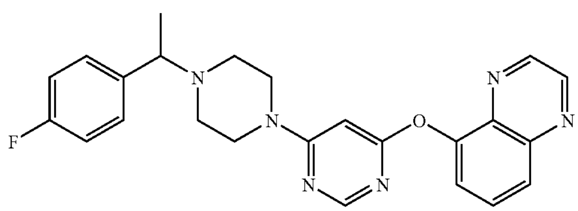 | 67.2 | 431 (M + 1) |
| 65 | 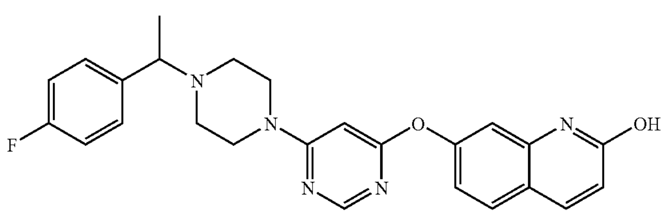 | 228 | 446 (M + 1) |

EXAMPLE 66

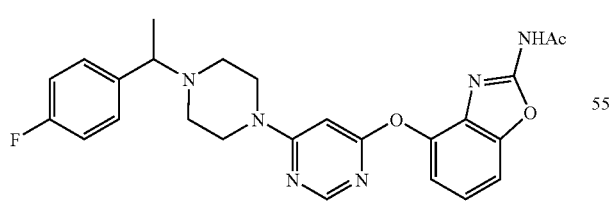

N-(4-(6-(4-(1-(4-Fluorophenyl)ethyl)piperazin-1-yl)pyrimidin-4-yloxy)benzo[d]oxazol-2-yl)acetamide. 4-(6-(4-(1-(4-Fluorophenyl)ethyl)piperazin-1-yl)pyrimidin-4-yloxy)benzo[d]oxazol-2-amine (0.06 g, 0.14 mmol, Example 63) was reacted with acetic anhydride under the conditions of Example 1(b) to give the desired product. Mp: 199.8° C. MS (ESI, pos. ion) m/z: 477 (M+1).

EXAMPLE 67

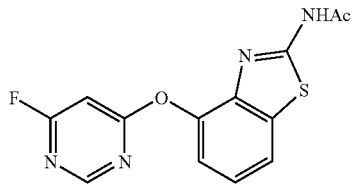

(a) N-(4-(6-Fluoropyrimidin-4-yloxy)benzo[d]thiazol-2-yl)acetamide. A mixture of N-(4-hydroxybenzo[d]thiazol-2-yl)acetamide (0.3 g, 1.4 mmol, prepared according to the procedure described in WO 2003/099284) and 4,6-difluoropyrimidine (0.17 mL, 1.4 mmol, ABCR) in DMF (3 mL) was stirred at 25° C. for 18 h. The reaction mixture was diluted with H$_2$O (20 mL) and the resulting off-white precipitate was collected by filtration, and dried under vacuo to give the title compound. MS (ESI, pos. ion) m/z: 305 (M+1).

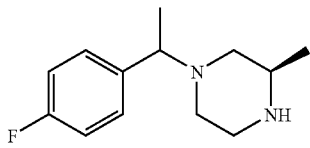

(b) (3R)-1-(1-(4-Fluorophenyl)ethyl)-3-methylpiperazine. The title compound was prepared from (S)-(+)-methylpiperazine (0.5 g, 5.0 mmol, Aldrich) in a manner analogous to Example 2(a) and isolated as an amorphous solid. MS (ESI, pos. ion) m/z: 223 (M+1).

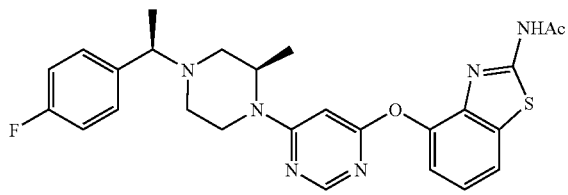

(c) N-(4-(6-((R)-4((R)-(1-(4-Fluorophenyl)ethyl)-2-methylpiperazin-1-yl)pyrimidin-4-yloxy)benzo[d]thiazol-2-yl)acetamide. A mixture of (3R)-1-(1-(4-fluorophenyl)ethyl)-3-methylpiperazine from step (b) above (0.20 g, 0.90 mmol) and N-(4-(6-fluoropyrimidin-4-yloxy)benzo[d]thiazol-2-yl)acetamide from step (a) above (0.27 g, 0.90 mmol, Albany Molecular) in DMF (5 mL) was stirred at 100° C. for 3 h. The reaction mixture was allowed to reach 25° C. and was diluted with H₂O (40 mL). The resulting pale-orange precipitate was collected by filtration and dissolved in DCM (50 mL). The solution was washed with H₂O (2×), dried over anhydrous sodium sulfate, filtered, and evaporated. The residue was purified by silica gel column chromatography (gradient: 04% MeOH/DCM) to give the product as a mixture of diastereoisomers. MS (ESI, pos. ion) m/z: 507 (M+1). The diastereoisomers were separated by supercritical fluid chromatography [35% EtOH (0.2% diethyl amine)]. The first fraction was collected and concentrated in vacuo to yield the title compound as a white solid. MS (ESI, pos. ion) m/z: 507 (M+1).

EXAMPLE 68

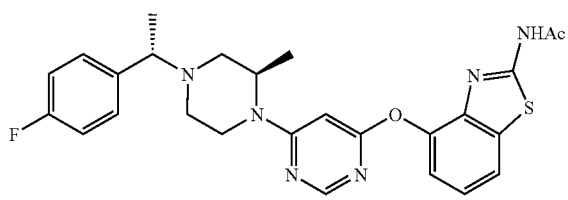

N-(4-(6-((R)-4-((S)-1-(4-Fluorophenyl)ethyl)-2-methylpiperazin-1-yl)pyrimidin-4-yloxy)benzol[d]thiazol-2-yl)acetamide. This compound was isolated as a white solid from the second fraction of the supercritical fluid chromatography (35% EtOH (0.2% diethyl amine)) separation of the diastereomeric mixture of Example 67(c). MS (ESI, pos. ion) m/z: 507 (M+1).

EXAMPLE 69

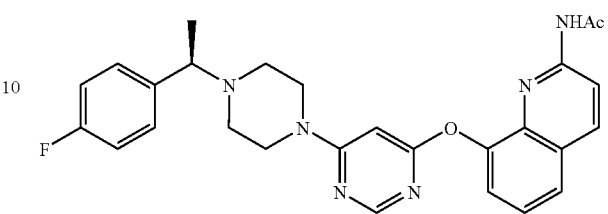

(R)-N-(8-(6-(4-(1-(4-Fluorophenyl)ethyl)piperazin-1-yl)pyrimidin-4-yloxy)quinolin-2-yl)acetamide. 8-(6-{4-[(1R)-(4-Fluoro-phenyl)-ethyl]-piperazine-1-yl}-pyrimidin-4-yloxy)-quinolin-2-ylamine, Example 23(d), (0.05 g, 0.11 mmol,) was reacted with acetic anhydride under the conditions of Example 1(b) to give the title compound. Mp: 134° C. MS (ESI, pos. ion) m/z: 487 (M+1).

EXAMPLE 70

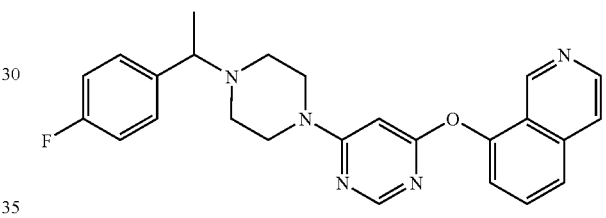

8-(6-(4-(1-(4-Fluorophenyl)ethyl)piperazin-1-yl)pyrimidin-4-yloxy)isoquinoline. A mixture of 4-fluoro-6-(4-(1-(4-fluorophenyl)ethyl)piperazin-1-yl)pyrimidine, Example 33(a), (0.05 g, 0.17 mmol), isoquinolin-8-ol (0.037 g, 0.25 mmol, Monomer Chem, Inc.) cesium carbonate (0.081 g, 0.25 mmol), and DMSO (1 mL) was heated in a microwave synthesizer at 115° C. for 0.5 h. The reaction mixture was allowed to cool to room temperature, diluted with H₂O (30 mL) and extracted with DCM (2×50 mL). The combined organic extracts were washed with H₂O (2×30 mL), dried over Na₂SO₄, filtered, and concentrated in vacuo. The residue was purified by silica gel column chromatography (gradient: 0-8% MeOH/DCM) to give the title compound as a white solid. Mp: 114° C. MS (ESI, pos. ion) m/z: 430 (M+1).

EXAMPLE 71

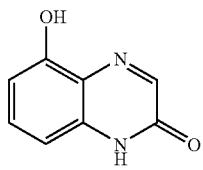

(a) 5-Hydroxyquinoxalin-2(1H)-one. 5-Methoxy-1H-quinoxalin-2-one, Example 54(b), (0.3 g, 1.7 mmol) was reacted with AlCl₃ (2.0 g, 15.5 mmol, Aldrich) under the conditions of Example 25(d) to give the title compound as a brown powder. MS (ESI, pos. ion) m/z: 163 (M+1).

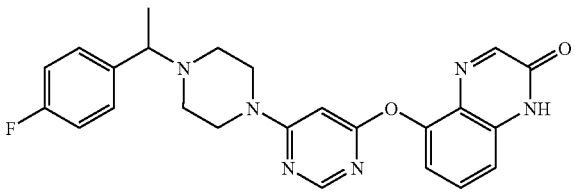

(b) 5-(6-(4-(1-(4-Fluorophenyl)ethyl)piperazin-1-yl)pyrimidin-4-yloxy)quinolin-2(1H)-one. 4-Fluoro-6-(4-(1-(4-fluorophenyl)ethyl)piperazin-1-yl)pyrimidine, Example 33(a), (0.4 g, 1.3 mmol) was reacted with 5-hydroxyquinolin-2(1H)-one from step (a) above (0.24 g, 1.5 mmol) under the conditions of Example 70 to give 0.121 g (21%) of the title compound as a pale-yellow solid. Mp: 263° C. MS (ESI, pos. ion) m/z: 447 (M+1).

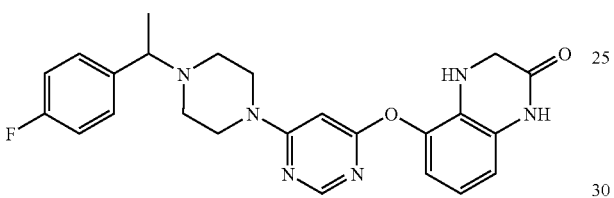

(c) 5-(6-(4-(1-(4-Fluorophenyl)ethyl)piperazin-1-yl)pyrimidin-4-yloxy)-3,4-dihydroquinoxalin-2-(1H)-one. A mixture of 5-(6-(4-(1-(4-fluorophenyl)ethyl)piperazin-1-yl)pyrimidin-4-yloxy)quinolin-2(1H)-one from step (b) above (0.04 g, 0.09 mmol) and NaBH$_4$ (0.014 g, 0.36 mmol, Aldrich) in EtOH (2 mL) was stirred at 25° C. for 19 h. The reaction mixture was diluted with saturated sodium bicarbonate (25 mL) and extracted with DCM (3×25 mL). The combined organic extracts were washed with H$_2$O (25 mL), dried over Na$_2$SO$_4$, filtered, and evaporated in vacuo. The residue was suspended in MeOH and filtered. The filter cake was separated and dried under vacuo to give the title compound as an off-white solid. Mp: 221° C. MS (ESI, pos. ion) m/z: 449 (M+1).

EXAMPLE 72

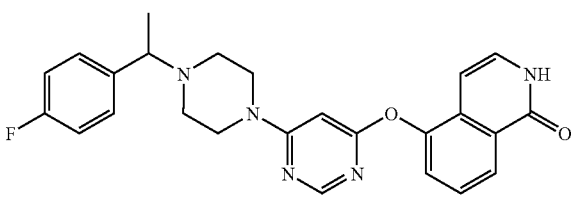

5-(6-(4-(1-(4-Fluorophenyl)ethyl)piperazin-1-yl)pyrimidin-4-yloxy)isoquinolin-1(2H)-one. 4-Fluoro-6-(4-(1-(4-fluorophenyl)ethyl)piperazin-1-yl)pyrimidine, Example 33(a), (0.074 g, 0.24 mmol) was reacted with 1,5-isoquinolinediol (0.058 g, 0.36 mmol, Sigma) under the conditions of Example 70 to give the title compound. Mp: 249° C. MS (ESI, pos. ion) m/z: 446 (M+1).

EXAMPLE 73

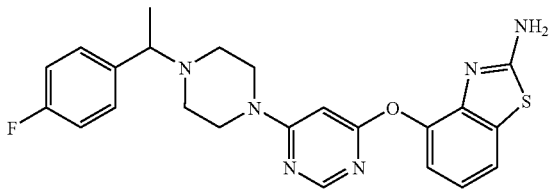

4-(6-(4-(1-(4-Fluorophenyl)ethyl)piperazin-1-yl)pyrimidin-4-yloxy)benzol[d]thiazol-2-amine. 4-Fluoro-6-(4-(1-(4-fluorophenyl)ethyl)piperazin-1-yl)pyrimidine (0.145 g, 0.48 mmol, Example 37(a)) was reacted with 2-amino-benzothiazol-4-ol (0.13 g, 0.78 mmol, CarboGen) under the conditions of Example 26(b) to give the title compound as a white solid. Mp: 222° C. MS (ESI, pos. ion) m/z: 451 (M+1).

EXAMPLE 74

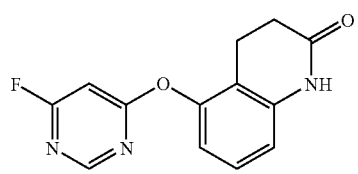

(a) 5-(6-Fluoropyrimidin-4-yloxy)-3,4-dihydroquinolin-2(1H)-one. The title compound was prepared from 5-hydroxy-3,4-dihydroquinolin-2(1H)-one (0.1 g, 0.61 mmol, prepared as described in Shono, T., Matsumura, Y., Kashimura, S., J. Org. Chem. 1981, 46, 3719.) and 4,6-difluoropyrimidine (0.072 mL, 0.62 mmol) under the conditions of Example 61(b) to give the title compound. MS (ESI, pos. ion) m/z: 260 (M+1).

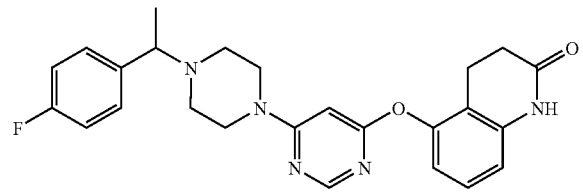

(b) 5-(6-(4-(1-(4-Fluorophenyl)ethyl)piperazin-1-yl)pyrimidin-4-yloxy)-3,4-dihydroquinolin-2(1H)-one. 5-(6-Fluoropyrimidin-4-yloxy)-3,4-dihydroquinolin-2(1H)-one from step (a) above (0.075 g, 0.29 mmol) was reacted with 1-[(1S,1R)-1-(4-fluoro-phenyl)-ethyl]-piperazine, Example 2(b), (0.04 g, 0.19 mmol) under the conditions of Example 26(b) to give the title compound. MS (ESI, pos. ion) m/z: 448 (M+1).

Capsaicin-Induced Ca2+ Influx in Primary Dorsal Root Ganglion Neurons

Embryonic 19 day old (E19) dorsal root ganglia (DRG) were dissected from timed-pregnant, terminally anesthetized Sprague-Dawley rats (Charles River, Wilmington, Mass.) and collected in ice-cold L-15 media (Life Technologies, Grand Island, N.Y.) containing 5% heat inactivated horse serum (Life Technologies). The DRG were then dissociated into single cell suspension using a papain dissociation system (Worthington Biochemical Corp., Freehold, N.J.). The dissociated cells were pelleted at 200×g for 5 min and re-suspended in EBSS containing 1 mg/ml ovomucoid inhibitor, 1 mg/ml ovalbumin and 0.005% DNase. Cell suspension was centrifuged through a gradient solution containing 10 mg/ml ovomucoid inhibitor, 10 mg/ml ovalbumin at 200×g for 6 min to remove cell debris; and filtered through a 88-μm nylon mesh (Fisher Scientific, Pittsburgh, Pa.) to remove any clumps. Cell number was determined with a hemocytometer and cells were seeded into poly-ornithine 100 μg/ml (Sigma) and mouse laminin 1 μg/ml (Life Technologies)-coated 96-well plates at $10\times10^3$ cells/well in complete medium. The complete medium consists of minimal essential medium (MEM) and Ham's F12, 1:1, penicillin (100 U/ml), and streptomycin (100 μg/ml), and nerve growth factor (10 ng/ml), 10% heat inactivated horse serum (Life Technologies). The cultures were kept at 37° C., 5% $CO_2$ and 100% humidity. For controlling the growth of non-neuronal cells, 5-fluoro-2'-deoxyuridine (75 μM) and uridine (180 μM) were included in the medium. Activation of VR1 is achieved in these cellular assays using either a capsaicin stimulus (ranging from 0.01-10 μM) or by an acid stimulus (addition of 30 mM Hepes/Mes buffered at pH 4.1). Compounds are also tested in an assay format to evaluate their agonist properties at VR1.

Capsaicin Antagonist Assay: E-19 DRG cells at 5 days in culture are incubated with serial concentrations of VR1 antagonists, in HBSS (Hanks buffered saline solution supplemented with BSA 0.1 mg/ml and 1 mM Hepes at pH 7.4) for 15 min, 37° C. Cells are then challenged with a VR1 agonist, capsaicin 200 nM, in activation buffer containing 0.1 mg/ml BSA, 15 mM Hepes, pH 7.4, and 10 μCi/Ml $^{45}Ca^{2+}$ (Amersham) in Ham's F12 for 2 min at 37° C.

Acid Antagonist Assay: Compounds are pre-incubated with E-19 DRG cells for 2 minutes prior to addition of Calcium-45 in 30 mM Hepes/Mes buffer (Final Assay pH 5) and then left for an additional 2 minutes prior to compound washout. Final 45Ca (Amersham CES3-2mCi) at 10 μCi/mL.

Agonist Assay: Compounds are incubated with E-19 DRG cells for 2 minutes in the presence of Calcium-45 prior to compound washout. Final $^{45}Ca^{2+}$ (Amersham CES3-2 mCi) at 10 μCi/mL.

Compound Washout and Analysis: Assay plates are washed using an ELX405 plate washer (Bio-Tek Instruments Inc.) immediately after functional assay. Wash 3× with PBS Mg2+/Ca2+ free, 0.1 mg/mL BSA. Aspirate between washes. Read plates using a MicroBeta Jet (Wallac Inc.). Compound activity is then calculated using appropriate computational algorithms.

$^{45}Calcium^{2+}$ Assay Protocol

Compounds may be assayed using Chinese Hamster Ovary cell lines stably expressing either human VR1 or rat VR1 under a CMV promoter. Cells can be cultured in Growth Medium, routinely passaged at 70% confluency using trypsin and plated in the assay plate 24 hours prior to compound evaluation.

Possible Growth Medium:
DMEM, high glucose (Gibco 11965-084).
10% Dialyzed serum (Hyclone SH30079.03).
1× Non-Essential Amino Acids (Gibco 11140-050).
1× Glutamine-Pen-Strep (Gibco 10378-016).
Geneticin, 450 μg/mL (Gibco 10131-035).

Compounds can be diluted in 100% DMSO and tested for activity over several log units of concentration [40 μM-2 pM]. Compounds may be further diluted in HBSS buffer (pH 7.4) 0.1 mg/mL BSA, prior to evaluation. Final DMSO concentration in assay would be 0.5%. Each assay plate can be controlled with a buffer only and a known antagonist compound (either capsazepine or one of the described VR1 antagonists).

Activation of VR1 can be achieved in these cellular assays using either a capsaicin stimulus (ranging from 0.1-1 μM) or by an acid stimulus (addition of 30 mM Hepes/Mes buffered at pH 4.1). Compounds may also tested in an assay format to evaluate their agonist properties at VR1.

Capsaicin Antagonist Assay: Compounds may be pre-incubated with cells (expressing either human or rat VR1) for 2 minutes prior to addition of Calcium-45 and Capsaicin and then left for an additional 2 minutes prior to compound washout. Capsaicin (0.5 nM) can be added in HAM's F12, 0.1 mg/mL BSA, 15 mM Hepes at pH 7.4. Final $^{45}Ca$ (Amersham CES3-2mCi) at 10 μCi/mL.

The following compounds exhibit IC50 values of less than 10 mM in the Human VR1 Capsaicin Antagonist Assay:

2-((6-(4-((1S)-1-(4-fluorophenyl)ethyl)-1-piperazinyl)-4-pyrimidinyl)oxy)quinoline;

2-chloro-8-((6-(4-((1S)-1-(4-fluorophenyl)ethyl)-1-piperazinyl)-4-pyrimidinyl)oxy)quinoline;

3-((6-(4-((1S)-1-(4-fluorophenyl)ethyl)-1-piperazinyl)-4-pyrimidinyl)oxy)isoquinoline;

3-amino-5-((6-(4-((1R)-1-(4-fluorophenyl)ethyl)-1-piperazinyl)-4-pyrimidinyl)oxy)-2(1H)-quinoxalinone;

3-amino-5-((6-(4-((1R)-1-(4-fluorophenyl)ethyl)-1-piperazinyl)-4-pyrimidinyl)oxy)-1-methyl-2(1H)-quinoxalinone;

3-amino-5-((6-(4-((1R)-1-(4-fluorophenyl)ethyl)-1-piperazinyl)-4-pyrimidinyl)oxy)-1-methyl-2(1H)-quinoxalinone;

3-amino-5-((6-(4-((1S)-1-(4-fluorophenyl)ethyl)-1-piperazinyl)-4-pyrimidinyl)oxy)-2(1H)-quinoxalinone;

3-amino-5-((6-(4-((1S)-1-(4-fluorophenyl)ethyl)-1-piperazinyl)-4-pyrimidinyl)oxy)-1-methyl-2(1H)-quinoxalinone;

3-amino-5-((6-(4-((1S,1R)-1-(4-fluorophenyl)ethyl)-1-piperazinyl)-4-pyrimidinyl)oxy)-2(1H)-quinoxalinone;

3-amino-7-fluoro-5-((6-(4-((1R)-1-(4-fluorophenyl)ethyl)-1-piperazinyl)-4-pyrimidinyl)oxy)-2(1H)-quinoxalinone;

3-amino-7-fluoro-5-((6-(4-((1R)-1-(4-fluorophenyl)ethyl)-1-piperazinyl)-4-pyrimidinyl)oxy)-2(1H)-quinoxalinone;

3-amino-7-fluoro-5-((6-(4-((1S)-1-(4-fluorophenyl)ethyl)-1-piperazinyl)-4-pyrimidinyl)oxy)-2(1H)-quinoxalinone;

4-((6-(4-((1R)-1-(4-fluorophenyl)ethyl)-1-piperazinyl)-4-pyrimidinyl)oxy)quinoline;

4-((6-(4-((1R)-1-(4-fluorophenyl)ethyl)-1-piperazinyl)-4-pyrimidinyl)oxy)isoquinoline;

4-((6-(4-((1R)-1-(4-fluorophenyl)ethyl)-1-piperazinyl)-4-pyrimidinyl)oxy)-1,3-benzothiazol-2-amine;

4-((6-(4-((1S)-1-(4-fluorophenyl)ethyl)-1-piperazinyl)-4-pyrimidinyl)oxy)-1,3-dihydro-2H-benzimidazol-2-one;

4-((6-(4-((1S)-1-(4-fluorophenyl)ethyl)-1-piperazinyl)-4-pyrimidinyl)oxy)-2-methyl-1H-benzimidazole;

4-((6-(4-((1S)-1-(4-fluorophenyl)ethyl)-1-piperazinyl)-4-pyrimidinyl)oxy)-1H-indole;

4-((6-(4-((1S)-1-(4-fluorophenyl)ethyl)-1-piperazinyl)-4-pyrimidinyl)oxy)-1,3-benzoxazol-2-amine;

4-(2,3-dihydro-1,4-benzodioxin-6-yloxy)-6-(4-((1S)-1-(4-fluorophenyl)ethyl)-1-piperazinyl)pyrimidine;

4-(2,3-dihydro-benzo[1,4]dioxin-5-yloxy)-6-{4-[1-(4-fluoro-phenyl)-ethyl]-piperazin-1-yl}-pyrimidine;

5-((6-(4-((1R)-1-(4-fluorophenyl)ethyl)-1-piperazinyl)-4-pyrimidinyl)oxy)-1,4-dihydro-2,3-quinoxalinedione;

5-((6-(4-((1R)-1-(4-fluorophenyl)ethyl)-1-piperazinyl)-4-pyrimidinyl)oxy)isoquinoline;
5-((6-(4-((1R)-1-(4-fluorophenyl)ethyl)-1-piperazinyl)-4-pyrimidinyl)oxy)quinoline;
5-((6-(4-((1R)-1-(4-fluorophenyl)ethyl)-1-piperazinyl)-4-pyrimidinyl)oxy)-2(1H)-quinolinone;
5-((6-(4-((1R)-1-(4-fluorophenyl)ethyl)-1-piperazinyl)-4-pyrimidinyl)oxy)-3,4-dihydro-2(1H)-quinolinone;
5-((6-(4-((1S)-1-(4-fluorophenyl)ethyl)-1-piperazinyl)-4-pyrimidinyl)oxy)-1,3-dihydro-2H-benzimidazol-2-one;
5-((6-(4-((1S)-1-(4-fluorophenyl)ethyl)-1-piperazinyl)-4-pyrimidinyl)oxy)-3,3-dimethyl-1,3-dihydro-2H-indol-2-one;
5-((6-(4-((1S)-1-(4-fluorophenyl)ethyl)-1-piperazinyl)-4-pyrimidinyl)oxy)-2(1H)-quinoxalinone;
5-((6-(4-((1S)-1-(4-fluorophenyl)ethyl)-1-piperazinyl)-4-pyrimidinyl)oxy)-3,4-dihydro-2(1H)-quinoxalinone;
5-((6-(4-((1S)-1-(4-fluorophenyl)ethyl)-1-piperazinyl)-4-pyrimidinyl)oxy)-4a,8a-dihydroquinoxaline; 5-((6-(4-((1S)-1-(4-fluorophenyl)ethyl)-1-piperazinyl)-4-pyrimidinyl)oxy)-1(2H)-isoquinolinone;
6-((6-(4-((1S)-1-(4-fluorophenyl)ethyl)-1-piperazinyl)-4-pyrimidinyl)oxy)-1H-indole;
6-((6-(4-((1S)-1-(4-fluorophenyl)ethyl)-1-piperazinyl)-4-pyrimidinyl)oxy)-2H-1,4-benzoxazin-3(4H)-one;
6-((6-(4-((1S)-1-(4-fluorophenyl)ethyl)-1-piperazinyl)-4-pyrimidinyl)oxy)isoquinoline;
6-((6-(4-((1S)-1-(4-fluorophenyl)ethyl)-1-piperazinyl)-4-pyrimidinyl)oxy)-3,4-dihydro-2H-1,4-benzoxazine;
7-((6-(4-((1S)-1-(4-fluorophenyl)ethyl)-1-piperazinyl)-4-pyrimidinyl)oxy)-1H-indole;
7-((6-(4-((1S)-1-(4-fluorophenyl)ethyl)-1-piperazinyl)-4-pyrimidinyl)oxy)quinoline;
7-((6-(4-((1S)-1-(4-fluorophenyl)ethyl)-1-piperazinyl)-4-pyrimidinyl)oxy)isoquinoline;
7-((6-(4-((1S)-1-(4-fluorophenyl)ethyl)-1-piperazinyl)-4-pyrimidinyl)oxy)-2-quinolinol;
8-((6-(4-((1R)-1-(4-fluorophenyl)ethyl)-1-piperazinyl)-4-pyrimidinyl)oxy)-2-quinolinamine;
8-((6-(4-((1R)-1-(4-fluorophenyl)ethyl)-1-piperazinyl)-4-pyrimidinyl)oxy)-2-quinoxalinamine;
8-((6-(4-((1R)-1-(4-fluorophenyl)ethyl)-1-piperazinyl)-4-pyrimidinyl)oxy)quinoline;
8-((6-(4-((1S)-1-(4-fluorophenyl)ethyl)-1-piperazinyl)-4-pyrimidinyl)oxy)-2-uinolinamine;
8-((6-(4-((1S)-1-(4-fluorophenyl)ethyl)-1-piperazinyl)-4-pyrimidinyl)oxy)imidazo[1,2-a]pyridine;
8-((6-(4-((1S)-1-(4-fluorophenyl)ethyl)-1-piperazinyl)-4-pyrimidinyl)oxy)-1,4-dihydro-3(2H)-isoquinolinone;
8-((6-(4-((1S)-1-(4-fluorophenyl)ethyl)-1-piperazinyl)-4-pyrimidinyl)oxy)-2-uinoxalinamine;
8-((6-(4-((1S)-1-(4-fluorophenyl)ethyl)-1-piperazinyl)-4-pyrimidinyl)oxy)isoquinoline;
N-(4-((6-((2R)-4-((1R)-1-(4-fluorophenyl)ethyl)-2-methyl-1-piperazinyl)-4-pyrimidinyl)oxy)-1,3-benzothiazol-2-yl)acetamide;
N-(4-((6-((2R)-4-((1S)-1-(4-fluorophenyl)ethyl)-2-methyl-1-piperazinyl)-4-pyrimidinyl)oxy)-1,3-benzothiazol-2-yl)acetamide;
N-(4-((6-((2R)-4-((1S)-1-(4-fluorophenyl)ethyl)-2-methyl-1-piperazinyl)-4-pyrimidinyl)oxy)-1,3-benzothiazol-2-yl)acetamide;
N-(4-((6-((2S)-4-((1S,1R)-1-(4-fluorophenyl)ethyl)-2-methyl-1-piperazinyl)-4-pyrimidinyl)oxy)-1,3-benzothiazol-2-yl)acetamide;
N-(4-((6-((3R)-4-((1R)-1-(4-fluorophenyl)ethyl)-3-methyl-1-piperazinyl)-4-pyrimidinyl)oxy)-1,3-benzothiazol-2-yl)acetamide;
N-(4-((6-((3R)-4-((1R)-1-(4-fluorophenyl)propyl)-3-methyl-1-piperazinyl)-4-pyrimidinyl)oxy)-1,3-benzothiazol-2-yl)acetamide;
N-(4-((6-((3R)-4-((1S)-1-(4-fluorophenyl)ethyl)-3-methyl-1-piperazinyl)-4-pyrimidinyl)oxy)-1,3-benzothiazol-2-yl)acetamide;
N-(4-((6-((3R)-4-((1S)-1-(4-fluorophenyl)propyl)-3-methyl-1-piperazinyl)-4-pyrimidinyl)oxy)-1,3-benzothiazol-2-yl)acetamide;
N-(4-((6-(4-((1R)-1-(4-fluorophenyl)ethyl)-1-piperazinyl)-4-pyrimidinyl)oxy)-1,3-benzothiazol-2-yl)acetamide;
N-(4-((6-(4-((1S)-1-(4-fluorophenyl)ethyl)-1-piperazinyl)-4-pyrimidinyl)oxy)-1,3-benzothiazol-2-yl)acetamide;
N-(4-((6-(4-((1S)-1-(4-fluorophenyl)ethyl)-1-piperazinyl)-4-pyrimidinyl)oxy)-1,3-benzoxazol-2-yl)acetamide;
N-(4-((6-(4-((1S,1R)-1-(2,4-difluorophenyl)ethyl)-1-piperazinyl)-4-pyrimidinyl)oxy)-1,3-benzothiazol-2-yl)acetamide;
N-(4-((6-(4-((1S,1R)-1-(2-fluorophenyl)ethyl)-1-piperazinyl)-4-pyrimidinyl)oxy)-1,3-benzothiazol-2-yl)acetamide;
N-(4-((6-(4-((1S,1R)-1-(2-furanyl)ethyl)-1-piperazinyl)-4-pyrimidinyl)oxy)-1,3-benzothiazol-2-yl)acetamide;
N-(4-((6-(4-((1S,1R)-1-(2-thienyl)ethyl)-1-piperazinyl)-4-pyrimidinyl)oxy)-1,3-benzothiazol-2-yl)acetamide;
N-(4-((6-(4-((1S,1R)-1-(3-fluorophenyl)ethyl)-1-piperazinyl)-4-pyrimidinyl)oxy)-1,3-benzothiazol-2-yl)acetamide;
N-(4-((6-(4-((1S,1R)-1-(3-thienyl)ethyl)-1-piperazinyl)-4-pyrimidinyl)oxy)-1,3-benzothiazol-2-yl)acetamide;
N-(4-((6-(4-((1S,1R)-1-(4-(methyloxy)phenyl)ethyl)-1-piperazinyl)-4-pyrimidinyl)oxy)-1,3-benzothiazol-2-yl)acetamide;
N-(4-((6-(4-((1S,1R)-1-(4-(trifluoromethyl)phenyl)ethyl)-1-piperazinyl)-4-pyrimidinyl)oxy)-1,3-benzothiazol-2-yl)acetamide;
N-(4-((6-(4-((1S,1R)-1-(4-bromophenyl)ethyl)-1-piperazinyl)-4-pyrimidinyl)oxy)-1,3-benzothiazol-2-yl)acetamide;
N-(4-((6-(4-((1S,1R)-1-(4-chlorophenyl)ethyl)-1-piperazinyl)-4-pyrimidinyl)oxy)-1,3-benzothiazol-2-yl)acetamide;
N-(4-((6-(4-((1S,1R)-1-(4-fluorophenyl)ethyl)-1-piperazinyl)-4-pyrimidinyl)oxy)-1,3-benzothiazol-2-yl)acetamide;
N-(4-((6-(4-((1S,1R)-1-(4-fluorophenyl)propyl)-1-piperazinyl)-4-pyrimidinyl)oxy)-1,3-benzothiazol-2-yl)acetamide;
N-(4-((6-(4-((1S,1R)-1-(4-pyridinyl)ethyl)-1-piperazinyl)-4-pyrimidinyl)oxy)-1,3-benzothiazol-2-yl)acetamide;
N-(4-((6-(4-((1S,1R)-1-(5-bromo-2-thienyl)ethyl)-1-piperazinyl)-4-pyrimidinyl)oxy)-1,3-benzothiazol-2-yl)acetamide;
N-(4-((6-(4-((1S,1R)-1-(5-chloro-2-thienyl)ethyl)-1-piperazinyl)-4-pyrimidinyl)oxy)-1,3-benzothiazol-2-yl)acetamide; and
N-(8-((6-(4-((1R)-1-(4-fluorophenyl)ethyl)-1-piperazinyl)-4-pyrimidinyl)oxy)-2-quinolinyl)acetamide.

Acid Antagonist Assay: Compounds can be pre-incubated with cells (expressing either human or rat VR1) for 2 minutes prior to addition of Calcium-45 in 30 mM Hepes/Mes buffer (Final Assay pH 5) and then left for an additional 2 minutes prior to compound washout. Final $^{45}$Ca (Amersham CES3-2mCi) at 10 µCi/mL.

Agonist Assay: Compounds can be incubated with cells (expressing either human or rat VR1) for 2 minutes in the presence of Calcium-45 prior to compound washout. Final $^{45}$Ca (Amersham CES3-2mCi) at 10 µCi/mL.

Compound Washout and Analysis: Assay plates can be washed using an ELX405 plate washer (Bio-Tek Instruments Inc.) immediately after functional assay. One can wash 3× with PBS $Mg2^+/Ca^{2+}$ free, 0.1 mg/mL BSA, aspirating between washes. Plates may be read using a MicroBeta Jet (Wallac Inc.). Compound activity may then calculated using appropriate computational algorithms.

Useful nucleic acid sequences and proteins may be found in U.S. Pat. Nos. 6,335,180, 6,406,908 and 6,239,267, herein incorporated by reference in their entirety.

For the treatment of vanilloid-receptor-diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating vanilloid-receptor-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions).

The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, isopropoxymethyl, α-methoxyethyl, groups such as α-(($C_1$-$C_4$)alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:

1. A compound having the structure:

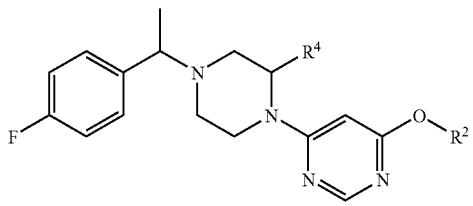

or any pharmaceutically-acceptable salt thereof, wherein:

$R^2$ is independently a partially saturated or unsaturated 8-, 9-, 10- or 11-membered bicyclic ring containing 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$;

$R^4$ is H or methyl;

$R^a$ is independently, at each instance, H or $R^b$; and $R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —OC$_{1-4}$alkyl, —NH$_2$, —NHC$_{1-4}$alkyl, —N(C$_{1-4}$alkyl)C$_{1-4}$alkyl.

2. A compound according to claim 1, or any pharmaceutically-acceptable salt thereof, wherein $R^2$ is quinolin-8-yl, benzoxazol-4-yl, benzothiazol-4-yl or quinoxalinon-5-yl, either of which is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$.

3. A compound according to claim 1, or any pharmaceutically-acceptable salt thereof, wherein $R^3$ is H and $R^{3'}$ is methyl.

4. A compound selected from the group of:

2-((6-(4-((1S)-1-(4-fluorophenyl)ethyl)-1-piperazinyl)-4-pyrimidinyl)oxy)quinoline;

2-chloro-8-((6-(4-((1S)-1-(4-fluorophenyl)ethyl)-1-piperazinyl)-4-pyrimidinyl)oxy)quinoline;

3-((6-(4-((1S)-1-(4-fluorophenyl)ethyl)-1-piperazinyl)-4-pyrimidinyl)oxy)isoquinoline;

3-amino-5-((6-(4-((1R)-1-(4-fluorophenyl)ethyl)-1-piperazinyl)-4-pyrimidinyl)oxy)-2(1H)-quinoxalinone;

3-amino-5-((6-(4-((1R)-1-(4-fluorophenyl)ethyl)-1-piperazinyl)-4-pyrimidinyl)oxy)-1-methyl-2(1H)-quinoxalinone;

3-amino-5-((6-(4-((1R)-1-(4-fluorophenyl)ethyl)-1-piperazinyl)-4-pyrimidinyl)oxy)-1-methyl-2(1H)-quinoxalinone;

3-amino-5-((6-(4-((1S)-1-(4-fluorophenyl)ethyl)-1-piperazinyl)-4-pyrimidinyl)oxy)-2(1H)-quinoxalinone;

3-amino-5-((6-(4-((1S)-1-(4-fluorophenyl)ethyl)-1-piperazinyl)-4-pyrimidinyl)oxy)-1-methyl-2(1H)-quinoxalinone;

3-amino-5-((6-(4-((1S,1R)-1-(4-fluorophenyl)ethyl)-1-piperazinyl)-4-pyrimidinyl)oxy)-2(1H)-quinoxalinone;

3-amino-7-fluoro-5-((6-(4-((1R)-1-(4-fluorophenyl)ethyl)-1-piperazinyl)-4-pyrimidinyl)oxy)-2(1H)-quinoxalinone;

3-amino-7-fluoro-5-((6-(4-((1R)-1-(4-fluorophenyl)ethyl)-1-piperazinyl)-4-pyrimidinyl)oxy)-2(1H)-quinoxalinone;

3-amino-7-fluoro-5-((6-(4-((1S)-1-(4-fluorophenyl)ethyl)-1-piperazinyl)-4-pyrimidinyl)oxy)-2(1H)-quinoxalinone;

4-((6-(4-((1R)-1-(4-fluorophenyl)ethyl)-1-piperazinyl)-4-pyrimidinyl)oxy)quinoline;

4-((6-(4-((1R)-1-(4-fluorophenyl)ethyl)-1-piperazinyl)-4-pyrimidinyl)oxy)isoquinoline;

4-((6-(4-((1R)-1-(4-fluorophenyl)ethyl)-1-piperazinyl)-4-pyrimidinyl)oxy)-1,3-benzothiazol-2-amine;

4-((6-(4-((1S)-1-(4-fluorophenyl)ethyl)-1-piperazinyl)-4-pyrimidinyl)oxy)-1,3-dihydro-2H-benzimidazol-2-one;

4-((6-(4-((1S)-1-(4-fluorophenyl)ethyl)-1-piperazinyl)-4-pyrimidinyl)oxy)-2-methyl-1H-benzimidazole;

4-((6-(4-((1S)-1-(4-fluorophenyl)ethyl)-1-piperazinyl)-4-pyrimidinyl)oxy)-1H-indole;

4-((6-(4-((1S)-1-(4-fluorophenyl)ethyl)-1-piperazinyl)-4-pyrimidinyl)oxy)-1,3-benzoxazol-2-amine;

4-(2,3-dihydro-1,4-benzodioxin-6-yloxy)-6-(4-((1S)-1-(4-fluorophenyl)ethyl)-1-piperazinyl)pyrimidine;

4-(2,3-dihydro-benzo[1,4]dioxin-5-yloxy)-6-{4-[1-(4-fluoro-phenyl)-ethyl]-piperazin-1-yl}-pyrimidine;

5-((6-(4-((1R)-1-(4-fluorophenyl)ethyl)-1-piperazinyl)-4-pyrimidinyl)oxy)-1,4-dihydro-2,3-quinoxalinedione;

5-((6-(4-((1R)-1-(4-fluorophenyl)ethyl)-1-piperazinyl)-4-pyrimidinyl)oxy)isoquinoline;

5-((6-(4-((1R)-1-(4-fluorophenyl)ethyl)-1-piperazinyl)-4-pyrimidinyl)oxy)quinoline;

5-((6-(4-((1R)-1-(4-fluorophenyl)ethyl)-1-piperazinyl)-4-pyrimidinyl)oxy)-3,4-dihydro-1(2H)-isoquinolinone;

5-((6-(4-((1R)-1-(4-fluorophenyl)ethyl)-1-piperazinyl)-4-pyrimidinyl)oxy)-2(1H)-quinolinone;

5-((6-(4-((1R)-1-(4-fluorophenyl)ethyl)-1-piperazinyl)-4-pyrimidinyl)oxy)-3,4-dihydro-2(1H)-quinolinone;

5-((6-(4-((1S)-1-(4-fluorophenyl)ethyl)-1-piperazinyl)-4-pyrimidinyl)oxy)-1,3-dihydro-2H-benzimidazol-2-one;

5-((6-(4-((1S)-1-(4-fluorophenyl)ethyl)-1-piperazinyl)-4-pyrimidinyl)oxy)-3,3-dimethyl-1,3-dihydro-2H-indol-2-one;

5-((6-(4-((1S)-1-(4-fluorophenyl)ethyl)-1-piperazinyl)-4-pyrimidinyl)oxy)-1,3-benzothiazol-2-amine;

5-((6-(4-((1S)-1-(4-fluorophenyl)ethyl)-1-piperazinyl)-4-pyrimidinyl)oxy)-2(1H)-quinoxalinone;

5-((6-(4-((1S)-1-(4-fluorophenyl)ethyl)-1-piperazinyl)-4-pyrimidinyl)oxy)-3,4-dihydro-2(1H)-quinoxalinone;

5-((6-(4-((1S)-1-(4-fluorophenyl)ethyl)-1-piperazinyl)-4-pyrimidinyl)oxy)-4a,8a-dihydroquinoxaline;

5-((6-(4-((1S)-1-(4-fluorophenyl)ethyl)-1-piperazinyl)-4-pyrimidinyl)oxy)-1(2H)-isoquinolinone;

6-((6-(4-((1S)-1-(4-fluorophenyl)ethyl)-1-piperazinyl)-4-pyrimidinyl)oxy)-1H-indole;

6-((6-(4-((1S)-1-(4-fluorophenyl)ethyl)-1-piperazinyl)-4-pyrimidinyl)oxy)-2H-1,4-benzoxazin-3(4H)-one;

6-((6-(4-((1S)-1-(4-fluorophenyl)ethyl)-1-piperazinyl)-4-pyrimidinyl)oxy)isoquinoline;

6-((6-(4-((1S)-1-(4-fluorophenyl)ethyl)-1-piperazinyl)-4-pyrimidinyl)oxy)-3,4-dihydro-2H-1,4-benzoxazine;

6-((6-(4-((1S)-1-(4-fluorophenyl)ethyl)-1-piperazinyl)-4-pyrimidinyl)oxy)quinoline;

7-((6-(4-((1S)-1-(4-fluorophenyl)ethyl)-1-piperazinyl)-4-pyrimidinyl)oxy)-1H-indole;

7-((6-(4-((1S)-1-(4-fluorophenyl)ethyl)-1-piperazinyl)-4-pyrimidinyl)oxy)quinoline;

7-((6-(4-((1S)-1-(4-fluorophenyl)ethyl)-1-piperazinyl)-4-pyrimidinyl)oxy)isoquinoline;

7-((6-(4-((1S)-1-(4-fluorophenyl)ethyl)-1-piperazinyl)-4-pyrimidinyl)oxy)-2-quinolinol;

8-((6-(4-((1R)-1-(4-fluorophenyl)ethyl)-1-piperazinyl)-4-pyrimidinyl)oxy)-2-quinolinamine;

8-((6-(4-((1R)-1-(4-fluorophenyl)ethyl)-1-piperazinyl)-4-pyrimidinyl)oxy)-2-quinoxalinamine;

8-((6-(4-((1R)-1-(4-fluorophenyl)ethyl)-1-piperazinyl)-4-pyrimidinyl)oxy)quinoline;

8-((6-(4-((1S)-1-(4-fluorophenyl)ethyl)-1-piperazinyl)-4-pyrimidinyl)oxy)-2-quinolinamine;

8-((6-(4-((1S)-1-(4-fluorophenyl)ethyl)-1-piperazinyl)-4-pyrimidinyl)oxy)imidazo[1,2-a]pyridine;

8-((6-(4-((1S)-1-(4-fluorophenyl)ethyl)-1-piperazinyl)-4-pyrimidinyl)oxy)-1,4-dihydro-3(2H)-isoquinolinone;

8-((6-(4-((1S)-1-(4-fluorophenyl)ethyl)-1-piperazinyl)-4-pyrimidinyl)oxy)-2-quinoxalinamine;

8-((6-(4-((1S)-1-(4-fluorophenyl)ethyl)-1-piperazinyl)-4-pyrimidinyl)oxy)isoquinoline;

N-(4-((6-((2R)-4-((1R)-1-(4-fluorophenyl)ethyl)-2-methyl-1-piperazinyl)-4-pyrimidinyl)oxy)-1,3-benzothiazol-2-yl)acetamide;

N-(4-((6-((2R)-4-((1S)-1-(4-fluorophenyl)ethyl)-2-methyl-1-piperazinyl)-4-pyrimidinyl)oxy)-1,3-benzothiazol-2-yl)acetamide;

N-(4-((6-((2R)-4-((1S)-1-(4-fluorophenyl)ethyl)-2-methyl-1-piperazinyl)-4-pyrimidinyl)oxy)-1,3-benzothiazol-2-yl)acetamide;

N-(4-((6-((2S)-4-((1S,1R)-1-(4-fluorophenyl)ethyl)-2-methyl-1-piperazinyl)-4-pyrimidinyl)oxy)-1,3-benzothiazol-2-yl)acetamide;

N-(4-((6-((3R)$_4$-((1R)-1-(4-fluorophenyl)ethyl)-3-methyl-1-piperazinyl)-4-pyrimidinyl)oxy)-1,3-benzothiazol-2-yl)acetamide;

N-(4-((6-((3R)-4-((1R)-1-(4-fluorophenyl)propyl)-3-methyl-1-piperazinyl)-4-pyrimidinyl)oxy)-1,3-benzothiazol-2-yl)acetamide;

N-(4-((6-((3R)-4-((1S)-1-(4-fluorophenyl)ethyl)-3-methyl-1-piperazinyl)-4-pyrimidinyl)oxy)-1,3-benzothiazol-2-yl)acetamide;

N-(4-((6-((3R)$_4$-((1S)-1-(4-fluorophenyl)propyl)-3-methyl-1-piperazinyl)-4-pyrimidinyl)oxy)-1,3-benzothiazol-2-yl)acetamide;

N-(4-((6-(4-((1R)-1-(4-fluorophenyl)ethyl)-1-piperazinyl)-4-pyrimidinyl)oxy)-1,3-benzothiazol-2-yl)acetamide;

N-(4-((6-(4-((1S)-1-(4-fluorophenyl)ethyl)-1-piperazinyl)-4-pyrimidinyl)oxy)-1,3-benzothiazol-2-yl)acetamide;

N-(4-((6-(4-((1S)-1-(4-fluorophenyl)ethyl)-1-piperazinyl)-4-pyrimidinyl)oxy)-1,3-benzoxazol-2-yl)acetamide;

N-(4-((6-(4-((1S,1R)-1-(2,4-difluorophenyl)ethyl)-1-piperazinyl)-4-pyrimidinyl)oxy)-1,3-benzothiazol-2-yl)acetamide;

N-(4-((6-(4-((1S,1R)-1-(2-fluorophenyl)ethyl)-1-piperazinyl)-4-pyrimidinyl)oxy)-1,3-benzothiazol-2-yl)acetamide;

N-(4-((6-(4-((1S,1R)-1-(2-furanyl)ethyl)-1-piperazinyl)-4-pyrimidinyl)oxy)-1,3-benzothiazol-2-yl)acetamide;

N-(4-((6-(4-((1S,1R)-1-(2-thienyl)ethyl)-1-piperazinyl)-4-pyrimidinyl)oxy)-1,3-benzothiazol-2-yl)acetamide;

N-(4-((6-(4-((1S,1R)-1-(3-fluorophenyl)ethyl)-1-piperazinyl)-4-pyrimidinyl)oxy)-1,3-benzothiazol-2-yl)acetamide;

N-(4-((6-(4-((1S,1R)-1-(3-thienyl)ethyl)-1-piperazinyl)-4-pyrimidinyl)oxy)-1,3-benzothiazol-2-yl)acetamide;

N-(4-((6-(4-((1S,1R)-1-(4-(methyloxy)phenyl)ethyl)-1-piperazinyl)-4-pyrimidinyl)oxy)-1,3-benzothiazol-2-yl)acetamide;

N-(4-((6-(4-((1S,1R)-1-(4-(trifluoromethyl)phenyl)ethyl)-1-piperazinyl)-4-pyrimidinyl)oxy)-1,3-benzothiazol-2-yl)acetamide;

N-(4-((6-(4-((1S,1R)-1-(4-bromophenyl)ethyl)-1-piperazinyl)-4-pyrimidinyl)oxy)-1,3-benzothiazol-2-yl)acetamide;

N-(4-((6-(4-((1S,1R)-1-(4-chlorophenyl)ethyl)-1-piperazinyl)-4-pyrimidinyl)oxy)-1,3-benzothiazol-2-yl)acetamide;

N-(4-((6-(4-((1S,1R)-1-(4-fluorophenyl)ethyl)-1-piperazinyl)-4-pyrimidinyl)oxy)-1,3-benzothiazol-2-yl)acetamide;

N-(4-((6-(4-((S, 1R)-1-(4-fluorophenyl)propyl)-1-piperazinyl)-4-pyrimidinyl)oxy)-1,3-benzothiazol-2-yl)acetamide;

N-(4-((6-(4-((1S,1R)-1-(4-pyridinyl)ethyl)-1-piperazinyl)-4-pyrimidinyl)oxy)-1,3-benzothiazol-2-yl)acetamide;

N-(4-((6-(4-((1S,1R)-1-(5-bromo-2-thienyl)ethyl)-1-piperazinyl)-4-pyrimidinyl)oxy)-1,3-benzothiazol-2-yl)acetamide;

N-(4-((6-(4-((1S,1R)-1-(5-chloro-2-thienyl)ethyl)-1-piperazinyl)-4-pyrimidinyl)oxy)-1,3-benzothiazol-2-yl)acetamide; and N-(8-((6-(4-((1R)-1-(4-fluorophenyl)ethyl)-1-piperazinyl)-4-pyrimidinyl)oxy)-2-quinolinyl)acetamide;

or any pharmaceutically-acceptable salts or hydrate thereof.

5. A pharmaceutical composition comprising a compound according to claim 1 and a pharmaceutically-acceptable diluent or carrier.

* * * * *

UNITED STATES PATENT AND TRADEMARK OFFICE
CERTIFICATE OF CORRECTION

PATENT NO. : 7,511,044 B2 Page 1 of 1
APPLICATION NO. : 11/056568
DATED : March 31, 2009
INVENTOR(S) : Wang et al.

It is certified that error appears in the above-identified patent and that said Letters Patent is hereby corrected as shown below:

Column 79 line 8 change "((S,1R)" to read --((1S,1R)--.

Column 80 line 9 change "salts or hydrate thereof." to read --salts thereof.--.

Signed and Sealed this

Twenty-third Day of June, 2009

JOHN DOLL
*Acting Director of the United States Patent and Trademark Office*